(12) United States Patent
Braido et al.

(10) Patent No.: US 9,808,201 B2
(45) Date of Patent: Nov. 7, 2017

(54) SENSORS FOR PROSTHETIC HEART DEVICES

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Steven Frederick Anderl, Forest Lake, MN (US); Jason White, Smyrna, GA (US); Paul E. Ashworth, Wyoming, MN (US); Morgan Low, Winnetka, CA (US); Loell Boyce Moon, Ham Lake, MN (US); Neelakantan Saikrishnan, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 14/825,471

(22) Filed: Aug. 13, 2015

(65) Prior Publication Data
US 2016/0045165 A1   Feb. 18, 2016

Related U.S. Application Data

(60) Provisional application No. 62/038,512, filed on Aug. 18, 2014.

(51) Int. Cl.
*A61F 2/24* (2006.01)
*A61B 5/00* (2006.01)
(Continued)

(52) U.S. Cl.
CPC ............. *A61B 5/6862* (2013.01); *A61B 5/02* (2013.01); *A61B 5/026* (2013.01); *A61B 5/0215* (2013.01);
(Continued)

(58) Field of Classification Search
CPC ........ A61F 2/24; A61F 2/2412; A61F 2/2418; A61F 2/2472; A61B 5/02; A61B 5/02158; A61B 5/026; A61B 2562/0247
See application file for complete search history.

(56) References Cited

U.S. PATENT DOCUMENTS

| 4,275,469 A | 6/1981 | Gabbay |
| 4,491,986 A | 1/1985 | Gabbay |

(Continued)

FOREIGN PATENT DOCUMENTS

| DE | 19857887 B4 | 5/2005 |
| DE | 10121210 B4 | 11/2005 |

(Continued)

OTHER PUBLICATIONS

International Search Report and Written Opinion for Application No. PCT/US2015/044969 dated Dec. 11, 2015.
(Continued)

*Primary Examiner* — David Isabella
*Assistant Examiner* — Dinah Baria
(74) *Attorney, Agent, or Firm* — Lerner, David, Littenberg, Krumholz & Mentlik, LLP

(57) ABSTRACT

Prosthetic heart devices may be implanted into the heart with a sensor coupled to the device, the sensor being configured to measure physiological data, such as blood pressure, in the heart. Devices that may employ such sensors include prosthetic heart valves and occlusion devices, although sensor systems may be deployed in the heart separate from other implantable devices. The sensors may include a body with different configurations for attaching to the implantable device, such as apertures for sutures or fingers for connecting to structures of the implantable device. The sensors may provide data that allow a determination of aortic regurgitation or other information indicative
(Continued)

of function of the implantable device and patient health during and after implantation of the device.

16 Claims, 35 Drawing Sheets

(51) Int. Cl.
    *A61F 2/844* (2013.01)
    *A61B 5/0215* (2006.01)
    *A61B 5/02* (2006.01)
    *A61B 5/026* (2006.01)
    *A61B 17/00* (2006.01)
    *A61B 17/12* (2006.01)

(52) U.S. Cl.
    CPC ...... *A61B 5/02028* (2013.01); *A61B 5/02158* (2013.01); *A61B 5/6847* (2013.01); *A61B 17/0057* (2013.01); *A61B 17/12122* (2013.01); *A61F 2/24* (2013.01); *A61F 2/2412* (2013.01); *A61F 2/2418* (2013.01); *A61F 2/2445* (2013.01); *A61F 2/2448* (2013.01); *A61F 2/2472* (2013.01); *A61F 2/844* (2013.01); *A61B 2017/00022* (2013.01); *A61B 2017/00575* (2013.01); *A61B 2017/00632* (2013.01); *A61B 2562/0247* (2013.01); *A61F 2210/0066* (2013.01); *A61F 2220/0016* (2013.01); *A61F 2220/0075* (2013.01); *A61F 2230/0008* (2013.01); *A61F 2230/0034* (2013.01); *A61F 2230/0065* (2013.01); *A61F 2250/001* (2013.01); *A61F 2250/0002* (2013.01); *A61F 2250/0004* (2013.01); *A61F 2250/0063* (2013.01); *A61F 2250/0065* (2013.01)

(56) References Cited

U.S. PATENT DOCUMENTS

| | | |
|---|---|---|
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,487,760 A | 1/1996 | Villafana |
| 5,847,760 A | 12/1998 | Elmaliach et al. |
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,287,339 B1 | 9/2001 | Vazquez et al. |
| 6,331,163 B1 * | 12/2001 | Kaplan ............... A61B 5/0031 600/373 |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,909,770 B2 | 3/2011 | Stern et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2005/0060030 A1 | 3/2005 | Lashinski et al. |
| 2005/0096726 A1 | 5/2005 | Sequin et al. |
| 2005/0154321 A1 | 7/2005 | Wolinsky et al. |
| 2005/0165317 A1 | 7/2005 | Turner et al. |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0129216 A1 | 6/2006 | Hastings et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067027 A1 | 3/2007 | Moaddeb et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0129637 A1 | 6/2007 | Wolinsky et al. |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0288087 A1 | 12/2007 | Fearnot et al. |
| 2008/0021552 A1 | 1/2008 | Gabbay |
| 2008/0027483 A1 | 1/2008 | Cartledge et al. |
| 2008/0039934 A1 | 2/2008 | Styrc |
| 2008/0051838 A1 | 2/2008 | Shuros et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0234404 A1 | 9/2009 | Fitzgerald et al. |

(56) References Cited

U.S. PATENT DOCUMENTS

| | | |
|---|---|---|
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2013/0006352 A1 | 1/2013 | Yaron |
| 2016/0045316 A1* | 2/2016 | Braido .............. A61B 5/6862 623/2.38 |
| 2016/0256274 A1 | 9/2016 | Hayoz |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1050265 A2 | 11/2000 |
| EP | 1584306 A1 | 10/2005 |
| EP | 1598031 A2 | 11/2005 |
| EP | 1360942 B1 | 12/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 03103539 A1 | 12/2003 |
| WO | 2005055883 A1 | 6/2005 |
| WO | 2006073626 A2 | 7/2006 |
| WO | 2008006003 A2 | 1/2008 |
| WO | 2008024180 A1 | 2/2008 |
| WO | 2008071817 A1 | 6/2008 |
| WO | 2009006602 A1 | 1/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012106344 A1 | 8/2012 |
| WO | 2015058808 A1 | 4/2015 |

OTHER PUBLICATIONS

International Search Report and Written Opinion for Application No. PCT/US2015/044962 dated Oct. 30, 2015.
Catheter-implanted prosthetic heart valves, Knudsen, L.L., et al., The International Journal of Artificial Organs, vol. 16, No. 5 1993, pp. 253-262.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is it Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

* cited by examiner

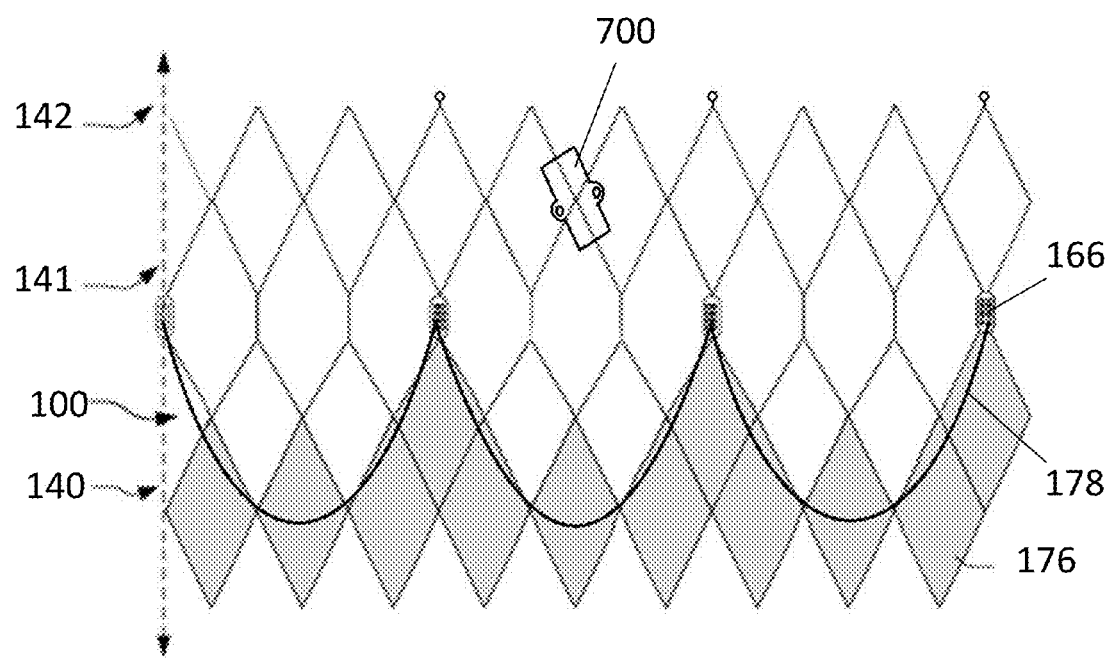
FIG. 8B
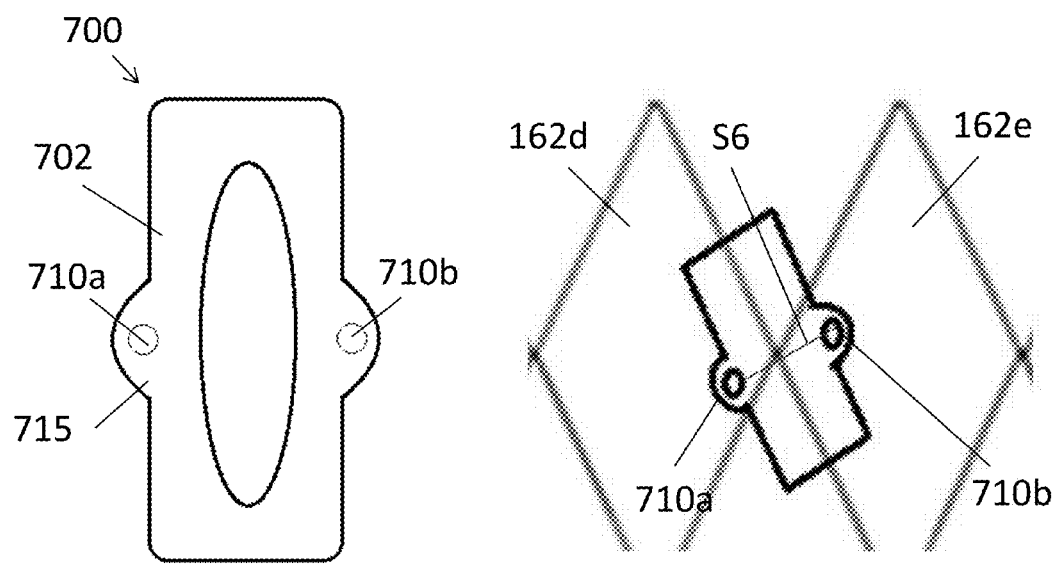
FIG. 8A  FIG. 8C

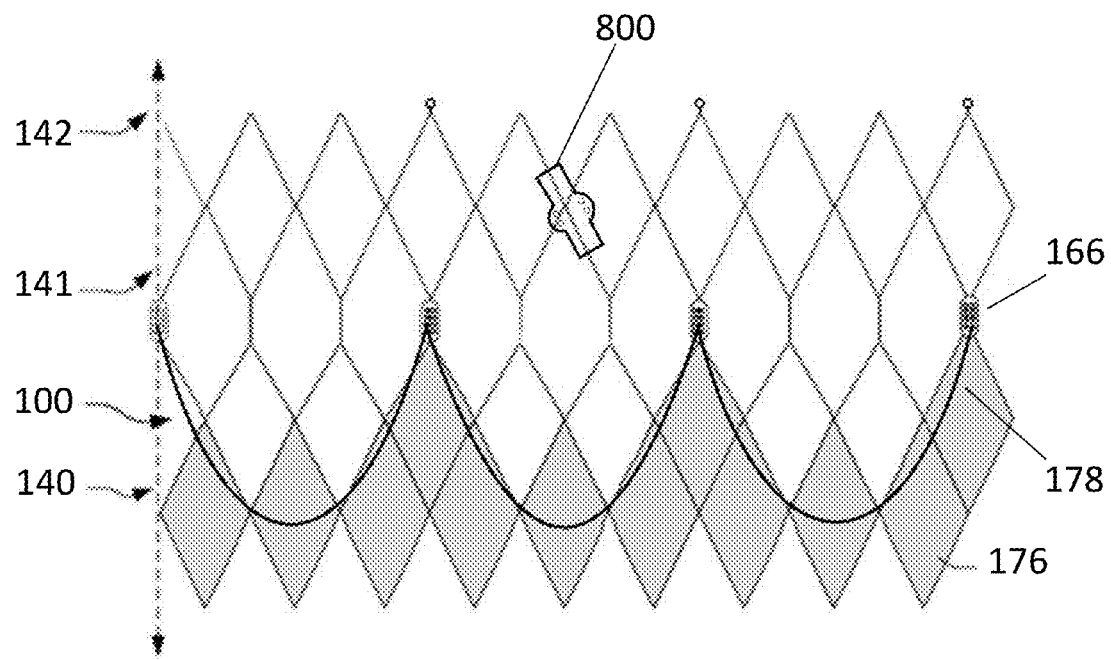
FIG. 9B
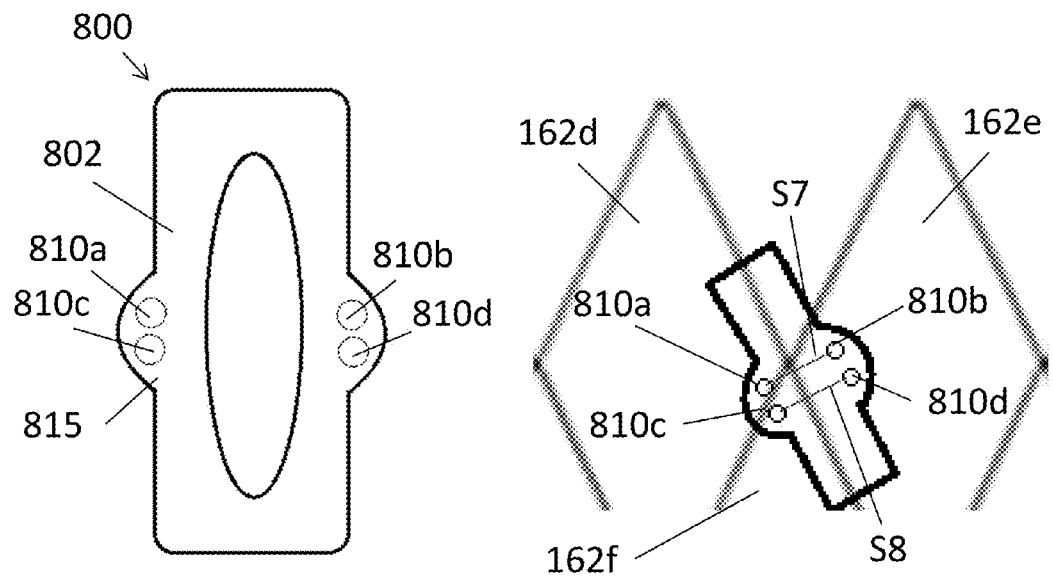
FIG. 9A
FIG. 9C

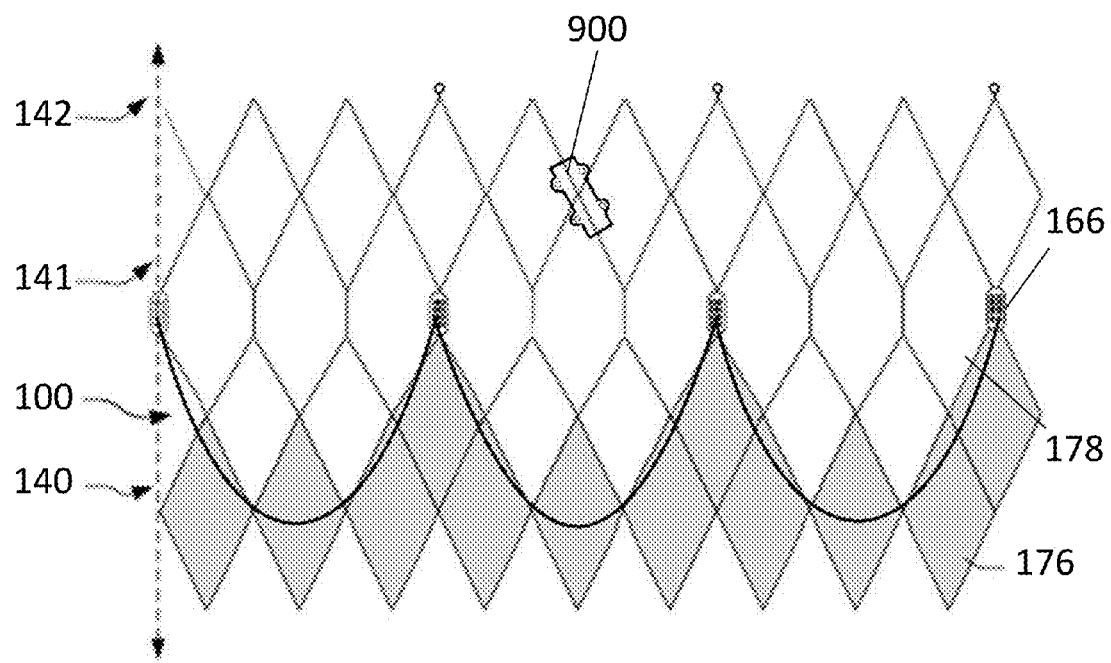
FIG. 10B
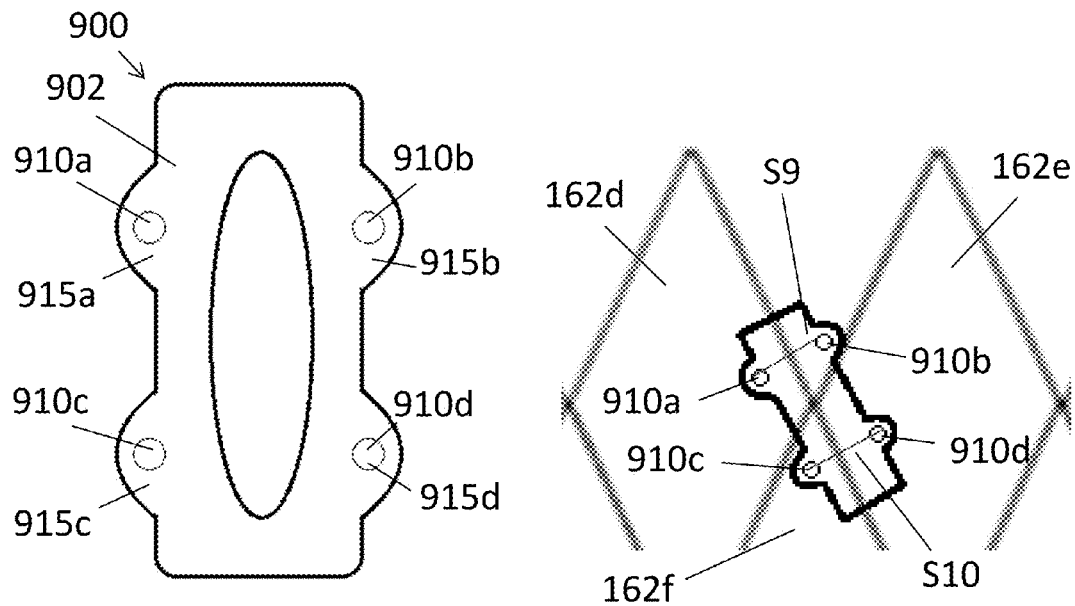
FIG. 10A            FIG. 10C

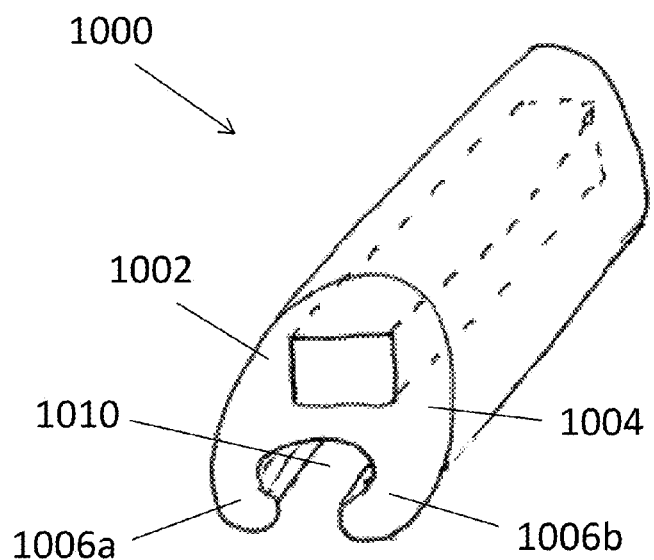
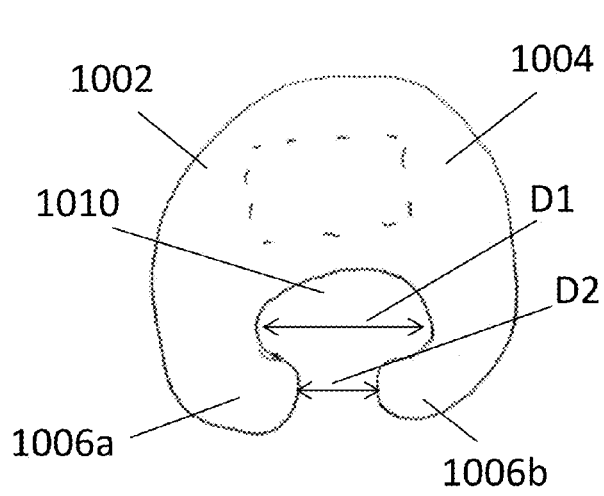 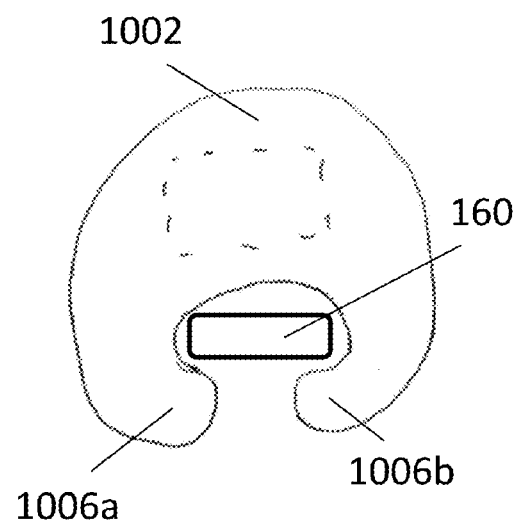
FIG. 11A
FIG. 11B  FIG. 11C

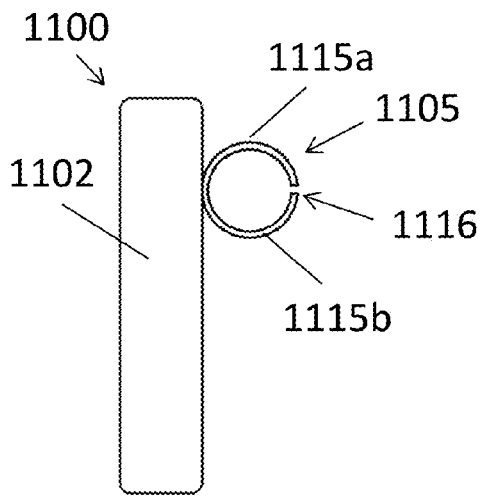
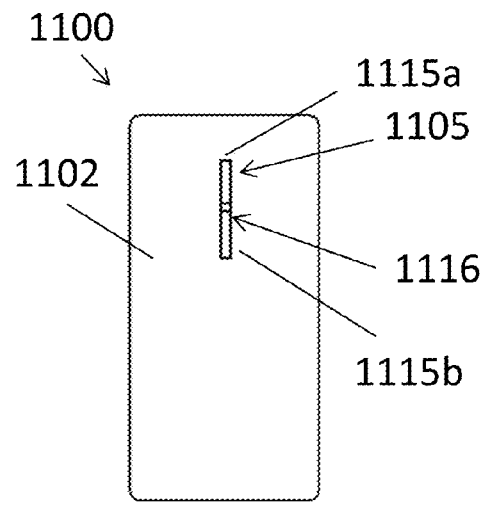
FIG. 12A  FIG. 12B
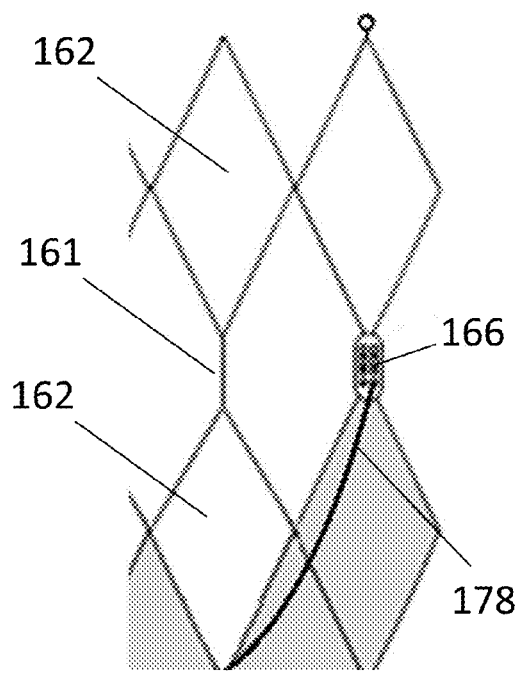
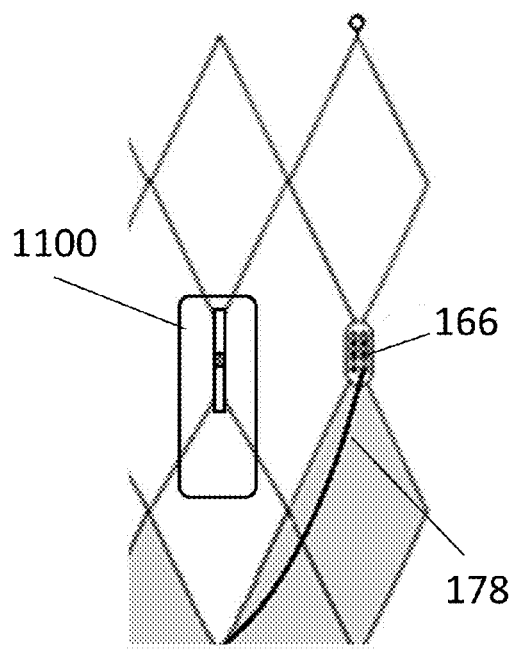
FIG. 12C  FIG. 12D

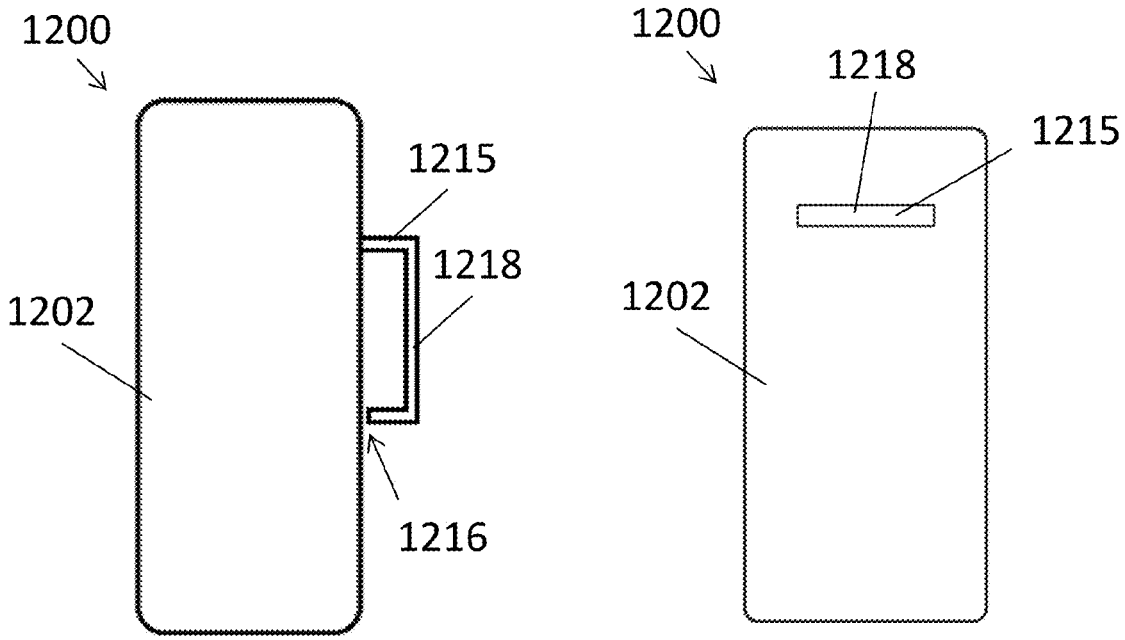
FIG. 13A  FIG. 13B
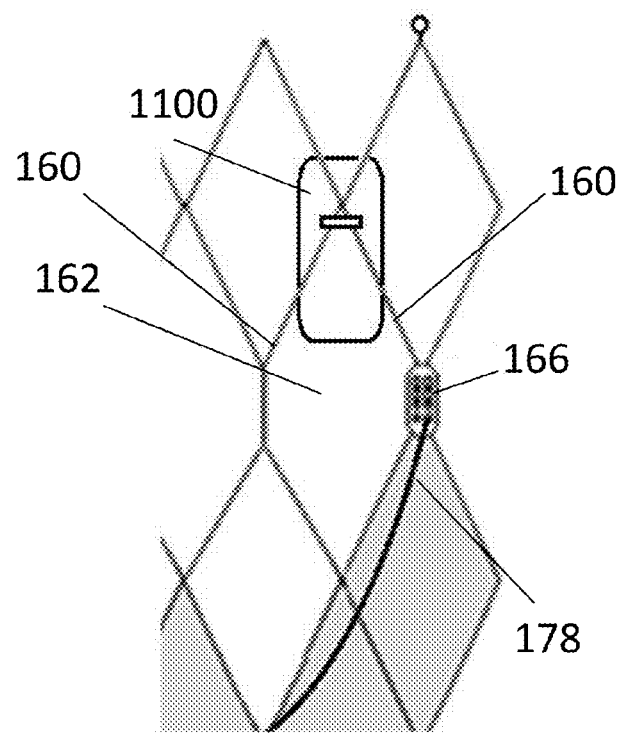
FIG. 13C

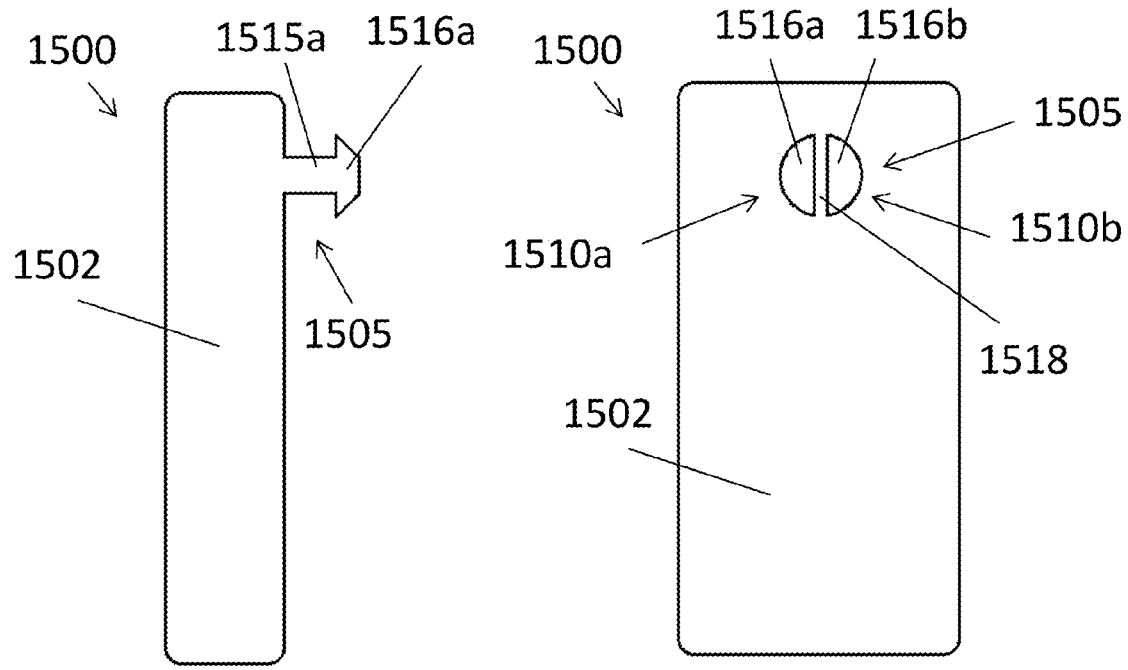
FIG. 16A  FIG. 16B
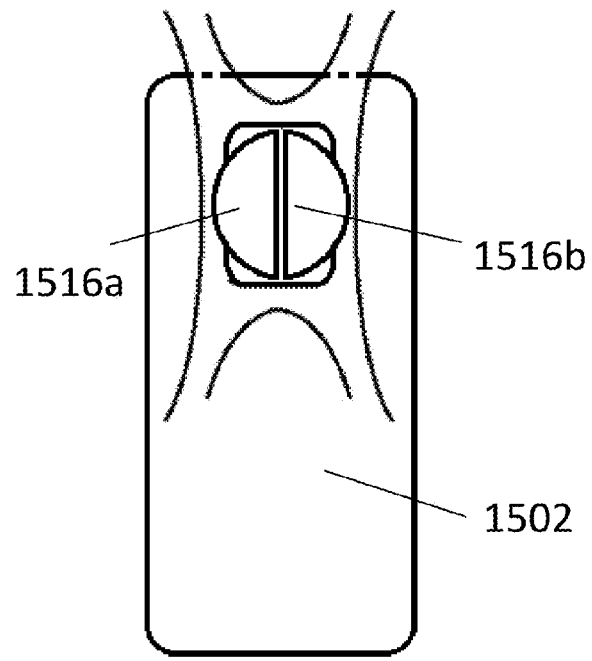
FIG. 16C

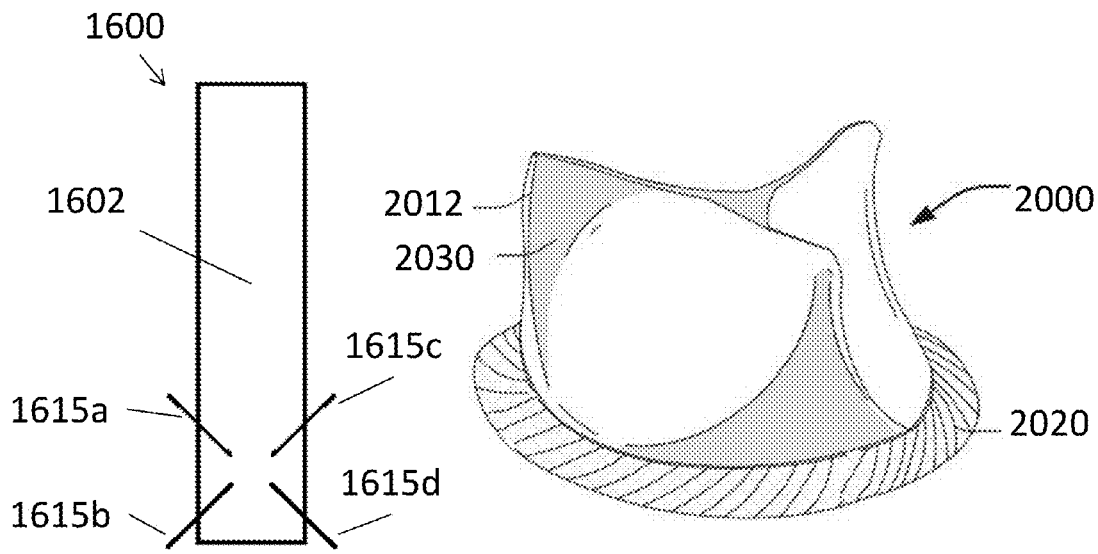
FIG. 17A
FIG. 17B
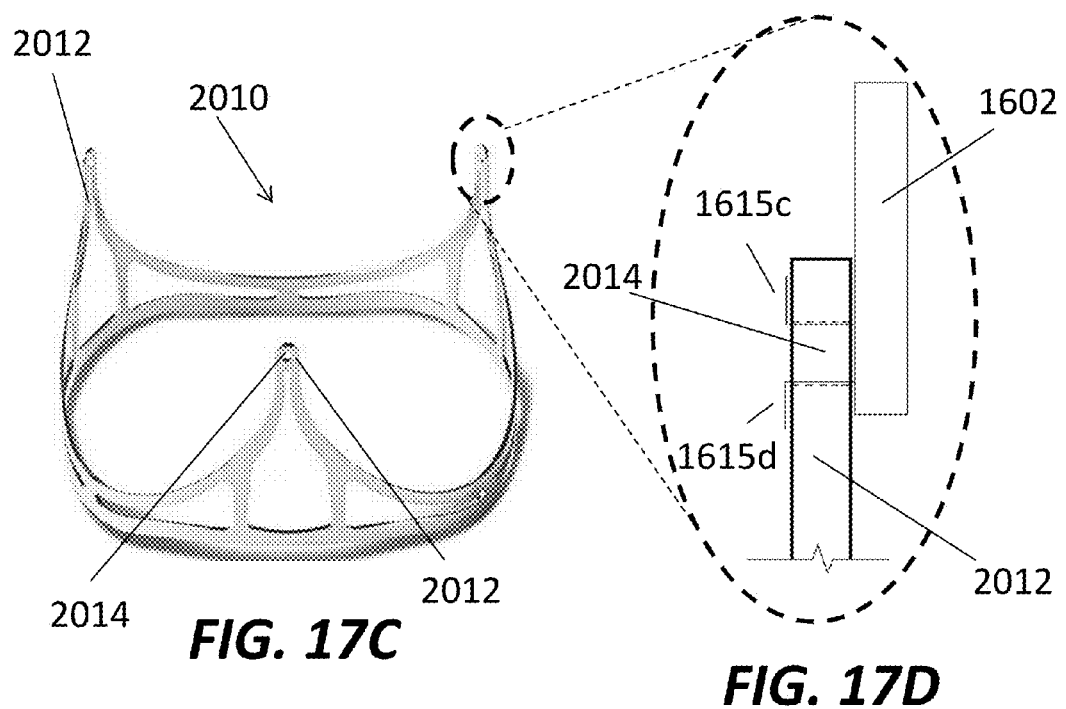
FIG. 17C
FIG. 17D

SENSORS FOR PROSTHETIC HEART DEVICES

CROSS-REFERENCE TO RELATED APPLICATIONS

The present application claims the benefit of the filing date of U.S. Provisional Patent Application No. 62/038,512, titled "Prosthetic Heart Devices Having Diagnostic Capabilities," filed Aug. 18, 2014, the disclosure of which is hereby incorporated by reference herein.

BACKGROUND

The present disclosure relates to heart valve replacement and repair devices such as collapsible prosthetic heart valves. More particularly, the present disclosure relates to devices and methods for using prosthetic heart devices having diagnostic capabilities.

Diseased or damaged native heart valves may be repaired or replaced using prosthetic devices. In some instances, devices such as annuloplasty rings are used to repair and restore the function of a malfunctioning native heart valve. If repair is not possible, the function of native heart valves may be replaced by prosthetic devices, such as surgical valves. Such a replacement typically requires an open-heart surgical procedure.

In addition to these devices, prosthetic heart valves that are collapsible to a relatively small circumferential size can be delivered into a patient less invasively than surgical valves. For example, a collapsible valve may be delivered into a patient via a tube-like delivery apparatus such as a catheter, a trocar, a laparoscopic instrument, or the like. This collapsibility can avoid the need for more invasive procedures such as full open-chest, open-heart surgery.

Collapsible prosthetic heart valves (sometimes referred to herein as transcatheter valves or transcatheter implants) typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

It would be advantageous to monitor the function of prosthetic devices, including annuloplasty rings, surgical valves and transcatheter valves, before, during and after implantation to ensure proper functioning for short-term and long-term assessment. For example, calcification of the aortic valve may affect the performance and anchoring of transcathether implants. Calcification may also be associated with leakage, such as paravalvular leakage around the exterior of a medical device or aortic regurgitation through the interior of a medical device.

There therefore is a need for improvements in the devices, systems, and methods for monitoring prosthetic heart devices before, during and after implantation. Specifically, there is a need for improvements in the devices, systems, and methods for accurately measuring parameters associated with proper prosthetic heart valve functionality. Among other advantages, the present disclosure may address one or more of these needs.

BRIEF SUMMARY

According to one embodiment of the disclosure, a prosthetic heart valve system comprising includes a prosthetic heart valve and a first sensor. The prosthetic heart valve includes a stent extending from an outflow portion to an inflow portion and having an expanded condition and a collapsed condition, and a valve assembly mounted to the stent. The first sensor is configured to measure physiological data, the first sensor including a body and a plurality of apertures extending through the body and adapted to receive at least one suture therethrough for attaching the sensor to the stent.

According to another embodiment of the disclosure, a prosthetic heart valve system includes a prosthetic heart valve and a sensor. The prosthetic heart valve includes a stent extending from an outflow portion to an inflow portion and has an expanded condition and a collapsed condition, and a valve assembly mounted to the stent. The sensor is configured to measure physiological data, the sensor including a body, the body having a first side, a second side opposite the first side, and a pair of fingers extending away from the body on the first side of the body, the fingers and the first side of the body defining a channel extending along a length of the body, the sensor being connectable to the stent.

According to a further embodiment of the disclosure, a prosthetic heart valve system includes a prosthetic heart valve and a sensor. The prosthetic heart valve includes a stent extending from an outflow portion to an inflow portion and has an expanded condition and a collapsed condition, and a valve assembly mounted to the stent. The sensor is configured to measure physiological data, the sensor including a body. A first finger has a first end attached to the body and a free end, the free end being configured to hook over at least one strut of the stent to attach the sensor to the stent.

According to another embodiment of the disclosure, a prosthetic heart valve system includes a prosthetic heart valve and a sensor. The prosthetic heart valve includes a stent extending from an outflow portion to an inflow portion and has an expanded condition and a collapsed condition, the stent being formed of a plurality of struts, a strut aperture being formed at an intersection of at least two of the struts, and a valve assembly mounted to the stent. The sensor is configured to measure physiological data, the sensor including a body, the body being configured to be coupled to the stent. The body includes a first body section having a first width, a middle body section having a second width smaller than the first width, and a third body section having a third width greater than the second width and smaller than the first width.

According to still another embodiment of the disclosure, a prosthetic heart valve system includes a prosthetic heart valve and a sensor. The prosthetic heart valve includes a stent extending from an outflow portion to an inflow portion and has an expanded condition and a collapsed condition, the stent being formed of a plurality of struts, a strut aperture being formed at an intersection of at least two of the struts. A valve assembly is mounted to the stent. The sensor is configured to measure physiological data, the sensor including a body configured to be coupled to the stent. The body includes a head having a first width and a shank having a second width smaller than the first width.

According to yet another embodiment of the disclosure, a prosthetic heart valve system includes a prosthetic heart valve and a sensor. The prosthetic heart valve includes a stent extending from an outflow portion to an inflow portion and has an expanded condition and a collapsed condition, the stent being formed of a plurality of struts, a strut aperture being formed at an intersection of at least two of the struts. A valve assembly is mounted to the stent. The sensor is configured to measure physiological data, the sensor including a body, the body including a connecting member adapted to couple the sensor to the stent, the connecting member including a shaft projecting away from the body to a free end, and a head at the free end of the shaft.

According to a further embodiment of the disclosure, a prosthetic heart valve system includes a prosthetic heart valve and a sensor. The prosthetic heart valve includes a stent extending from an outflow portion to an inflow portion and having a plurality of stent posts, at least one stent post defining an aperture. The sensor is configured to measure physiological data, the sensor including a body, the body including a plurality of fingers extending away from the body for connecting the sensor to the stent, at least two of the fingers extending away from one another in the absence of applied forces.

According to still another embodiment of the disclosure, a sensor system includes a collapsible and expandable sensor frame having an outflow frame section, an inflow frame section, and a frame coupling portion connecting the outflow frame section to the inflow frame section. A first sensor is coupled to the sensor frame, the first sensor including a body, the first sensor being configured to measure physiological data. A second sensor is coupled to the sensor frame, the second sensor including a body, the second sensor being configured to measure physiological data. In an expanded condition the outflow frame section and inflow frame section each has an arcuate configuration.

According to another embodiment of the disclosure, a prosthetic heart valve system includes a prosthetic heart valve and two sensors. The prosthetic heart valve includes a support structure extending from an outflow portion to an inflow portion, a cuff attached to the inflow portion of the support structure, and a valve assembly mounted to the support structure. The first sensor includes a body and is configured to measure physiological data and has a male coupling portion extending from the body. The second sensor includes a body and is configured to measure physiological data and has a female coupling, the male coupling portion of the first sensor configured to mate with the female coupling portion of the second sensor.

According to yet another embodiment of the disclosure, a prosthetic heart valve system includes a prosthetic heart valve and a first sensor. The prosthetic heart valve includes a stent extending from an outflow portion to an inflow portion and has an expanded condition and a collapsed condition. The stent includes a plurality of struts defining at least one annular row of cells, at least one engaging arm, and at least one commissure attachment feature positioned at a terminal end of the stent. The engaging arm has a first position and is nested within one of the cells and a second position projecting outwardly from the one cell. A valve assembly is mounted to the stent. The first sensor includes a body and is configured to measure physiological data and is coupled to the engaging arm or to the commissure attachment feature.

According to a further embodiment of the disclosure, a prosthetic heart valve system includes a prosthetic heart valve, an occlusion device, and a first sensor. The prosthetic heart valve includes a stent extending from an outflow portion to an inflow portion and has an expanded condition and a collapsed condition. A valve assembly is mounted to the stent. A collapsible and expandable occlusion device is configured for positioning between the prosthetic heart valve and a native valve annulus in which the prosthetic heart valve is implanted so that a first end of the occlusion device faces toward the outflow portion of the stent and a second end of the occlusion device faces toward the inflow portion of the stent. The first sensor is configured to be attached to the occlusion device, the first sensor including a body and being configured to measure physiological data.

In still a further embodiment of the disclosure, a collapsible and expandable occlusion system for placement within a vasculature of a patient includes a disc-shaped portion coupled to a cylindrical portion by a connector. The cylindrical portion has a first diameter and the disc-shaped portion has a second diameter greater than the first diameter when the occlusion system is in an expanded condition. A first sensor is configured to be attached to the cylindrical portion, the first sensor including a body and being configured to measure physiological data.

BRIEF DESCRIPTION OF THE DRAWINGS

FIG. 8A is a top plan view of a MEM sensor according to yet another embodiment of the disclosure.

FIG. 8B is a highly schematic developed view of the prosthetic heart valve of FIG. 1 in an expanded condition with the sensor of FIG. 8A attached thereto.

FIG. 8C is an enlarged partial view of the attached sensor of FIG. 8A.

FIG. 9A is a top plan view of a MEM sensor according to still another embodiment of the disclosure.

FIG. 9B is a highly schematic developed view of the prosthetic heart valve of FIG. 1 in an expanded condition with the sensor of FIG. 9A attached thereto.

FIG. 9C is an enlarged partial view of the attached sensor of FIG. 9A.

FIG. 10A is a top plan view of a MEM sensor according to another embodiment of the disclosure.

FIG. 10B is a highly schematic developed view of the prosthetic heart valve of FIG. 1 in an expanded condition with the sensor of FIG. 10A attached thereto.

FIG. 10C is an enlarged partial view of the attached sensor of FIG. 10A.

FIG. 11A is a perspective view of a MEM sensor according to a further embodiment of the disclosure.

FIG. 11B is a transverse cross-section of the sensor of FIG. 11A.

FIG. 11C is a transverse cross-section of the sensor of FIG. 11A coupled to a strut of the prosthetic heart valve of FIG. 1.

FIG. 12A is a side view of a MEM sensor according to still another embodiment of the disclosure.

FIG. 12B is a bottom plan view of the sensor of FIG. 12A.

FIG. 12C is an enlarged partial view of the heart valve of FIG. 1.

FIG. 12D is an enlarged partial view of the sensor of FIGS. 12A-B attached to the prosthetic heart valve of FIG. 1.

FIG. 13A is an enlarged top view of a MEM sensor according to yet another embodiment of the disclosure.

FIG. 13B is a bottom plan view of the sensor of FIG. 13A.

FIG. 13C is an enlarged partial view of the sensor of FIGS. 13A-B attached to the prosthetic heart valve of FIG. 1.

FIG. 16A is a side view of a MEM sensor according to still another embodiment of the disclosure.

FIG. 16B is a bottom plan view of the sensor of FIG. 16A.

FIG. 16C is an enlarged partial view of the sensor of FIGS. 16A-B attached to the modified stent of FIG. 14B.

FIG. 17A is a bottom plan view of a MEM sensor according to still a further embodiment of the disclosure.

FIG. 17B is a perspective view of a surgical prosthetic heart valve.

FIG. 17C is a perspective view of a stent for use in the prosthetic heart valve of FIG. 17B.

FIG. 17D is an enlarged side view of the sensor of FIG. 17A coupled to the stent of FIG. 17C.

DETAILED DESCRIPTION

As used herein in connection with prosthetic aortic heart valves and prosthetic pulmonary heart valves, the term "inflow end" refers to the end of the prosthetic heart valve closest to the left ventricle when implanted in an operative condition, whereas the term "outflow end" refers to the end of the prosthetic heart valve closest to the aorta.

Figure 1:
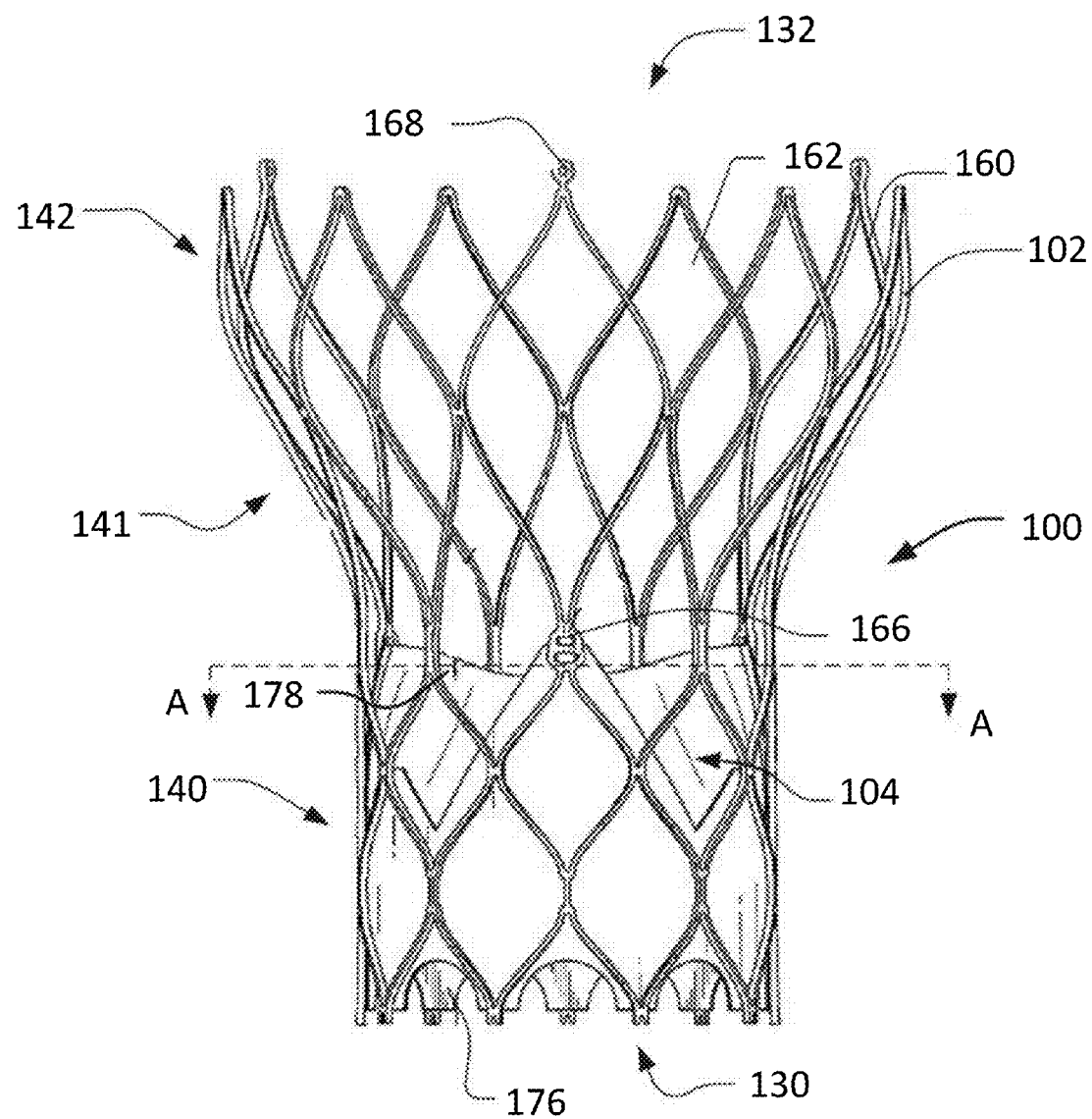
FIG. 1 is a side elevational view of a conventional prosthetic heart valve.

FIG. 1 shows one such collapsible stent-supported prosthetic heart valve 100 including a stent 102 and a valve assembly 104 as is known in the art. Prosthetic heart valve 100 is designed to replace a native tricuspid valve of a patient, such as a native aortic valve. It should be noted that while the embodiments discussed in connection with prosthetic aortic valves relate predominantly to such valves having a stent with a shape as illustrated in FIG. 1, the valve could be a bicuspid valve, such as the mitral valve, and the stent could have different shapes, such as a flared or conical annulus section, a less bulbous aortic section, and the like, and a differently shaped transition section.

The expandable stent 102 of prosthetic heart valve 100 may be formed from biocompatible materials that are capable of self-expansion, such as, for example, shape memory alloys, such as the nickel-titanium alloy known as "Nitinol" or other suitable metals or polymers. Stent 102 extends from inflow or annulus end 130 to outflow or aortic end 132, and includes annulus section 140 adjacent inflow end 130, transition section 141 and aortic section 142 adjacent outflow end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at outflow end 132 thereof, retaining elements 168 being sized and shaped to cooperate with female retaining structures (not shown) provided on a deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one way valve by coapting with one another. As a prosthetic aortic valve, valve 100 has three leaflets 178. However, it will be appreciated that other prosthetic heart valves with which the sensors of the present disclosure may be used may have a greater or lesser number of leaflets.

Although cuff 176 is shown in FIG. 1 as being disposed on the lumenal or inner surface of annulus section 140, it is contemplated that cuff 176 may be disposed on the ablumenal or outer surface of annulus section 140 or may cover all or part of either or both of the lumenal and ablumenal surfaces. Both cuff 176 and leaflets 178 may be wholly or partly formed of any suitable biological material or polymer such as, for example, polyethylene terephthalate (PET), ultra-high-molecular-weight polyethylene (UHMWPE), or polytetrafluoroethylene (PTFE).

Leaflets 178 may be attached along lower belly portions to cells 162 of stent 102 and/or to cuff 176, with the commissure between adjacent leaflets 178 being attached to commissure features 166. As can be seen in FIG. 1, each commissure feature 166 may lay at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

In operation, the embodiment of the prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed inside the delivery device in the collapsed condition. The delivery device may be introduced into a patient using a transfemoral, transapical, transseptal or other percutaneous approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

Figure 2:
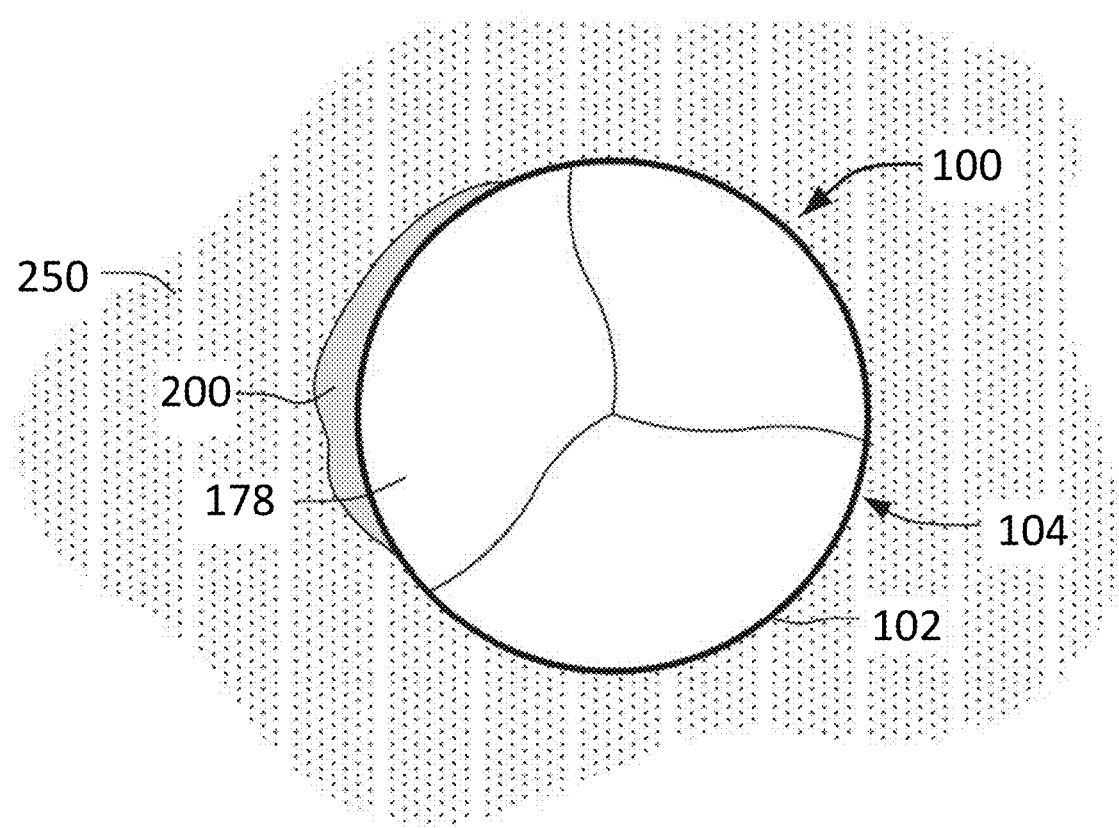
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of stent 102 has a substantially circular cross-section which is disposed within non-circular native valve annulus 250. At certain locations around the perimeter of heart valve 100, gaps 200, which may be crescent-shaped for example, form between the heart valve and native valve annulus 250. Blood flowing through these gaps and around leaflets 178 of valve assembly 104 can cause paravalvular leakage and other inefficiencies which reduce cardiac performance. Such improper fitment may result from suboptimal native valve annulus geometry due, for example, to calcification of native valve annulus 250 or to unresected native leaflets. Additionally, improper fitment may disrupt the proper coapting of leaflets 178, leading to aortic regurgitation (e.g., leakage or backflow of blood between the leaflets). In order to address concerns regarding leakage, such as paravalvular leakage or aortic regurgitation, sensors may be utilized to monitor the performance of a prosthetic heart valve.

Figure 3A:
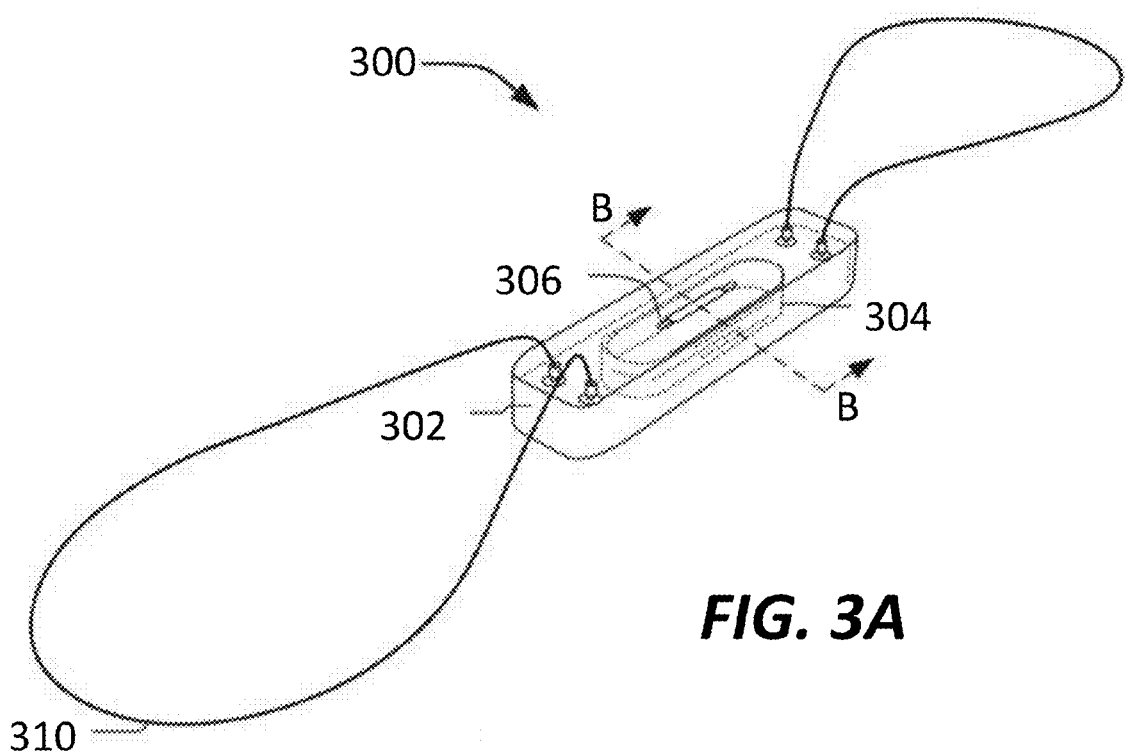
FIG. 3A is a perspective view of a wireless microelectromechanical (MEM) sensor.
Figure 3B:
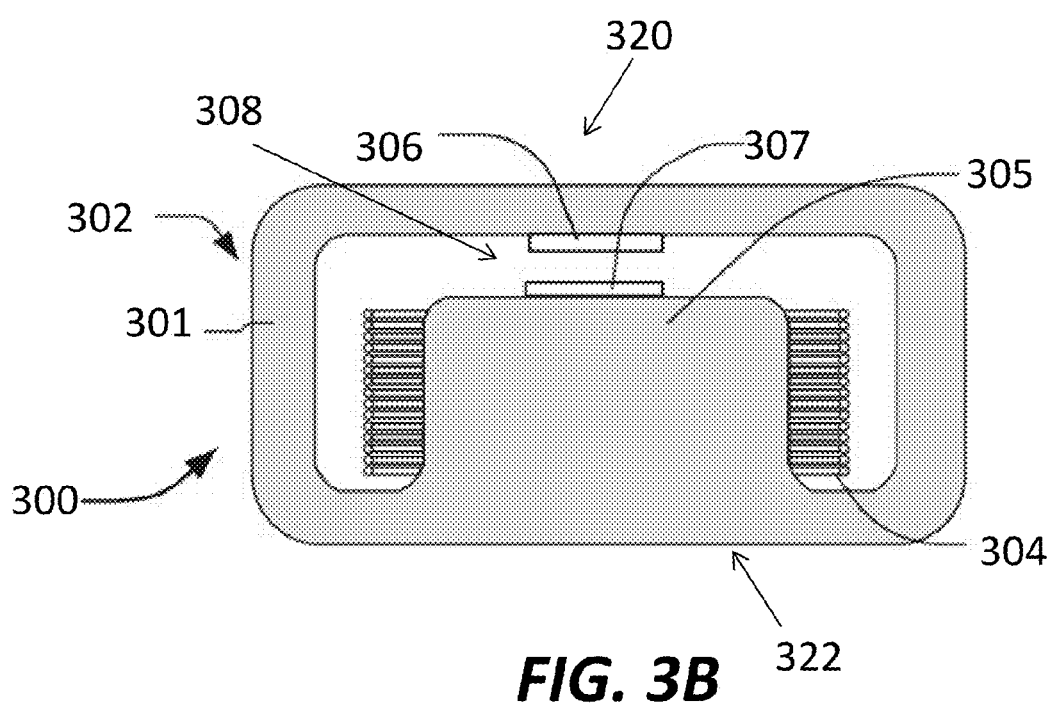
FIG. 3B is a cross-sectional view taken along line B-B of FIG. 3A.

FIGS. 3A and 3B illustrate one example of a microelectromechanical (MEM) sensor for diagnostic usage. Sensor 300 generally includes body 302 formed of a generally hollow fused silica housing 301. An elongated boss 305, also formed from fused silica, may project into the interior of housing 301 and may be formed integrally therewith. A plurality of electrically conductive windings may wrap around boss 305 to form an inductor coil 304. Capacitive plates 306 and 307 are separated by micrometer spacing, forming a variable capacitor 308. The exterior of housing 301 is coated with silicone, forming a hermetically sealed assembly that does not come in contact with blood.

Capacitive plate 306 is sensitive to pressure and experiences nanometer scale deflections due to changes in blood pressure acting on the sensor 300. In that regard, body 302 includes an active face 320 and a passive face 322, the measurements being taken at the active face. It should be understood that although sensor 300 includes active face 320 and passive face 322, other sensors may have other configurations, such as two active faces. The nanometer scale deflections of plate 306 result in a change in the resonant frequency of the circuit formed by the inductor coil 304 and the pressure-sensitive capacitor 308. The resonant frequency is given by the following equation:

$$\text{Resonant Frequency } f_R = \frac{1}{2\pi\sqrt{L \times C(p)}},$$

where L is the inductance of inductor coil 304 and C(p) is the capacitance of capacitor 308 which varies with pressure.

The sensor 300 can be electromagnetically coupled to a transmitting/receiving antenna (not shown). As a current is induced in the sensor 300, the sensor oscillates at the resonant frequency of the circuit formed by the inductor coil 304 and capacitor 308. This oscillation causes a change in the frequency spectrum of the transmitted signal. From this change, the bandwidth and resonant frequency of the particular sensor may be determined, and the corresponding blood pressure can then be calculated. Time-resolved blood pressure measurements can be correlated to flow using empirical relationships established in clinical literature. In one example, an external device may interrogate sensor 300 when in close proximity and may be placed near a location in which a patient is often located, such as in a pillow or in or near a bed. The external device may store data and have software for interpreting and/or displaying data, or may be used in conjunction with another device having software for interpreting and/or displaying data. Apparatus and methods for determining sensed data, such as blood pressure or data correlating to blood pressure, are discussed in greater detail in U.S. Pat. No. 6,855,115, the contents of which are hereby incorporated by reference herein.

As shown, sensor 300 includes optional Nitinol loops 310 extending from each end of body 302 to stabilize the sensor at an implant location. It will be appreciated that sensor 300 includes no additional leads, batteries, or active-fixation mechanisms. Sensor 300 is an externally modulated inductor-capacitor circuit, which is powered using radio frequency by the transmitting antenna. Additionally, sensor 300 may be relatively small (e.g., 3.5×2×15 mm). Other advantages of sensor 300 include its accuracy, durability, biocompatibility, and insensitivity to changes in body chemistry, temperature, or biology. Sensor 300 may optionally include one or more radiopaque components to aid in localization and imaging of the device.

Sensor 300 may be modified for various applications and tuned to selectively emphasize different parameters. For example, by varying the width of the windings of inductor coil 304, the number of turns and the size of a gap between adjacent upper and lower windings, the resonant frequency that the device operates at and the pressure sensitivity (i.e., the change in frequency as a result of deflection of capacitor plate 306) can be optimized for different applications. In general, the design allows for a very small gap between the capacitor plates (typically between about 0.5 and about 35 microns) that in turn provides a high degree of sensitivity while requiring only a minute movement of the capacitive plates 306 and 307 to sense pressure changes.

The thickness of sensor 300 may also be varied to alter mechanical properties. Thicker substrates for forming housing 301 are more durable for manufacturing. Thinner substrates allow for creation of thin pressure sensitive membranes for added sensitivity. In order to optimize both properties, sensor 300 may be manufactured using two complementary substrates of different thicknesses. For example, one side of sensor 300 may be constructed from a substrate having a thickness of about 200 microns. This provides the ability to develop and tune the sensor based on the operational environment in which the sensor 300 is implanted. In addition to changes to housing 301, other modifications may be made to the sensor depending on the application. For example, nitinol loops 310 may be omitted and replaced with suture holes for attaching the sensor to a support, and cantilevers or other structural members may be added. In some variations, the sensors may be powered by kinetic motion, the body's heat pump, glucose, electron flow, Quantum Dot Energy, and similar techniques.

Sensors 300 may be used to measure one or more types of physiological data including real time blood pressure; flow velocity (e.g., blood flow); apposition forces based on pressure changes due to interaction between two surfaces of the prosthetic valve; impingement forces, which are correlated to pressure changes caused by the interaction between a surface of the prosthetic device and native tissue; cardiac output; effective orifice area; pressure drop; temperature; motion; and aortic regurgitation. Sensor 300 provides time-resolved pressure data which may be correlated to the parameters of interest based on empirical correlations that have been presented in literature. In some examples, sensors 300 may function similar to piezo-electric strain gauges to directly measure a parameter. Other parameters may be indirectly calculated. One specific method of using sensors 300 to measure aortic regurgitation will be described in greater detail below with references to FIGS. 22A, 22B, and 23. Certain sensors and applications for sensors are described in greater detail in U.S. Patent Application No. 62/038,512 titled "Prosthetic Heart Devices Having Diagnostic Capabilities," the disclosure of which is hereby incorporated by reference herein.

It may be desirable to use one or more sensors 300 with different implantable devices, such as prosthetic heart valve 100. In particular, it may be desirable to be able to "bolt on" one or more sensors similar to sensor 300 to a pre-existing implantable device. However, different implantable devices may provide for different challenges in achieving easy and effective attachment of sensors. To that end, the housing 301 of sensor 300 may be modified to facilitate easy and effective attachment of the sensor to a pre-existing prosthetic heart valve 100. In embodiments of the disclosure described below, sensors coupled to implantable devices may remain in the body as long as desired, including for the life of the implantable device, so that blood pressure or other data may be taken as long as desired.

Figure 4A:
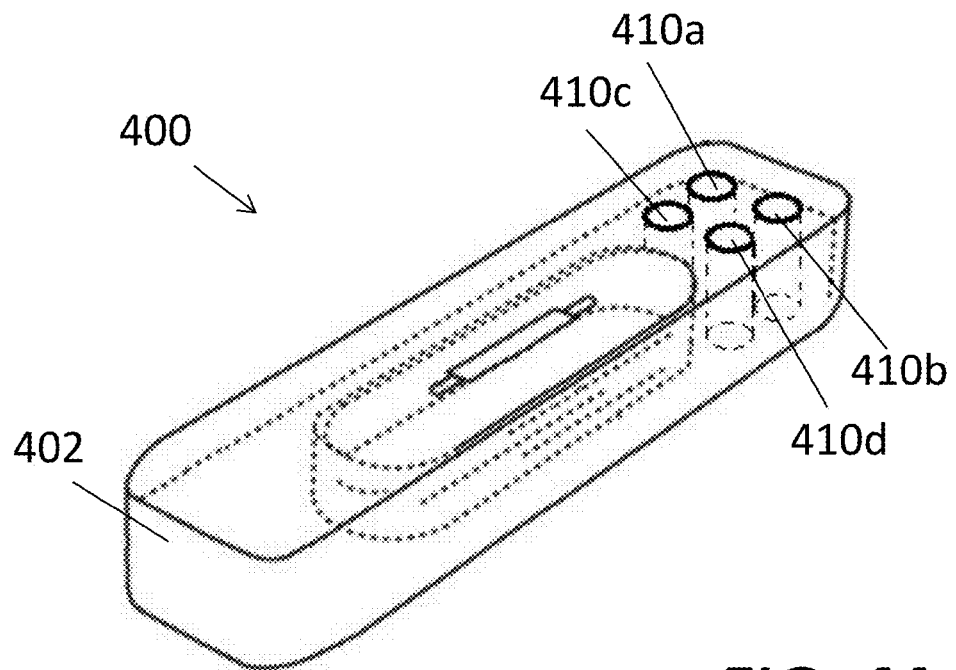
FIG. 4A is a perspective view of a MEM sensor according to one embodiment of the disclosure.
Figure 4B:
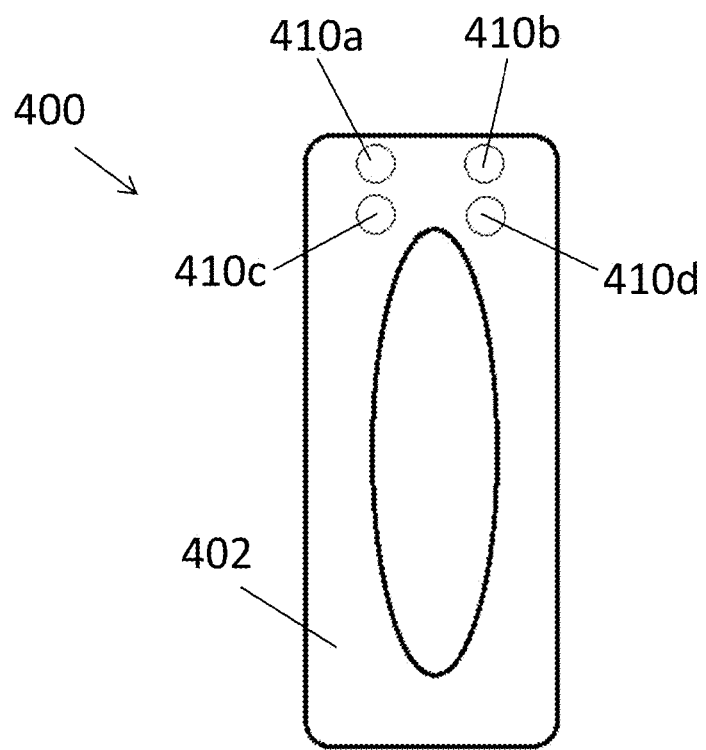
FIG. 4B is a plan view of the sensor of FIG. 4A.

One example of a modified MEM sensor 400 is shown in FIGS. 4A-B. Sensor 400 may be identical to sensor 300 with certain exceptions. For example, sensor 400 includes a different attachment mechanism than sensor 300. Instead of having the Nitinol loops 310 of sensor 300, the body 402 of sensor 400 may include a plurality of through holes or apertures extending from a front surface of the body to a rear surface of the body. In particular, body 402 may include four apertures 410*a-d* provided in a generally rectangular configuration at one end of body 402. In particular, apertures 410*a-d* may all be positioned a spaced longitudinal distance from functional components of sensor 400, such as any capacitive plates or windings within housing 402. Apertures 410*a* and 410*b* may be positioned along a first plane extending transversely through body 402, and apertures 410*c* and 410*d* may be positioned along a second plane extending transversely through body 402. Similarly, apertures 410*a* and 410*c* may be positioned along a first plane extending longitudinally through body 402, and apertures 410*b* and 410*d* may be positioned along a second plane extending longitudinally through body 402. Apertures 410*a-d* may be used to attach sensor 400 to a device, such as prosthetic heart valve 100, with the use of attachment means such as sutures, described in greater detail below. Sensor 400 may also be provided with rounded corners to minimize the chance that a sharp edge of sensor 400 damages any portion of the prosthetic heart valve (or other structure) to which it is attached.

Figure 4C:
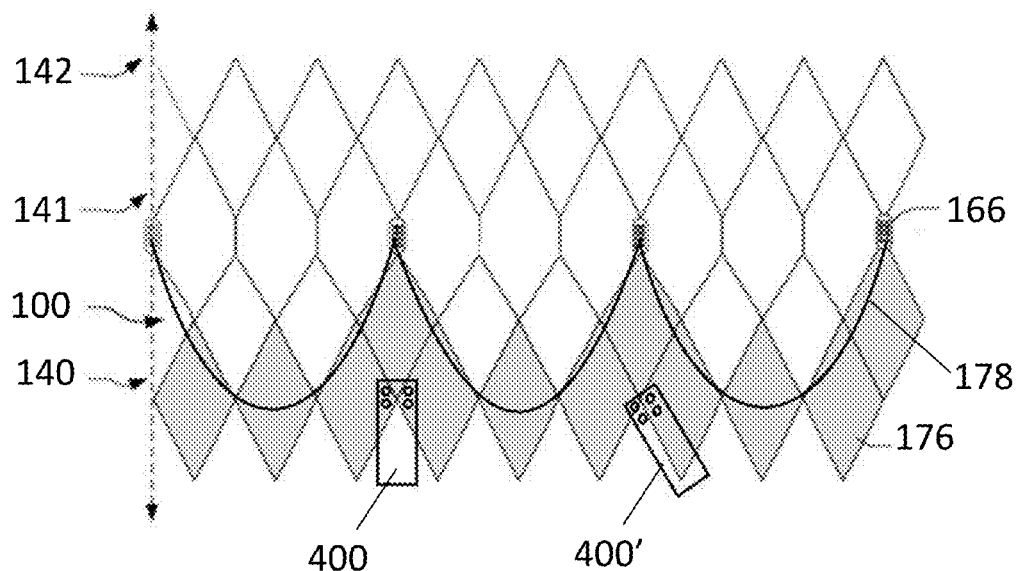
FIG. 4C is a highly schematic developed view of the prosthetic heart valve of FIG. 1 in an expanded condition with MEM sensors attached thereto.

FIG. 4C shows a developed view of a portion of heart valve 100 in an expanded condition with sensors 400 and 400' coupled to the inflow end of annulus section 140 in different configurations. First, it should be noted that sensors 400 and 400' are coupled to the lumenal surfaces of stent 102. This configuration helps ensure that sensors 400 and 400' do not interfere with proper sealing between the ablumenal surfaces of stent 102 and/or cuff 176 and the native valve annulus 250. Sensors 400 and 400' may be coupled to stent 102 and/or cuff 176, for example by suturing. Second, sensors 400 and 400' are preferably coupled to stent 102 at a point or points on the stent substantially longitudinally aligned with a commissure attachment feature 166 and near the inflow end. This configuration helps minimize any interference with the capability of leaflets 178 to open and close during normal operation. In other words, this position allows sensors 400 and 400' to be between and away from leaflets 178. In addition, this position is an area of relatively high flow, which may reduce the likelihood of thrombus formation or tissue ingrowth on sensors 400 and 400'. Third, sensors 400 and 400' are preferably coupled to stent 102 so that the passive face of body 402 faces the stent, while the active face of body 402 faces toward the longitudinal axis of prosthetic heart valve 100. This configuration helps ensure that the active face of body 402 is exposed to blood passing through the inflow end of prosthetic heart valve 100, which may allow more accurate measurements than if the active face of body 402 faced away from the longitudinal axis of prosthetic heart valve 100.

Figures 4D, 4E:
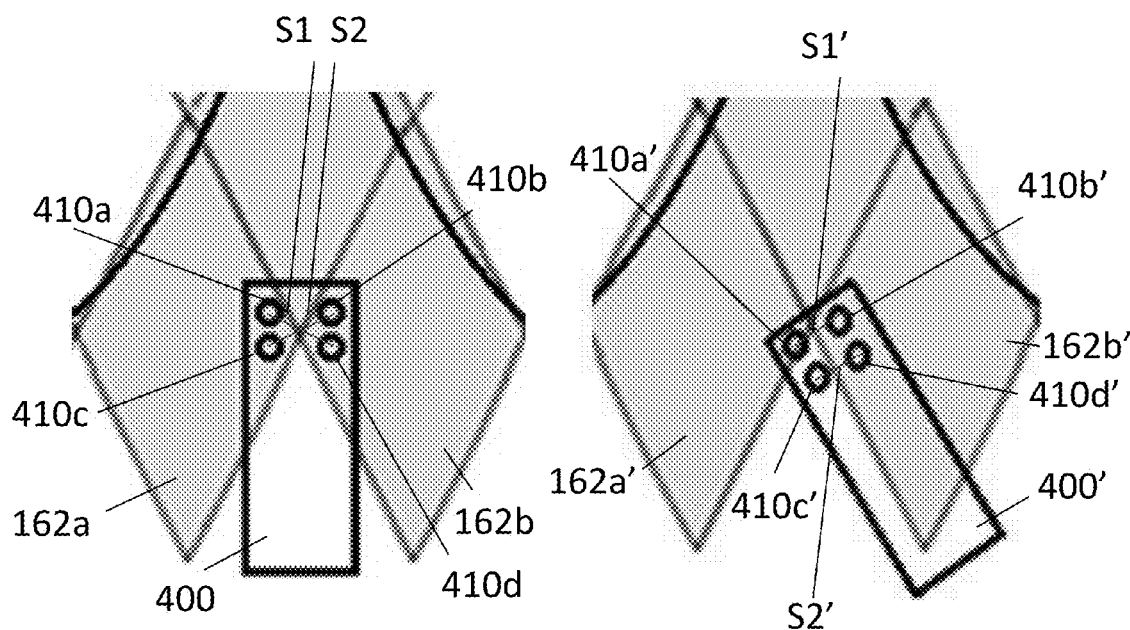
FIG. 4D is an enlarged partial view of one of the attached sensors of FIG. 4C.
FIG. 4E is an enlarged partial view of another of the attached sensors of FIG. 4C.
Figure 4F:
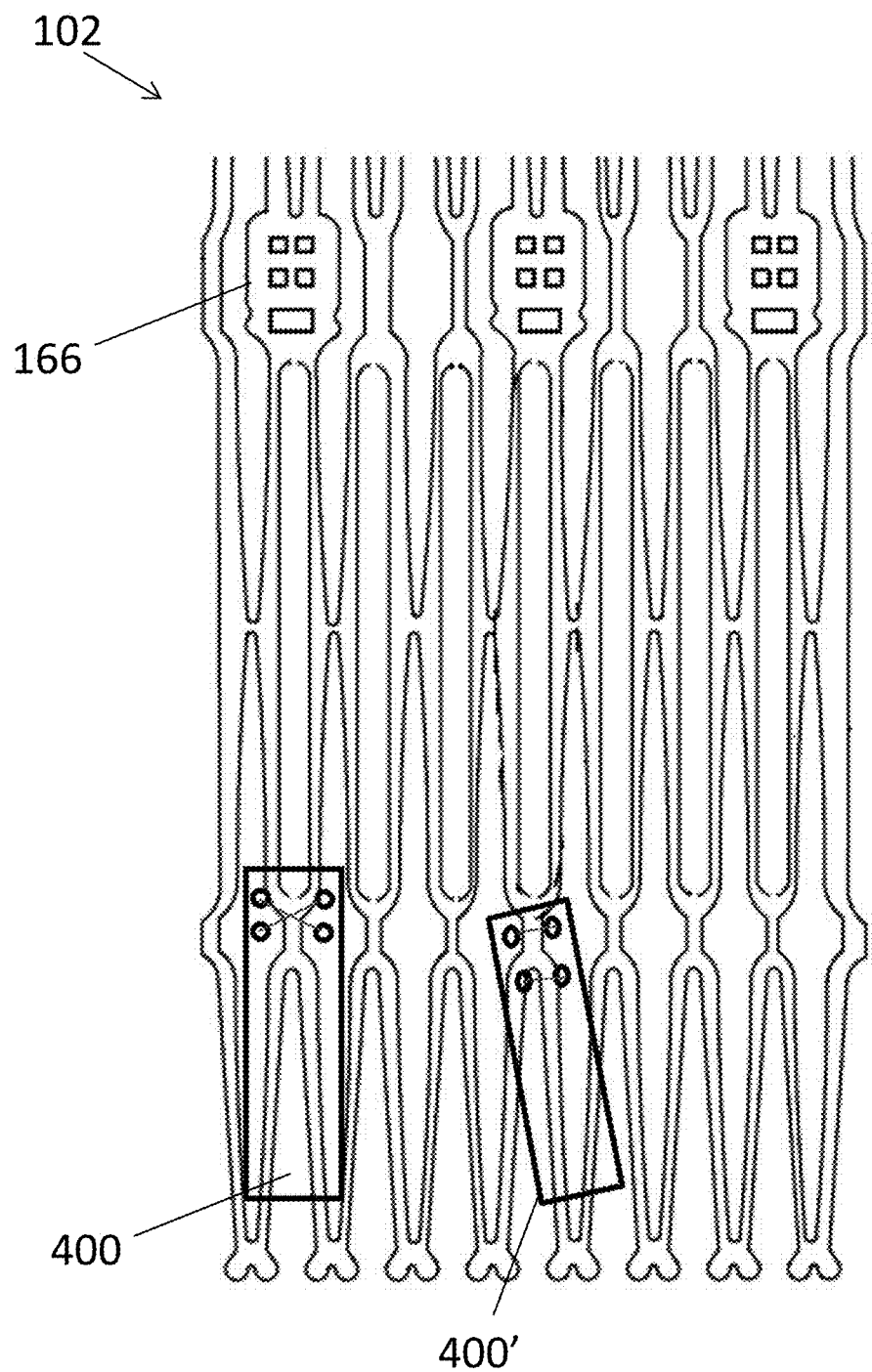
FIG. 4F is a highly schematic developed view of the stent of the prosthetic heart valve of FIG. 4C in a collapsed condition with MEM sensors attached thereto.

FIG. 4D shows in greater detail how sensor 400 is coupled to stent 102. In particular, apertures 410*a* and 410*c* are positioned on a first cell 162*a* while apertures 410*b* and 410*d* are positioned on a second cell 162*b* adjacent first cell 162*a*. A first suture S1 may extend diagonally from aperture 410*a* to aperture 410*d*, passing over the strut joint connecting cell 162*a* to cell 162*b*. Similarly, a second suture S2 may extend diagonally from aperture 410*b* to aperture 410*c*, also passing over the strut joint connecting cell 162*a* to cell 162*b*. If desired, additional sutures may extend between apertures 410*a* and 410*b*, and/or between apertures 410*c* and 410*d*, to provide additional security. With this configuration, the longitudinal axis of sensor 400 is substantially parallel to the longitudinal axis of prosthetic heart valve 100 in the expanded condition. Further, when prosthetic heart valve 100, including stent 102, is constricted to the collapsed configuration, for example during loading or resheathing, the longitudinal axis of sensor 400 remains substantially parallel to the longitudinal axis of prosthetic heart valve 100, as shown in FIG. 4F.

FIG. 4E shows in greater detail how sensor 400' is coupled to stent 102. In particular, aperture 410*a'* is positioned on a first cell 162*a'*, apertures 410*b'* and 410*d'* are positioned on a second cell 162*b'* adjacent first cell 162*a'*, and aperture 410*c'* is positioned in a space between cells 162*a'* and 162*b'*. A first suture S1' may extend from aperture 410*a'* to aperture 410*b'*, passing over the strut joint connecting cell 162*a'* to cell 162*b'*. A second suture S2' may extend from aperture 410*c'* to aperture 410*d'* across a single strut of second cell 162*b'*. If desired, additional sutures may extend between apertures 410*a'* and 410*d'*, and/or between apertures 410*b'* and 410*c'*, to provide additional security. With this configuration, the longitudinal axis of sensor 400' is angled with respect to the longitudinal axis of prosthetic heart valve 100 in the expanded condition. As prosthetic heart valve 100 is constricted to the collapsed configuration, suture S1' acts as a fulcrum and the longitudinal axis of sensor 400' rotates so that it becomes substantially parallel to the longitudinal axis of the prosthetic heart valve 100, as shown in FIG. 4F. With this configuration, sensor 400' is substantially longitudinally aligned with prosthetic heart valve 100 when it is in the collapsed condition, reducing potential interference between sensor 400' and prosthetic heart valve 100 during delivery and/or resheathing, and enabling prosthetic heart valve 100 to be collapsed more compactly.

Figure 5A:
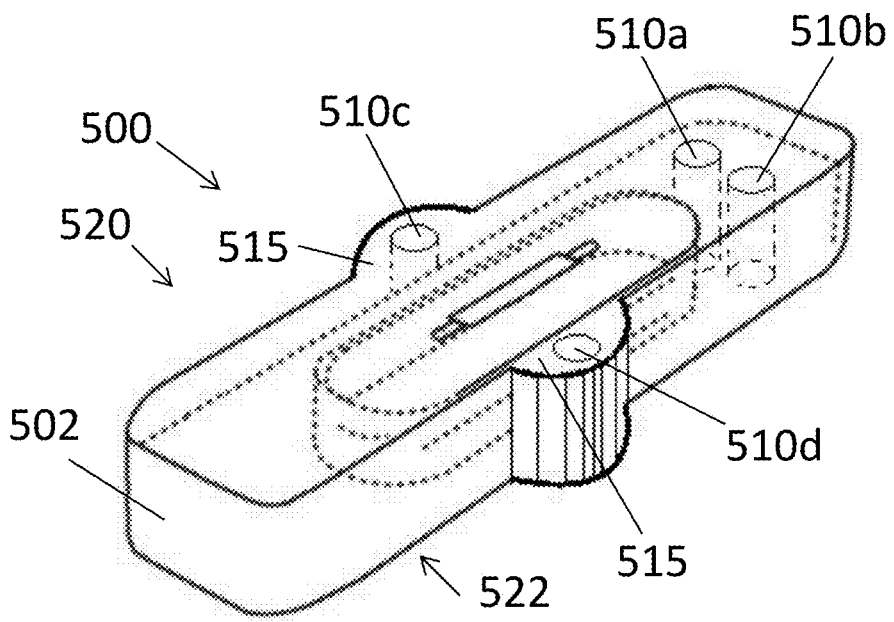
FIG. 5A is a perspective view of a MEM sensor according to another embodiment of the disclosure.
Figure 5B:
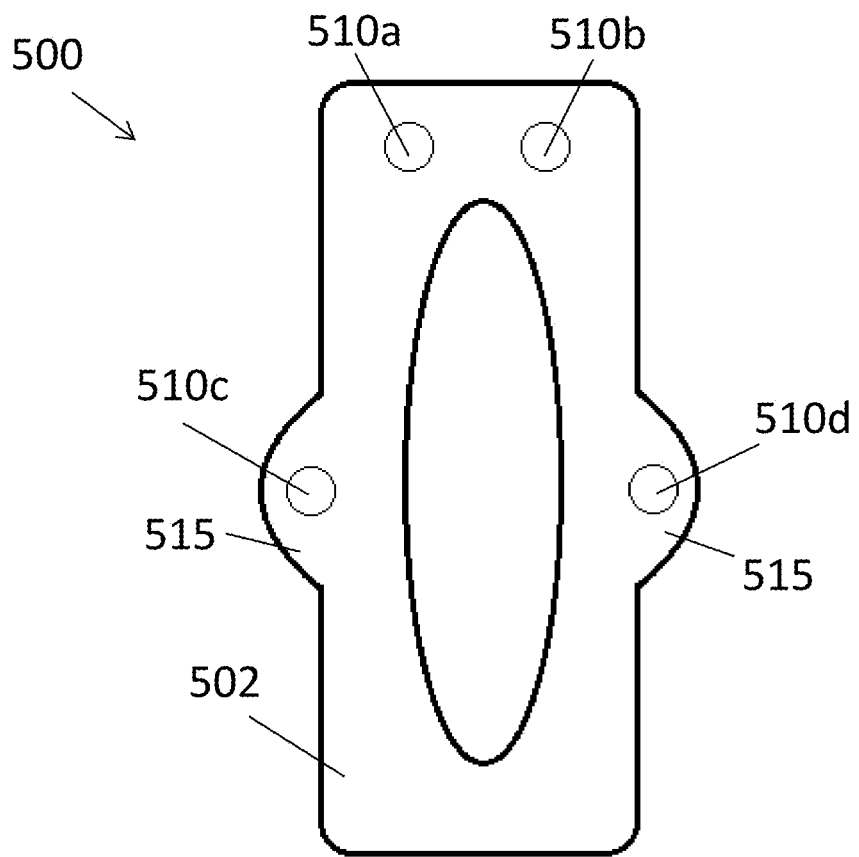
FIG. 5B is a top plan view of the sensor of FIG. 5A.

Another example of a modified MEM sensor 500 is shown in FIGS. 5A-B. Sensor 500 may be identical to sensors 300 and 400 in most respects. However, the body 502 of sensor 500 includes two projections 515. Each projection 515 has a first face extending from and coplanar with the active face 520 of housing 502, and a second face extending from and coplanar with the passive face 522 of housing 502. The surface extending between the first face and the second face of each projection 515 is preferably atraumatic, for example by being rounded. Further, each projection 515 is preferably positioned at a mid-point of the length of body 502. Sensor 500 may have a plurality of through holes or apertures extending from a front surface of body 502 to a rear surface of the body, similar to sensor 400. In particular, body 502 may include two apertures 510*a-b* positioned along a first plane extending transversely through a first end portion of the body. Two additional apertures 510*c-d* may be included in body 502, with one aperture 510*c* positioned in one projection 515 and the other aperture 510*d* positioned in the other projection 515.

Figure 5C:
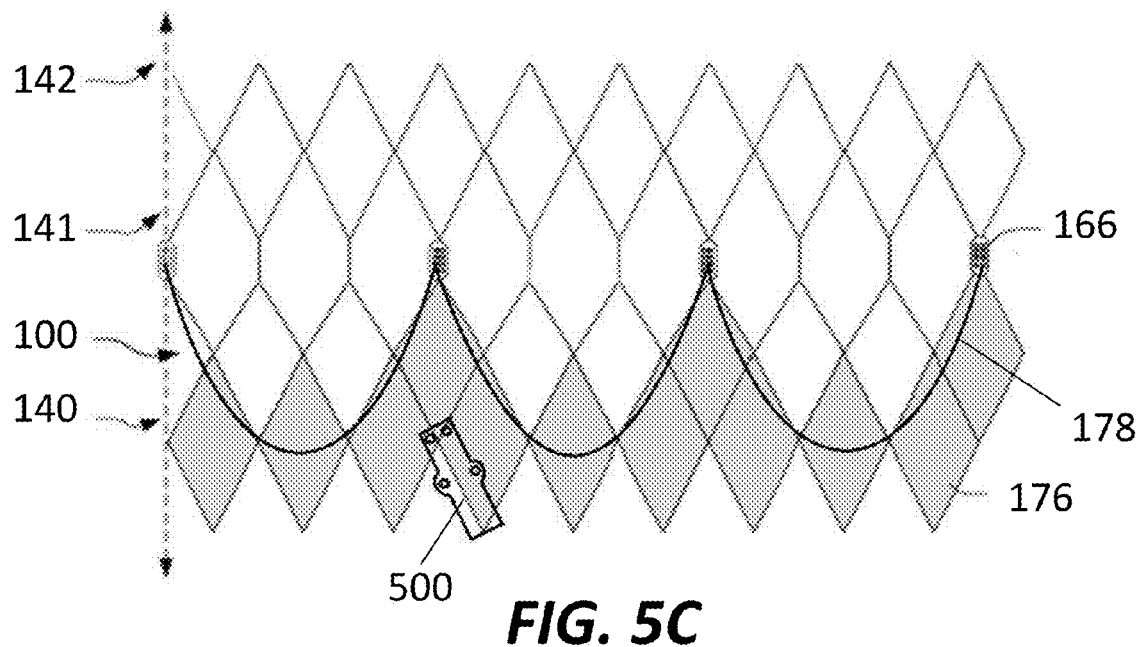
FIG. 5C is a highly schematic developed view of the prosthetic heart valve of FIG. 1 in an expanded condition with the sensor of FIG. 5A attached thereto.

FIG. 5C shows a developed view of a portion of heart valve 100 in an expanded condition with sensor 500 coupled to the inflow end of annulus section 140. The general considerations regarding attachment location described in connection with sensor 400 apply with equal force to sensor 500. For example, sensor 500 is preferably coupled to the lumenal surface of stent 102 at a point substantially longitudinally aligned with a commissure attachment feature 166 and near the inflow end.

Figure 5D:
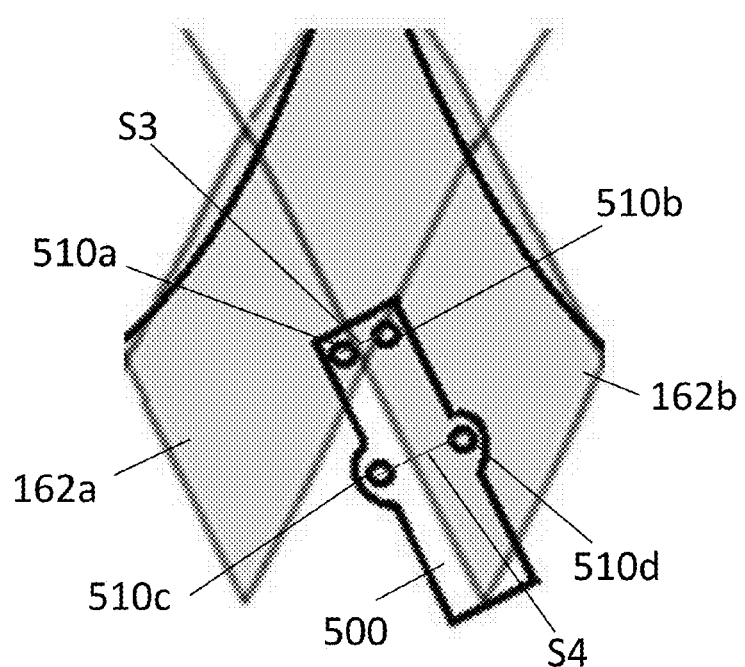
FIG. 5D is an enlarged partial view of the attached sensor of FIG. 5C.

FIG. 5D shows in greater detail how sensor 500 is coupled to stent 102. In particular, aperture 510*a* is positioned on a first cell 162*a* while aperture 510*b* is positioned on a second cell 162*b* adjacent first cell 162*a*. A first suture S3 may extend from aperture 510*a* to aperture 510*b*, passing over the strut joint connecting cell 162a to cell 162b. Aperture 510c is positioned in a space between cells 162a and 162b, while aperture 510d is positioned on second cell 162b. A second suture S4 may extend from aperture 510c to aperture 510d across a single strut 160 of cell 162b. Since apertures 510c-510d are positioned at a longitudinal midpoint of sensor 500, those apertures are aligned along the length of sensor 500 with at least some active components of the sensor, such as capacitive plates or inductor coils. Thus, suture S4 preferably extends from aperture 510c to 510d only along passive face 522 of housing 502, which may help suture S4 avoid interference with measurements taken by sensor 500. With the configuration described above, the longitudinal axis of sensor 500 is angled with respect to the longitudinal axis of prosthetic heart valve 100 in the expanded condition. As prosthetic heart valve 100 is constricted to the collapsed configuration, suture S3 acts as a fulcrum and the longitudinal axis of sensor 500 rotates so that it is substantially parallel to the longitudinal axis of the prosthetic heart valve 100. During this rotation, suture S4 slides along the strut 160 of cell 162b extending between apertures 510c and 510d. Similar to the configuration of sensor 400' described above, sensor 500 is substantially longitudinally aligned with prosthetic heart valve 100 when it is in the collapsed condition, reducing potential interference between sensor 500 and prosthetic heart valve 100 that would prevent the prosthetic heart valve from collapsing to a compact size during delivery and/or resheathing.

Figure 6B:
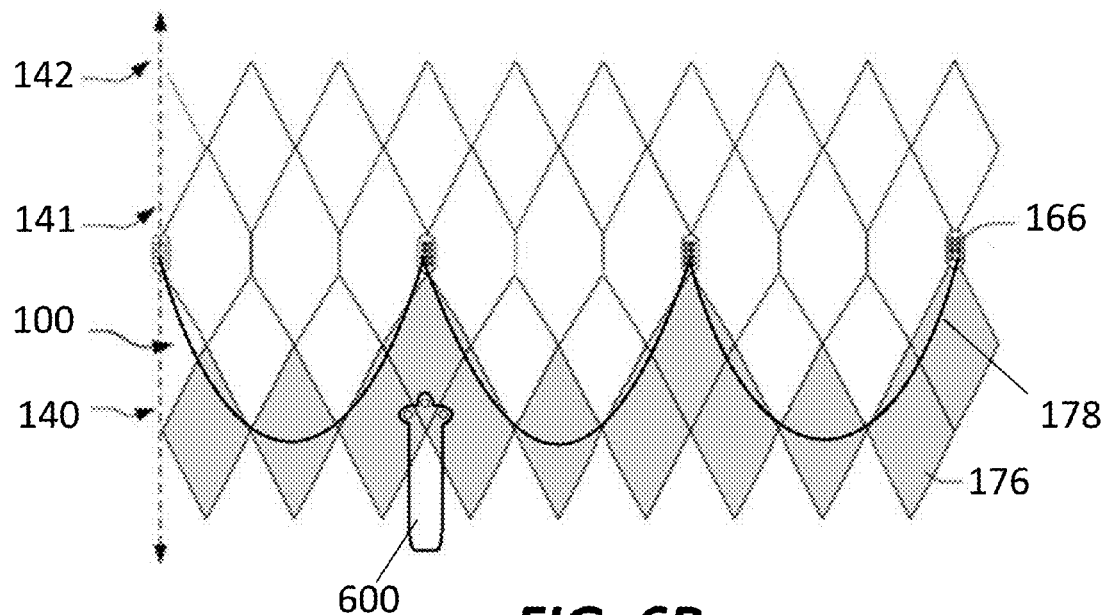
FIG. 6B is a highly schematic developed view of the prosthetic heart valve of FIG. 1 in an expanded condition with the sensor of FIG. 6A attached thereto.
Figure 6A:
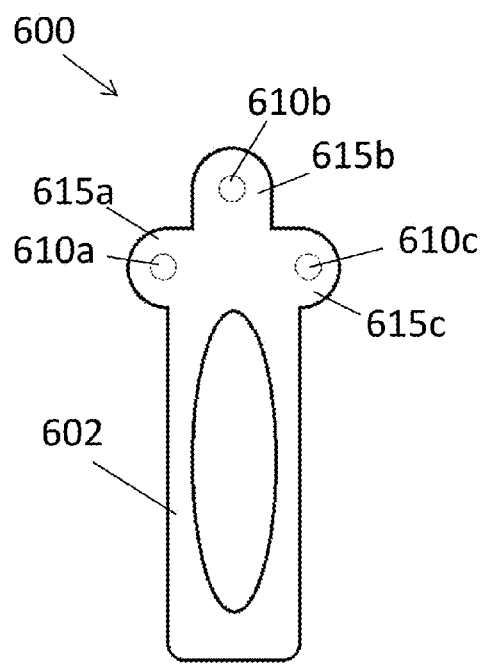
FIG. 6A is a top plan view of a MEM sensor according to a further embodiment of the disclosure.

Yet another example of a modified MEM sensor 600 is shown in FIG. 6A. Sensor 600 may be identical to sensors 300 and 400 in most respects. However, the body 602 of sensor 600 includes three projections 615a-c extending from one end of body 602. In particular, projection 615b extends along the longitudinal axis of body 602, while two projections 615a and 615c extend transverse to the longitudinal axis of body 602. Similar to projections 515 of sensor 500, projections 615a-c of sensor 600 are preferably rounded to minimize interference between the projections 615a-c and the prosthetic valve 100 to which the sensor is attached. Sensor 600 has a plurality of apertures 610a-c extending from a front surface of the projections 615a-c to a rear surface of the projections, respectively.

Figure 6C:
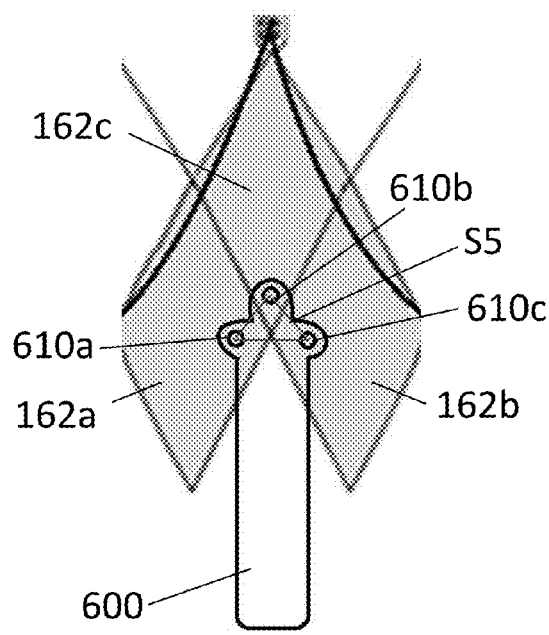
FIG. 6C is an enlarged partial view of the attached sensor of FIG. 6B.

FIG. 6B shows a developed view of a portion of heart valve 100 in an expanded condition with sensor 600 coupled to the inflow end of annulus section 140. The general considerations regarding attachment location described in connection with sensor 400 apply with equal force to sensor 600. FIG. 6C shows in greater detail how sensor 600 is coupled to stent 102. In particular, aperture 610a is positioned on a first cell 162a in a first annular row, and aperture 610c is positioned on a second cell 162b in the first annular row adjacent first cell 162a. Aperture 610b is positioned on a third cell 162c, the third cell being in a second longitudinal row of cells and being formed in part by struts 160 forming cells 162a and 162b. A first suture S5 may extend from aperture 610a to aperture 610b, from aperture 610b to aperture 610c, and from aperture 610c back to aperture 610a, forming a triangle. Suture S5 couples sensor 600 to prosthetic heart valve 100 at the struts 160 forming the joint between cells 162a-c. With the configuration described above, the longitudinal axis of sensor 600 is substantially parallel to the longitudinal axis of prosthetic heart valve 100 in both the expanded and collapsed conditions. Although suture S5 is described as a single suture, it should be understood that multiple separate sutures may be used to achieve the same attachment configuration.

While FIGS. 4A-6C show various MEM sensors and their attachment to the inflow end of prosthetic heart valve 100, FIGS. 7-10C show additional variations of MEM sensors and their attachment to the outflow end of prosthetic heart valve 100.

Figure 7:
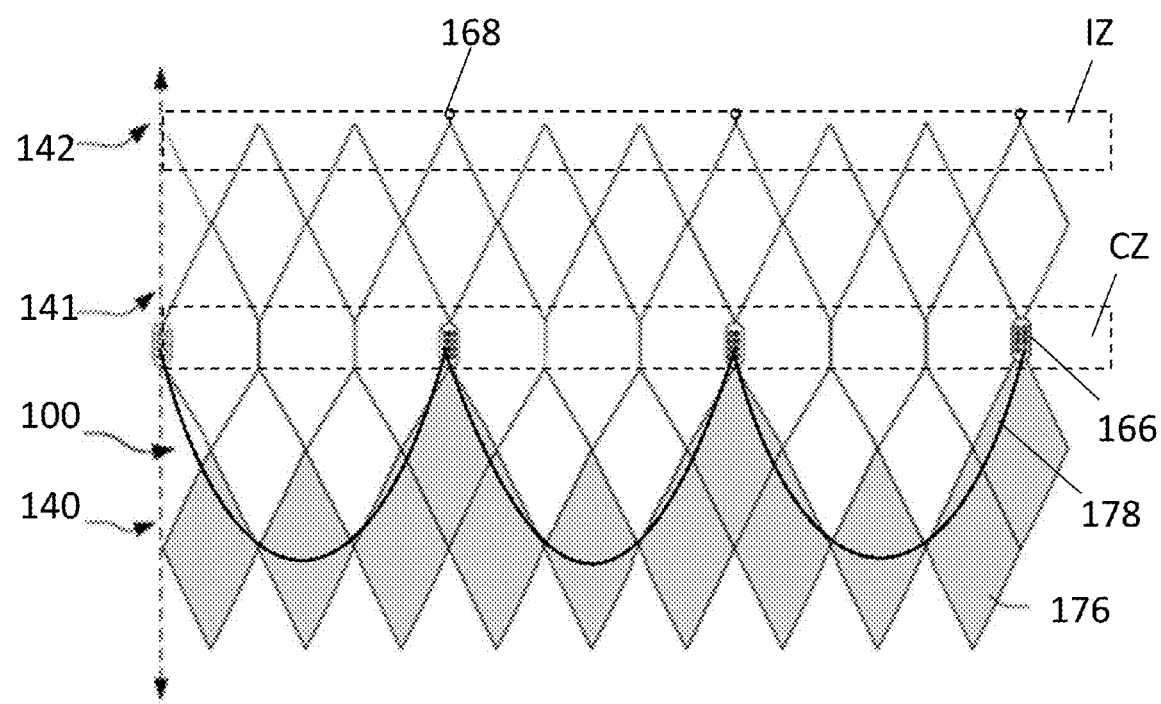
FIG. 7 is a highly schematic developed view of the prosthetic heart valve of FIG. 1 in an expanded condition showing outflow attachment locations for a MEM sensor.

FIG. 7 is a highly schematic developed view of prosthetic heart valve 100 in the expanded condition. When attaching a sensor to the outflow end of prosthetic heart valve 100, the sensor is preferably positioned so that it does not interfere with normal operation of the prosthetic heart valve. In particular, two outflow zones which may be less suitable for sensor attachment are shown in FIG. 7. As described above in connection with FIG. 1, one or more retaining elements 168 may be positioned at the outflow end 132 of stent 102. Because retaining elements 168 are configured to mate with corresponding retaining structures on a deployment device (not shown), it is preferable that sensors not be positioned in an interlock zone IZ, which extends around the circumference of stent 102 at retaining elements 168 and positions just proximal of the retaining elements. If sensors were positioned in interlock zone IZ, the ability of retaining elements 168 to properly engage the retaining structures on the deployment device might be hindered. Similarly, it is preferable that sensors be positioned so that they do not interfere with the proper functioning of leaflets 178. To avoid such interference, it is preferable that sensors not be positioned in a commissure zone CZ, which extends around the circumference of stent 102 for the length of commissure features 166. The commissure zone CZ may extend an additional distance toward the inflow and outflow ends of stent 102 to provide an additional buffer zone to keep sensors clear of leaflets 178. The interlock zone IZ and commissure zone CZ may also have a relatively large amount of curvature, and have additional thickness due to other components attached to stent 102 in these locations, particularly with stent 102 is in a crimped or loaded condition. If a sensor attached to stent 102 is not substantially rigid, the sensor may be crushed or otherwise damage, particularly during loading, if coupled in the interlock or commissure zones. In one example, when stent 102 is in the expanded condition, the longitudinal distance between commissure features 166 and retaining elements 168 is about 20 mm, with a desirable position for sensor attachment being in about the center 10 mm of this about 20 mm distance.

A further example of a modified MEM sensor 700 is shown in FIG. 8A. Sensor 700 may be identical to sensor 500 in most respects. For example, the body 702 of sensor 700 includes two projections 715, each projection 715 having a first face extending from and coplanar with an active face of housing 702, and a second face extending from and coplanar with the passive face of housing 702. The surface extending between the first face and the second face of each projection 715 is preferably atraumatic, for example by being rounded. Further, each projection 715 is preferably positioned at a mid-point of the length of body 702. Sensor 700 has first and second apertures 710a, 710b, one extending through each projection 715 so as to be positioned along a plane extending transversely through body 702.

FIG. 8B shows a developed view of a portion of heart valve 100 in an expanded condition with sensor 700 coupled to an outflow portion of aortic section 142. As described in connection with FIG. 7, sensor 700 is preferably attached to stent 102 between interlock zone IZ and commissure zone CZ so that sensor 700 does not interfere with the coaptation of the leaflets or with the coupling of retaining elements 168 of stent 102 to a delivery device. In addition, similar to the sensors positioned on the inflow portion of stent 102, sensor 700 is preferably coupled to the lumenal surface of stent 102. This configuration may help, for example, avoid interference between sensors 700 and portions of the native anatomy that would otherwise contact stent 102. [In addition, this position is an area of relatively high flow, which may reduce the likelihood of thrombus formation or tissue ingrowth on sensor 700. Further, similar to the sensors described above, sensor 700 is preferably coupled to stent 102 so that the passive face of body 702 faces the stent, while the active face of body 702 faces toward the longitudinal axis of prosthetic heart valve 100. This configuration helps ensure that the active face of body 702 is exposed to blood passing through the outflow end of prosthetic heart valve 100, which may allow more accurate measurements than if the active face of body 702 faced away from the longitudinal axis of prosthetic heart valve 100.

FIG. 8C shows in greater detail how sensor 700 is coupled to stent 102. In particular, aperture 710a is positioned on a first cell 162d while aperture 710b is positioned on a second cell 162e adjacent first cell 162d. A suture S6 may extend from aperture 710a to aperture 710b, passing over the strut joint connecting cell 162d to cell 162e. Preferably, suture S6 couples sensor 700 to stent 102 such that the suture does not cross the active face of sensor 700, for the same reasons described in connection with sensor 500. It should be understood that although this configuration is preferable, in other configurations sutures may cross the active face of a sensor. With the configuration described above, the longitudinal axis of sensor 700 may be angled or parallel with respect to the longitudinal axis of prosthetic heart valve 100 in the expanded condition. If sensor 700 is positioned at an angle, as prosthetic heart valve 100 is constricted to the collapsed configuration, sensor 700 may rotate so that it is substantially parallel to the longitudinal axis of the prosthetic heart valve 100, reducing potential interference between sensor 700 and prosthetic heart valve 100 during delivery and/or resheathing, and enabling the prosthetic heart valve to collapse to a compact size.

FIG. 9A illustrates another example of a modified MEM sensor 800. Sensor 800 may be identical to sensor 700, with the exception that the body 802 of sensor 800 includes rounded projections 815 that each has two apertures, rather than one. In particular, two apertures 810a, 810c are positioned on a first projection 815, and two apertures 810b, 810d are positioned on a second projection 815. FIG. 9B shows a developed view of a portion of heart valve 100 in an expanded condition with sensor 800 coupled to an outflow portion of aortic section 142. The considerations described above with respect to the placement of sensor 700 on stent 102 apply with equal force to the placement of sensor 800 on stent 102.

FIG. 9C shows in greater detail how sensor 800 is coupled to stent 102. In particular, aperture 810a is positioned on a first cell 162d in a first annular row of cells, apertures 810b and 810d are positioned on a second cell 162e adjacent first cell 162d in the first annular row of cells, and aperture 810c is positioned in a third cell 162f adjacent first and second cells 162d-e and in a second annular row of cells adjacent the first annular row of cells. A first suture S7 may extend from aperture 810a to aperture 810b, passing over the strut joint connecting cell 162d to cell 162e. A second suture S8 may extend across a single strut 160 shared between second cell 162e and third cell 162f. If desired, additional sutures may extend between apertures 810a and 810d, and/or between apertures 810b and 810c, to provide additional security. With this configuration, similar to the configuration described in connection with sensor 400', the longitudinal axis of sensor 800 is angled with respect to the longitudinal axis of prosthetic heart valve 100 in the expanded condition. As prosthetic heart valve 100 is constricted to the collapsed configuration, suture S7 acts as a fulcrum and the longitudinal axis of sensor 800 rotates so that it becomes substantially parallel to the longitudinal axis of the prosthetic heart valve 100. With this configuration, sensor 800 is substantially longitudinally aligned with prosthetic heart valve 100 when it is in the collapsed condition, reducing potential interference between sensor 800 and prosthetic heart valve 100 that would prevent the prosthetic heart valve from collapsing to a compact size during delivery and/or resheathing. This alignment may further avoid unwanted mechanical strain on the sensor and structures connecting the sensor to the valve as well as undesirable strain effects on the stent and/or valve itself. In an alternate configuration, sutures S7 and S8 may be centered across the intersection of cells 162d and 162e. In other words, in this alternate configuration, apertures 810a and 810c may both be positioned in cell 162 and apertures 810b and 810d may be positioned in cell 162e, with sutures S7 and S8 both extending from cell 162d to cell 162e.

FIG. 10A illustrates another example of a modified sensor 900. Sensor 900 may be similar to sensor 800 in that it includes four apertures 910a-d. However, the apertures 910a-d are positioned on four rounded projections 915a-d, respectively. In particular, projections 915a-b and apertures 910a-b are located at a first lengthwise position toward one end of body 902, while projections 915c-d and apertures 910c-d are located at a second lengthwise position toward the opposite end of body 902, and spaced apart in the lengthwise direction from projections 915a-b. FIG. 10B shows a developed view of a portion of heart valve 100 in an expanded condition with sensor 900 coupled to an outflow portion of aortic section 142. The considerations described above with respect to the placement of sensor 700 on stent 102 apply with equal force to the placement of sensor 900 on stent 102.

FIG. 10C shows in greater detail how sensor 900 is coupled to stent 102. In particular, aperture 910a is positioned on a first cell 162d in a first annular row of cells, and aperture 910b is positioned in a space between first cell 162d and a second cell 162e adjacent the first cell in the first annular row. Aperture 910c is positioned in a third cell 162f adjacent first and second cells 162d-e and in a second annular row of cells adjacent the first annular row of cells, and aperture 910d is positioned within second cell 162e. A first suture S9 may extend from aperture 910a to aperture 910b, passing over a single strut 160 of first cell 162d. A second suture S10 may extend from aperture 910c to aperture 910d, passing over a single strut 160 shared by second cell 162e and third cell 162f. With this configuration, sensor 900 is able to rotate as prosthetic heart valve 100 is collapsed so that the sensor is substantially aligned with the longitudinal axis of the prosthetic heart valve when stent 102 is in the collapsed condition. The configuration of sutures S9 and S10 each extending across a single strut also permits sensor 900 to slide a distance toward or away from the outflow end of stent 102.

A further embodiment of a MEM sensor 1000 is illustrated in FIG. 11A. Sensor 1000 may be similar in structure to sensor 300 with certain exceptions. For example, sensor 1000 includes a body 1002 with a rounded main body 1004 housing the sensor components, and two fingers 1006a and 1006b extending from the main body along the length thereof. Fingers 1006a and 1006b may have a similar outer contour as the outer contour of main body 1004, with the outer contours of the main body 1004 and fingers 1006*a* and 1006*b* together forming a portion of a circle or oval, or a substantially circular or ovular shape. Fingers 1006*a* and 1006*b* in combination with a portion of main body 1004 together form a partially open channel 1010 extending along the length of body 1002. As shown in FIG. 11B, channel 1010 may have a width D1. The open side of channel 1010, generally defined by the space between the inner terminal portions of fingers 1006*a* and 1006*b*, may have a width D2. Width D2 is preferably smaller than width D1, so that sensor 1000 may be snap fit onto another device, as described in greater detail below.

Sensor 1000 may be coupled, for example by snap fitting, onto any suitable device. For example, as shown in FIG. 11C, sensor 1000 may be coupled to a strut 160 of stent 102. Strut 160 preferably has a width that is substantially equal to or smaller than the width D1 of channel 1010, but greater than the width D2 of the open side of the channel. With this configuration, once sensor 1000 is coupled to strut 160, the width of strut 160 keeps sensor 1000 coupled to stent 102 because strut 160 is too wide to easily pass through the open side of channel 1010. In order to snap or otherwise couple sensor 1000 to strut 160, a user may orient sensor 1000 so that a smaller dimension of strut 160 passes through the open side of channel 1010, after which the sensor may be rotated to a position similar to that shown in FIG. 11C. Strut 160 has a thickness dimension that is smaller than its width dimension, and substantially equal to or smaller than the width D2 of the open side of channel 1010. Additionally or alternatively, strut 160 may be somewhat compressible and/or fingers 1006*a* and 1006*b* of body 1002 may splay away from one another upon the application of force to help snap fit sensor 1000 onto strut 160. Although the connection of sensor 1000 to a strut 160 of stent 102 has been described, it should be understood that sensor 1000 may be coupled to any device with a suitable attachment structure, such as other portions of stent 102, other or similar structures on different types of heart valves, or other implantable devices altogether.

Figure 11D:
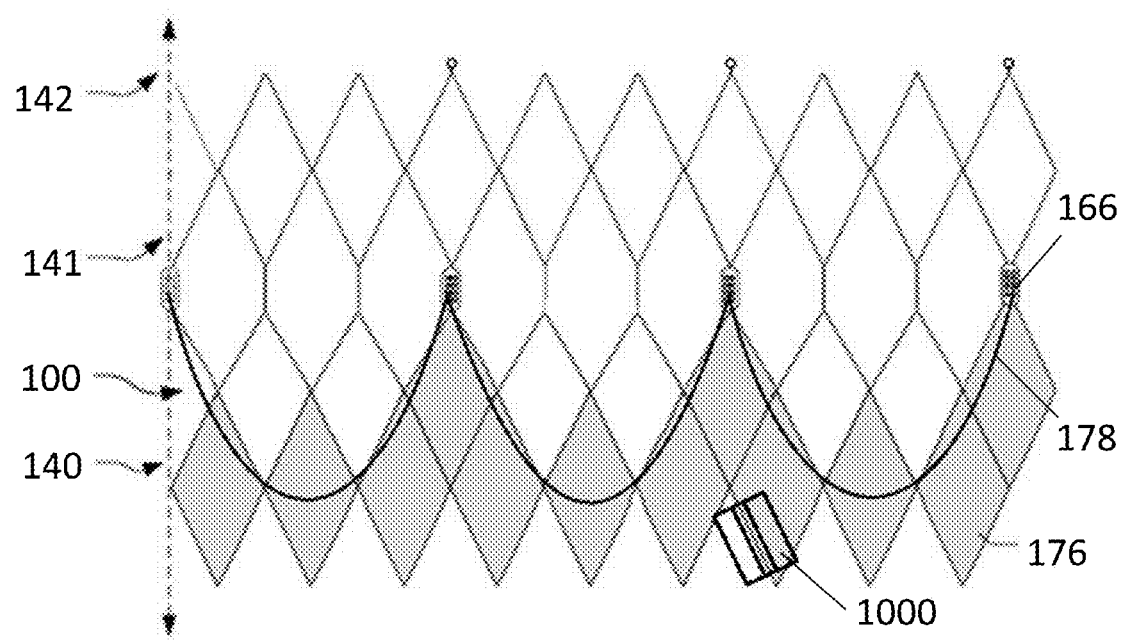
FIG. 11D is a highly schematic developed view of the prosthetic heart valve of FIG. 1 in an expanded condition with the sensor of FIG. 11A attached thereto.
Figure 11E:
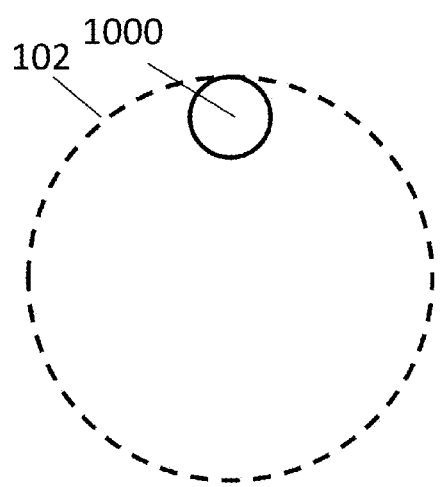
FIG. 11E is a highly schematic end view of the sensor of FIG. 11A attached to the prosthetic heart valve of FIG. 1 in the expanded condition.
Figure 11F:
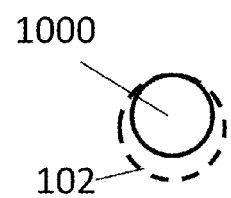
FIG. 11F is a highly schematic end view of the sensor of FIG. 11A attached to the prosthetic heart valve of FIG. 1 in the collapsed condition.

FIG. 11D shows a developed view of a portion of heart valve 100 in an expanded condition with sensor 1000 coupled to the inflow end of annulus section 140. The general considerations of the attachment of sensor 1000 to the inflow end of annulus section 140 may be the same as described in connection with sensor 400. It should also be noted that, although not explicitly shown, sensor 1000 may also be coupled to the outflow portion of aortic section 142, or at any other desirable position with a suitable structure available. As noted above, main body 1004 and fingers 1006*a* and 1006*b* of sensor 1000 have an outer surface that may be substantially circular. As stent 102 transitions from the expanded condition (FIG. 11E) to the collapsed condition (FIG. 11F), the inner diameter of stent 102 approaches the outer diameter of sensor 1000. With this configuration, when stent 102 is in the crimped or collapsed condition, there is enough clearance to minimize or avoid interference with and/or damage to the valve components of prosthetic heart valve 100 by sensor 1000.

Another embodiment of a MEM sensor 1100 is illustrated FIGS. 12A-B. Sensor 1100 may be generally similar in structure to sensor 300, with sensor 1100 having a body 1102 with the sensor components housed therein. However, instead of Nitinol loops, a ring clip 1105 may be coupled to the rear of body 1102. As shown in the side view of sensor 1100 in FIG. 12A, the ring clip 1105 may include a first arcuate arm 1115*a* and a second arcuate arm 1115*b*, the terminal ends of the two arms defining a gap 1116. First arm 1115*a* and second arm 1115*b* may be formed as a unitary piece or separate pieces. Preferably, first arm 1115*a* and second arm 1115*b* are both formed of a shape memory material, such as Nitinol. As shown in the rear view of sensor 1100 in FIG. 12B, the arms 1115*a* and 1115*b* may be positioned substantially parallel to the longitudinal axis of sensor 1100, and toward one end of housing 1102, although other positions may be suitable. This configuration may enable sensor 1100 to be clipped onto one or more struts 160 of stent 102 without the need for sutures.

As shown in FIG. 12C, prosthetic heart valve 100 may include runners 161 which are struts 160 that connect a bottom vertex of one cell 162 with a top vertex of a vertically adjacent cell 162. Sensor 1100 may be coupled to stent 102 by hooking first arm 1115*a* over the bottom vertex of one cell 162, and hooking second arm 1115*b* under the top vertex of a vertically adjacent cell, as shown in FIG. 12D. The shape-memory property of the first arm 1115*a* and second arm 1115*b* allow the arms to be moved away from one another to increase the size of gap 1116, and after hooking the arms 1115*a* and 1115*b* over and under the cell vertices, the arms may return to their pre-set shape, decreasing the size of gap 1116, and providing a secure connection to stent 102. In this assembled position, sensor 1100 is aligned over runner 161. Since the length of runner 161 does not change as prosthetic heart valve 100 moves between the collapsed and expanded conditions sensor 1100 can stay assembled to stent 102 as the prosthetic heart valve is delivered into a patient and deployed. It should be understood that arms 1115*a* and 1115*b* may be shaped, sized, or positioned in a manner other than described above, including on different faces of body 1102, to attach sensor 1100 to other locations on stent 102, for example to other struts 160 or to commissure a attachment feature 166. Also, although one set of two arms 1115*a* and 1115*b* is illustrated, it should be understood that additional sets of arms may be provided on sensor 1100. The sets of arms may be sized and positioned to match a desired connecting position on stent 102 or on other types of stents of other prosthetic heart valves.

Another embodiment of a MEM sensor 1200 is illustrated FIGS. 13A-B. Sensor 1200 may be generally identical to sensor 1100, with sensor 1200 having a modified connecting mechanism. For example, instead of a ring clip 1105, sensor 1200 includes a one-arm clip 1215 extending from a rear surface of body 1202. As shown in the top view of sensor 1200 in FIG. 13A, clip 1215 includes a single arm 1218 with a first terminal end coupled to the rear surface of body 1202. Arm 1218 may have a first portion extending away from body 1202, a second portion extending parallel to body 1202, and a third portion returning toward body 1202 so that a second terminal end of arm 1218 is spaced from the rear surface of body 1202, forming a gap 1216. Although illustrated as rectangular, clip 1215 may take other shapes and may be, for example, rounded. Preferably, clip 1215 is formed of a shape-memory material, such as Nitinol. As shown in the rear view of sensor 1200 in FIG. 13B, the clip 1215 may be positioned substantially orthogonal to the longitudinal axis of body 1202, and toward one end thereof, with the center of clip 1215 being substantially aligned with the longitudinal axis of body 1202, although other positions may be suitable. This configuration may enable sensor 1200 to be clipped onto one or more struts of stent 102 without the need for sutures.

As shown in FIG. 13C, sensor 1200 may be coupled to stent 102 by hooking the arm 1218 of clip 1215 around two struts 160 forming the upper vertex of a cell 162, although other connection locations may be suitable. The shape-memory property of clip 1215 allows the arm 1218 to be moved away from the rear surface of body 1202 to increase the size of gap 2116, and after hooking arm 1218 around struts 160, the arm may return to its pre-set shape, decreasing the size of gap 1216, and providing a secure connection to stent 102. It should be understood that arm 1218 may be shaped, sized, or positioned in a manner other than described above, including on different faces of body 1202, to attach sensor 1200 to other locations on stent 102, for example to other struts 160 or to a commissure attachment feature 166. Also, although one arm 1218 is illustrated, it should be understood that additional arms may be provided on sensor 1200. The arm or arms may be sized and positioned to match a desired connecting position on stent 102 or on other types of stents of other prosthetic heart valves.

Figure 14B:
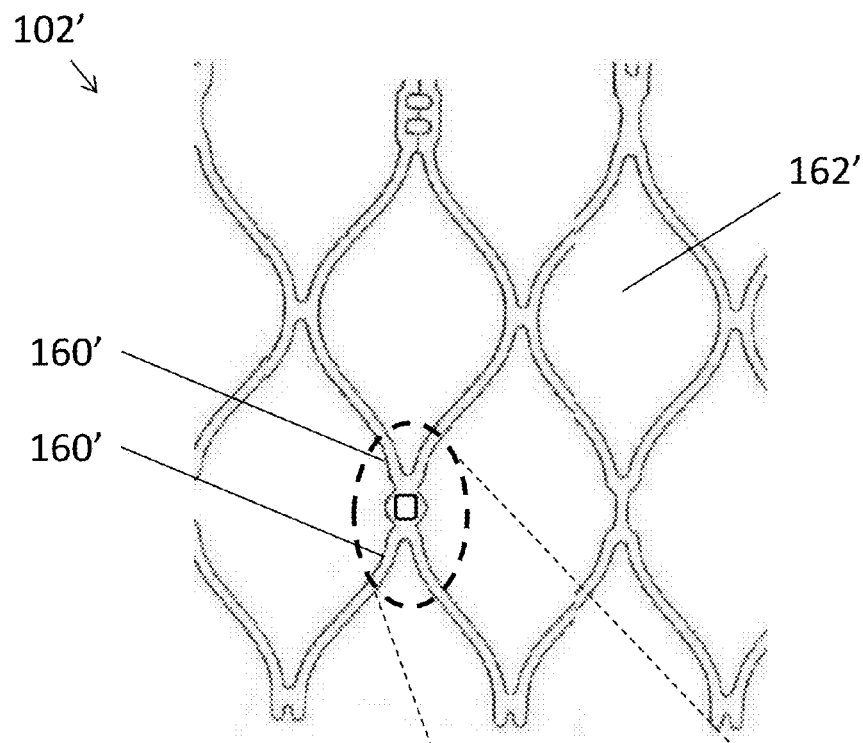
FIG. 14B is a highly schematic developed view of a portion of a modified stent for a prosthetic heart valve in an expanded condition.
Figure 14A:
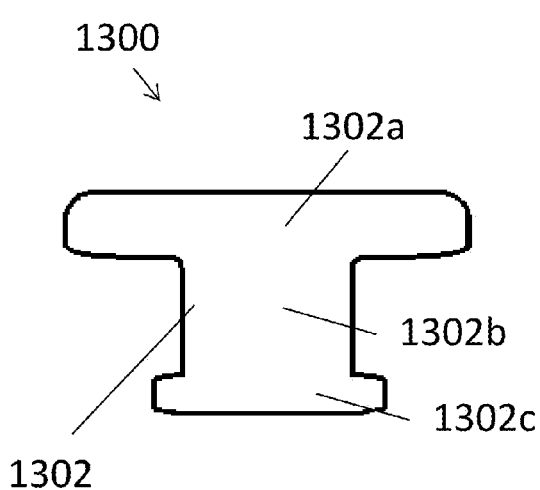
FIG. 14A is an end view of a MEM sensor according to a further embodiment of the disclosure.

FIG. 14A illustrates a top view of a further embodiment of a MEM sensor 1300. Sensor 1300 may be substantially similar to sensor 300, with sensor 1300 lacking Nitinol loops and having a modified geometry of body 1302. In particular, body 1302 may include a front section 1302a, a middle section 1302b, and a rear section 1302c. Front section 1302a may have a width larger than middle and rear sections 1302b and 1302c. Rear section 1302c may have a width larger than middle section 1302b. The centers of front, middle, and rear sections 1302a-c may be substantially aligned so that front section 1302a and rear section 1302c each has two portions extending laterally from middle section 1302b. As is described in greater detail below, the laterally extending portions of front and rear sections 1302a and 1302c facilitate a snap fit connection of sensor 1300 to another device.

Figure 14C:
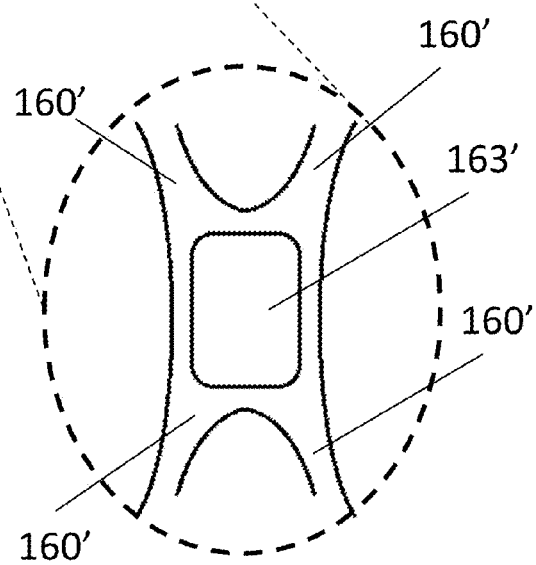
FIG. 14C is an enlarged partial view of the modified stent of FIG. 14B.
Figure 14D:
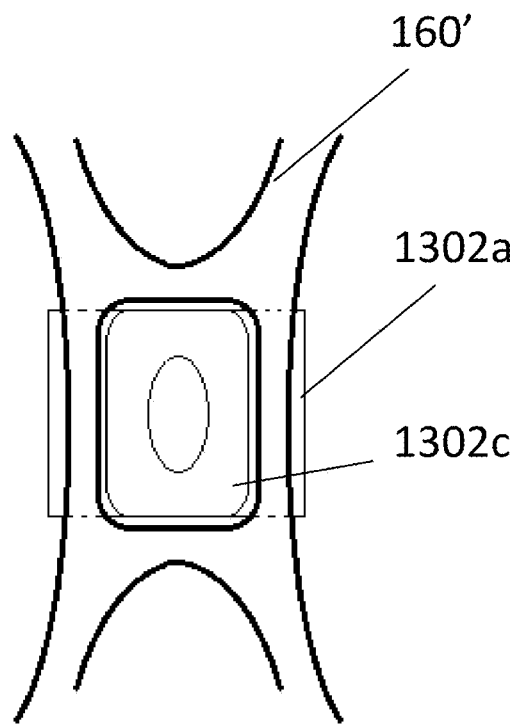
FIG. 14D is an enlarged partial view of the sensor of FIG. 14A attached to the stent of FIG. 14B.
Figure 14E:
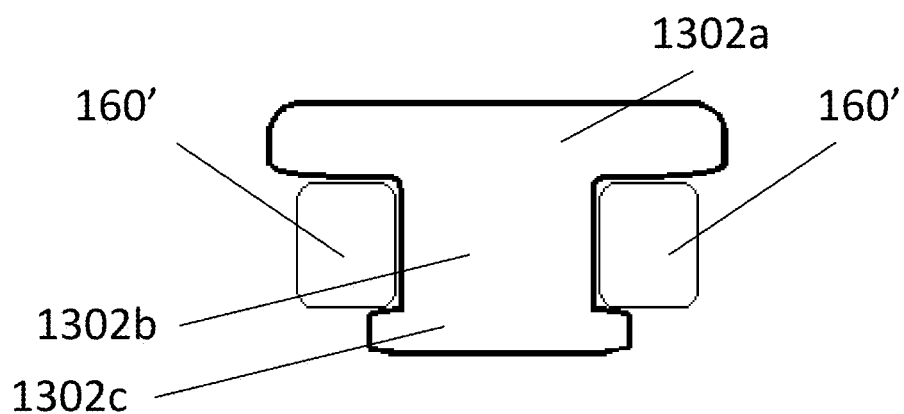
FIG. 14E is an enlarged partial cross-section of the sensor of FIG. 14A attached to the stent of FIG. 14B.

FIG. 14B illustrates a portion of a stent 102' for use with a prosthetic heart valve in a developed view, as if cut longitudinally and laid out flat. Stent 102' is substantially identical to stent 102 with minor variations. In particular, struts 160' form cells 162', and at least one set of struts 160' may define an aperture 163'. Aperture 163', as illustrated in FIGS. 14B-C, may be formed in a runner, which may be the region where two struts 160' of a first cell 162' meet two struts 160' of an adjacent cell 162' in the same annular row. The width of aperture 163' may be smaller than that of front and rear sections 1302a and 1302c of the body 1302 of sensor 1300, and substantially similar to the width of the middle section 1302b of sensor 1300. With this configuration, as shown in FIGS. 14D-E, sensor 1300 may be snap fit into aperture 163' of stent 102. Because stent 102' may be made of Nitinol or another material having flexibility, rear section 1302c of sensor 1300 may be forced through aperture 163' until the laterally extending portions of rear section 1302c pass fully through aperture 163', as best seen in FIG. 14E. The laterally extending portions of front section 1302a are too large to pass through aperture 163', leading to a secure snap fit connection of sensor 1300 to stent 102'. The laterally extending portions of rear section 1302c of sensor 1300 may be formed of a material with some flexibility as well so that these portions may collapse to a small degree to help them pass through aperture 163' when coupling the sensor 1300 to stent 102'.

Figure 15A:
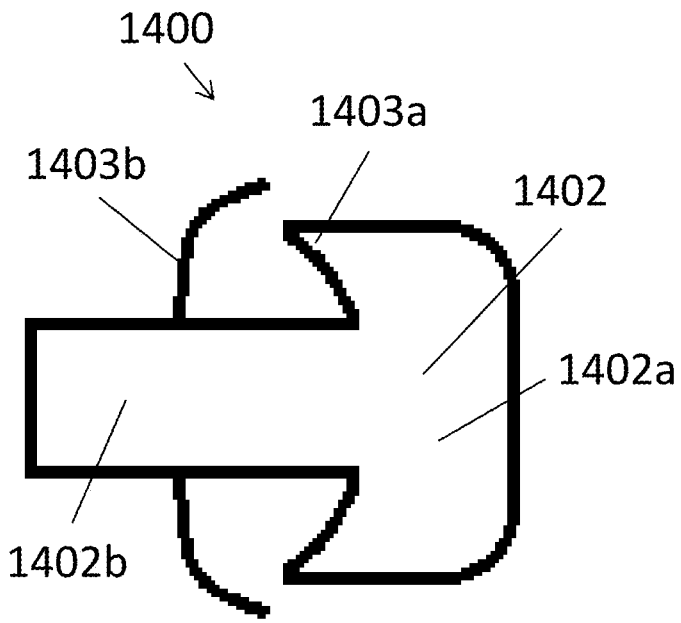
FIG. 15A is an end view of a MEM sensor according to another embodiment of the disclosure.
Figure 15B:
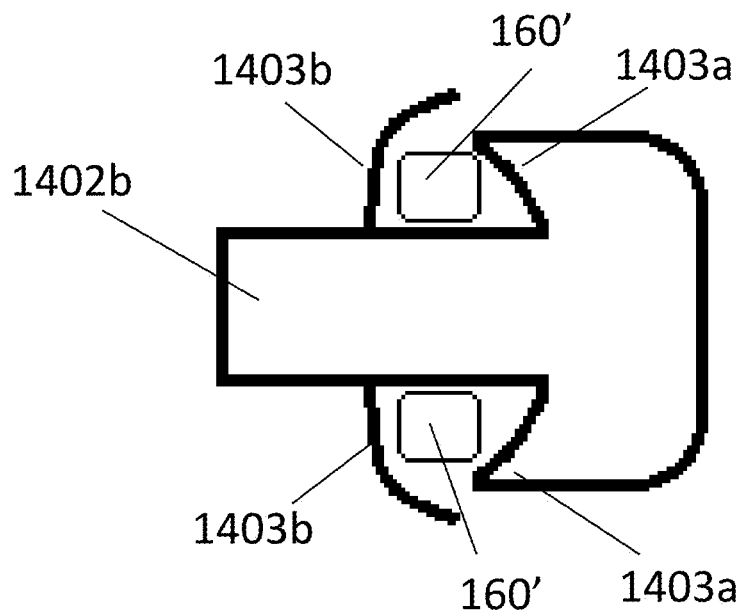
FIG. 15B is an enlarged partial cross-section of the sensor of FIG. 15A attached to the modified stent of FIG. 14B.

FIG. 15A illustrates a top view of a MEM sensor 1400 according to still a further embodiment of the disclosure. Sensor 1400 may be substantially similar to sensor 300, without Nitinol loops and with a different geometry. For example, body 1402 of stent 1400 may include a relatively large head 1402a with a relatively narrow shank 1402b projecting away from head 1402a. Head 1402a may form hooks 1403a where shank 1402a transitions to shank 1402b. A pair of flexible arms 1403b may extend laterally from shank 1402b at a spaced distance from head 1402a. Flexible arms 1403b may be formed of a shape-memory material such as Nitinol, and may be shape set so that in the absence of an externally applied force, arms 1403b curve or hook toward head 1402a. As a result, in the absence of an externally applied force, open slots may be formed between each arm 1403b and each adjacent hook 1403a of head 1402a.

As best shown in FIG. 15C, shank 1402b may be slightly narrower than aperture 163' so that it may be inserted through aperture 163', and front portion 1402a may be substantially wider than aperture 163' so that it cannot pass through aperture 163'. Because arms 1403b are flexible, they may bend out of the way as shank 1402b passes through the aperture 163', the arms 1403b also passing through aperture 163'. Once the arms 1403b fully pass through aperture 163', they may return to their pre-set shape and hook over portions of the struts 160' forming aperture 163'. Similarly, hooks 1403a may hook over those same struts 160' from the other side. This arrangement enables sensor 1400 to be quickly and securely coupled to stent 102' via aperture 163'.

Another embodiment of a MEM sensor 1500 is shown in FIGS. 16A-B. Sensor 1500 may be substantially identical to sensor 300, with the exception that sensor 1500 does not have Nitinol loops but rather a different securement mechanism. For example, a protrusion 1505 may extend from the rear face of body 1502 to facilitate coupling of sensor 1500 to an aperture 163' of stent 102'. Protrusion 1505 may include a first member 1510a having a semi-circular shaft 1515a that projects from the rear face of body 1502 and terminates in an enlarged semi-circular head 1516a, and a second member 1510b having a semi-circular shaft (not shown) that projects from the rear face of body 1502 and terminates in an enlarged semi-circular head 1516b. The first and second members 1510a, 1510b may be mirror images of one another, and may be spaced apart to define gap 1518 therebetween.

To couple sensor 1500 to stent 102', a user need only push the heads 1516a and 1516b of protrusion 1505 through aperture 163'. Preferably, heads 1516a and 1516b have a chamfered surface such that the act of pushing members 1510a and 1510b through aperture 163' forces the heads toward one another, closing gap 1518. As should be understood, heads 1516a and 1516b, together with gap 1518 therebetween, may collectively have a width that is greater than the width of aperture 163'. However, when gap 1518 is closed, heads 1516a and 1516b together have a smaller width that is capable of passing through aperture 163'. The shafts of members 1510a and 1510b, together with gap 1518 therebetween, have a width that is smaller than the width of aperture 163', regardless of whether gap 1518 is open or closed. When sensor 1500 is assembled to stent 102', once the heads 1516a and 1516b clear the struts 160' forming aperture 163', there is no longer a compressive force closing gap 1518, the heads 1516a and 1516b return toward their initial positions, and gap 1518 returns toward its initial size. The chamfered surfaces of heads 1516a and 1516b are directional so that pushing members 1510a and 1510b through aperture 163' tends to force the members together, while pulling the members in the opposite direction does not produce the same effect. This configuration helps ensure that sensor 1500 may be easily and securely coupled to stent 102' via aperture 163', but unintentional disconnection of the sensor 1500 from the stent is difficult.

Though previous examples have illustrated sensors disposed on collapsible heart valves, other applications of the sensors are possible. For example, FIG. 17A illustrates a MEM sensor 1600 similar to sensor 300 with a few variations. Sensor 1600 includes a body 1602 substantially similar to body 302 but without the Nitinol loops of sensor 300. Rather, a rear side of body 1602 includes four arms 1615a-d extending therefrom. Each arm 1615a-d preferably is made of a shape-memory material, such as Nitinol. In addition, each arm 1615a-d preferably has a pre-set L shape in which, in the absence of an externally applied force, each arm first extends orthogonally away from the rear surface of body 1602 and then in a direction parallel to the rear surface of body 1602. As shown in FIG. 17A, each arm 1615a-d extends substantially at a right angle to the adjacent arms, although other configurations may be suitable. This configuration may make sensor 1600 particularly suitable for attachment to a stented surgical valve 2000, shown in FIG. 17B.

Valve 2000 generally includes a fatigue-resistant metallic frame 2010, shown in FIG. 17C (sometimes also referred to as a stent), having three upstanding posts 2012. As best seen in FIGS. 17C-D, each post 2012 may have an aperture 2014 at its distal tip. Pericardial tissue or other suitable material may cover stent 2010 and may be supported by posts 2012 to form the leaflets 2030 of a one-way valve. A sewing cuff 2020 may be attached in the form of a ring around the proximal periphery of stent 2010. Prior to attaching cuff 2020, leaflets 2030 and other material to stent 2010, sensor 1600 may be coupled to stent 2010 as follows. The arms 1615a-d may each be deformed so that they all extend substantially orthogonally from the rear surface of body 1602. In this deformed condition, the arms 1615a-d are inserted through aperture 2014 of post 2012. The portions of arms 1615a-d that are shape set to extend substantially parallel to the rear surface of body 1602 take their set shape once those portions clear aperture 2014. With this configuration, the arms 1615a-d effectively hook onto post 2012, securing sensor 1600 in place. It should be understood that more or less than four arms 1615a-d may be suitable for this application, and the arms may extend in directions other than those shown. Further, sensor 1600 may be coupled to valve 2000 after the cuff 2020, leaflets 2030 and/or other material have been applied to stent 2010, for example by making a small hole in the material in alignment with an aperture 2014 to which the sensor is to be secured. Still further, although sensor 1600 may be suitable for coupling to a surgical valve, sensor 1600 may be effectively coupled to any device having an appropriately sized aperture through which arms 1615a-d may pass.

Figure 17E:
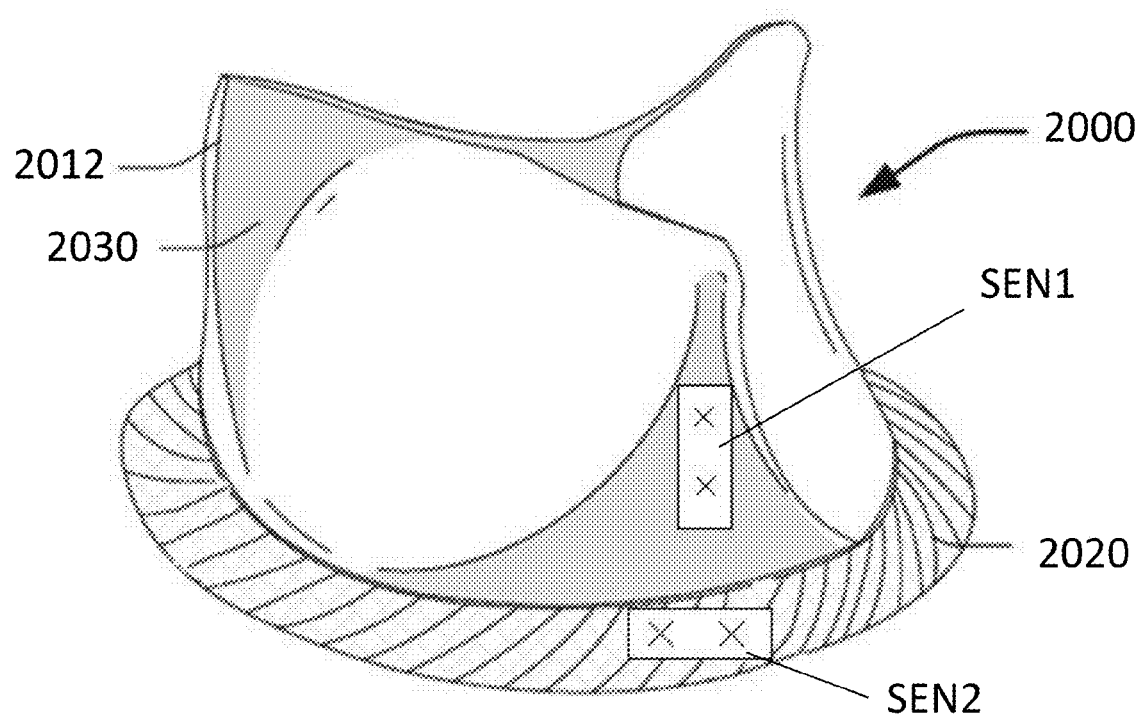
FIG. 17E is a perspective view of the surgical prosthetic heart valve of FIG. 17B with sensors according to FIG. 17A attached thereto.

Sensors having configurations other than that described directly above may be attached to surgical valve 2000. For example, FIG. 17E illustrates surgical valve 2000 with a first MEM sensor SEN1 coupled to an outer surface of the valve, generally in alignment with a post 2012 of stent 2010. Sensor SEN1 may take the form of any of the sensors having apertures as described above, and may be coupled to valve 2000 via sutures, for example. Similarly, another MEM sensor SEN2 is illustrated as being coupled to sewing cuff 2020. As with sensor SEN1, sensor SEN2 may take the form of any of the sensors having apertures as described above, and may be coupled to cuff 2020 with sutures. Cuff 2020 may have a substantially flat top and bottom surface correlating to outflow and inflow portions, respectively. Although shown as attached to the outflow portion of cuff 2020, sensor SEN2 may alternately be coupled to the inflow portion of cuff 2020. Preferably, for any valve application, one sensor is coupled to an inflow side of the valve and a second sensor is coupled to an outflow side of the valve, such that the pressure difference across the valve may be calculated. Although shown in relation to surgical valve 2000, the configuration of sensors SEN1 and/or SEN2 described above may be applied to any valve having similar features, such as a sewing cuff.

Figure 17F:
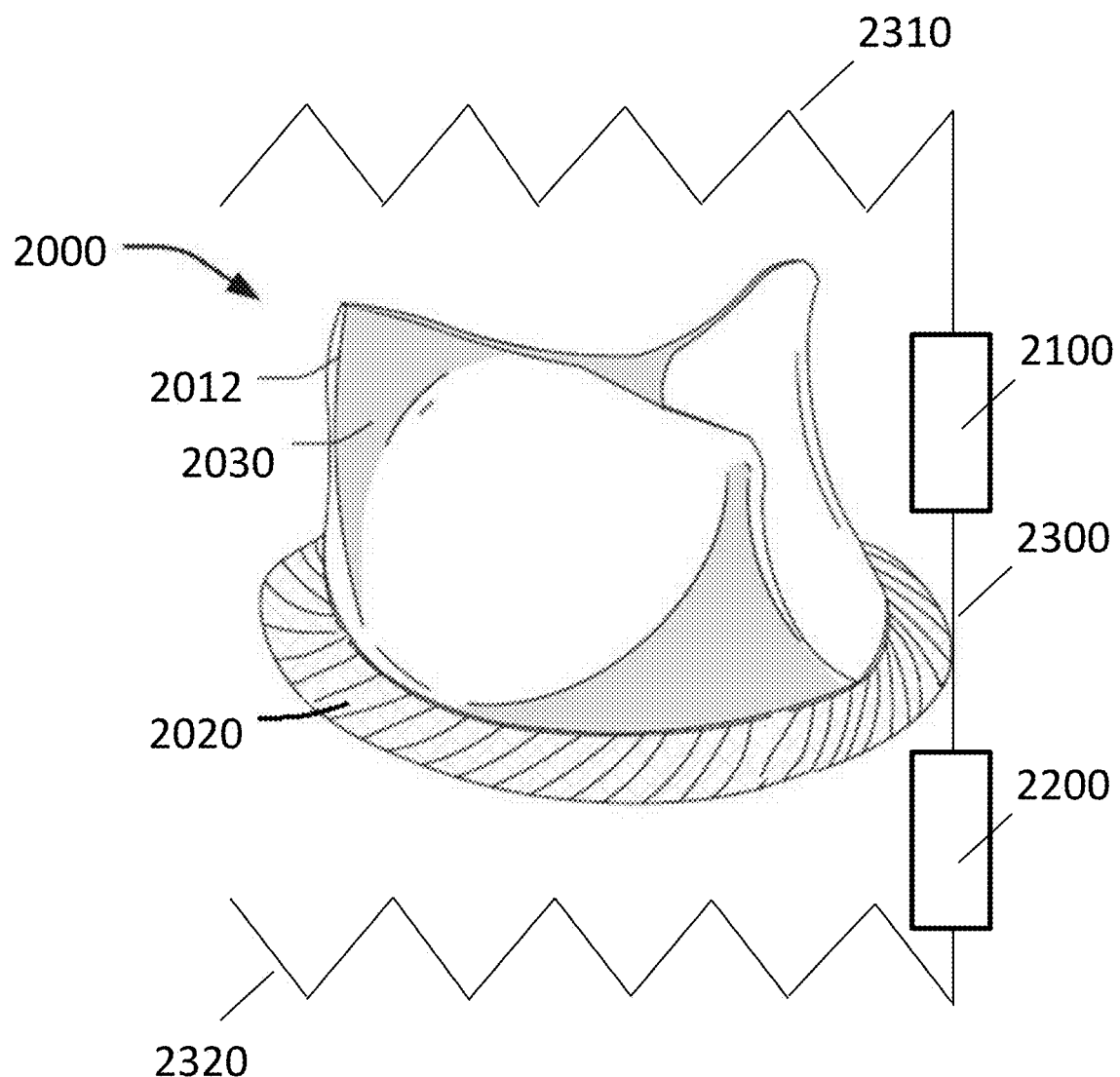
FIG. 17F is a perspective view of the surgical prosthetic heart valve of FIG. 17B with MEM sensors and a sensor frame attached thereto.
Figure 17G:
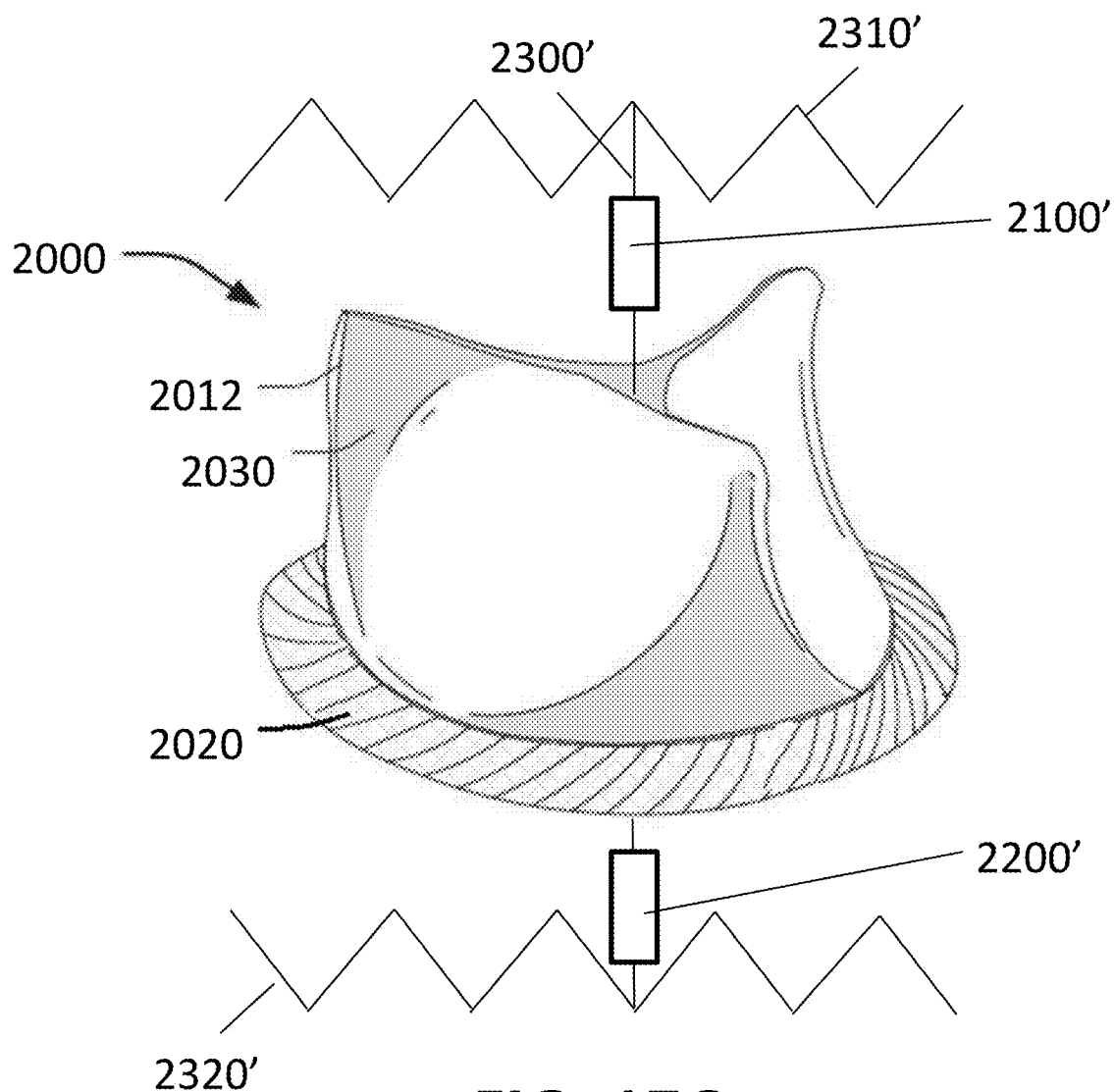
FIG. 17G is a perspective view of the surgical prosthetic heart valve of FIG. 17B with MEM sensors and a sensor frame attached thereto according to a further embodiment of the disclosure.

FIGS. 17F-G illustrate additional sensor systems for use with valve 2000, although it should be clear that the sensor systems can be used with nearly any type of prosthetic heart valve, or even with a native heart valve. The system of FIG. 17F includes an outflow MEM sensor 2100 and an inflow MEM sensor 2200. Sensors 2100 and 2200 may be similar or identical to sensor 300, without the Nitinol loops of sensor 300. Instead, both sensors 2100 and 2200 are coupled to a frame 2300. The coupling may be via suturing, adhesives, welding, or any other suitable method. As shown in FIG. 17F, frame 2300 may be situated outside valve 2000, and may include an outflow frame section 2310 and an inflow frame section 2320. Frame sections 2310 and 2320 may be circular and configured to contact native anatomy to secure frame 2300 in the anatomy in a desired position. Preferably, frame 2300 is formed of a shape-memory alloy, such as Nitinol. When used during an open chest surgical procedure, frame 2300 may be positioned within the native valve prior to coupling surgical valve 2000 to the native valve annulus. Preferably, the portion of frame 2300 connecting outflow frame section 2310 to inflow frame section 2320 is thin so as to not significantly interfere with the connection between cuff 2020 and the native anatomy. Alternatively, the portion of frame 2300 connecting outflow frame section 2310 to inflow frame section 2320 may pass through cuff 2020. Frame 2300 may also be collapsible and expandable to facilitate delivery to the native valve site using a catheter delivery procedure if such delivery is desired. In the configurations described above, frame 2300 is positioned outside leaflets 2030. Although outflow frame section 2310 and inflow frame section 2320 are each illustrated as a single wire in a zig-zag pattern, other patterns, such as single annular rows of cells or multiple annular rows of cells similar to those of stent 102, are possible. If taking the form of annular rows, the rows need not be fully circular but may rather form a portion of a circle or other curved geometry. With the above-described configuration, frame 2300 is positioned so as to support one sensor on the inflow side of valve 2000, preferably in close proximity to the area in which blood enters the valve to provide accurate physiological measurements. Similarly, frame 2300 is positioned so as to support a second sensor on the outflow side of valve 2000, preferably in close proximity to the area in which blood exits the valve to provide accurate physiological measurements.

FIG. 17G illustrates a sensor system similar to that shown in FIG. 17F, with certain differences. For example, the system may include an outflow MEM sensor 2100' and an inflow MEM sensor 2200' which may be the same as or different from outflow sensor 2100 and inflow sensor 2200, respectively. Each sensor 2100' and 2200' may be coupled to a frame 2300' by suturing, adhesives, welding, or any other suitable technique. Frame 2300' may include outflow frame section 2310' and inflow frame section 2320' that are similar or identical to the corresponding sections of frame 2300 described above. The main difference between frames 2300' and 2300 is that outflow frame section 2310' is coupled to inflow frame section 2320' near a center of each respective frame section, so that frame 2300' passes through a center of valve 2000 and sensors 2100' and 2200' are aligned with or near the central axis of the valve. The portion of frame 2300' connecting outflow frame section 2310' to inflow frame section 2320' is preferably thin and straight so as to not interfere with the coaptation of leaflets 2030. Frame 2300' and sensors 2100' and 2200' may be positioned within the native anatomy after implantation of valve 2000 in an otherwise similar fashion to that described for frame 2300. It should further be understood that frame 2300' and sensors 2100' and 2200' may be used with any other type of prosthetic heart valve that can coapt over the portion of frame 2300' connecting outflow frame section 2310' to inflow frame section 2320'. Similarly, frame 2300' with sensors 2100' and 2200' may be implanted for use with a native valve, with the native valve leaflets coapting over the portion of frame 2300' connecting outflow frame section 2310' to inflow frame section 2320'. The embodiment described in connection with FIG. 17G may be advantageous because frame 2300' is mostly independent of prosthetic heart valve 2000 and can be used with other types of valve devices (or native valves) and may be implanted after implantation of a prosthetic valve. However, the embodiment described in connection with FIG. 17F may be advantageous because it avoids potential interference between coaptation of valve leaflets and a frame structure extending through the valves.

Figure 17H:
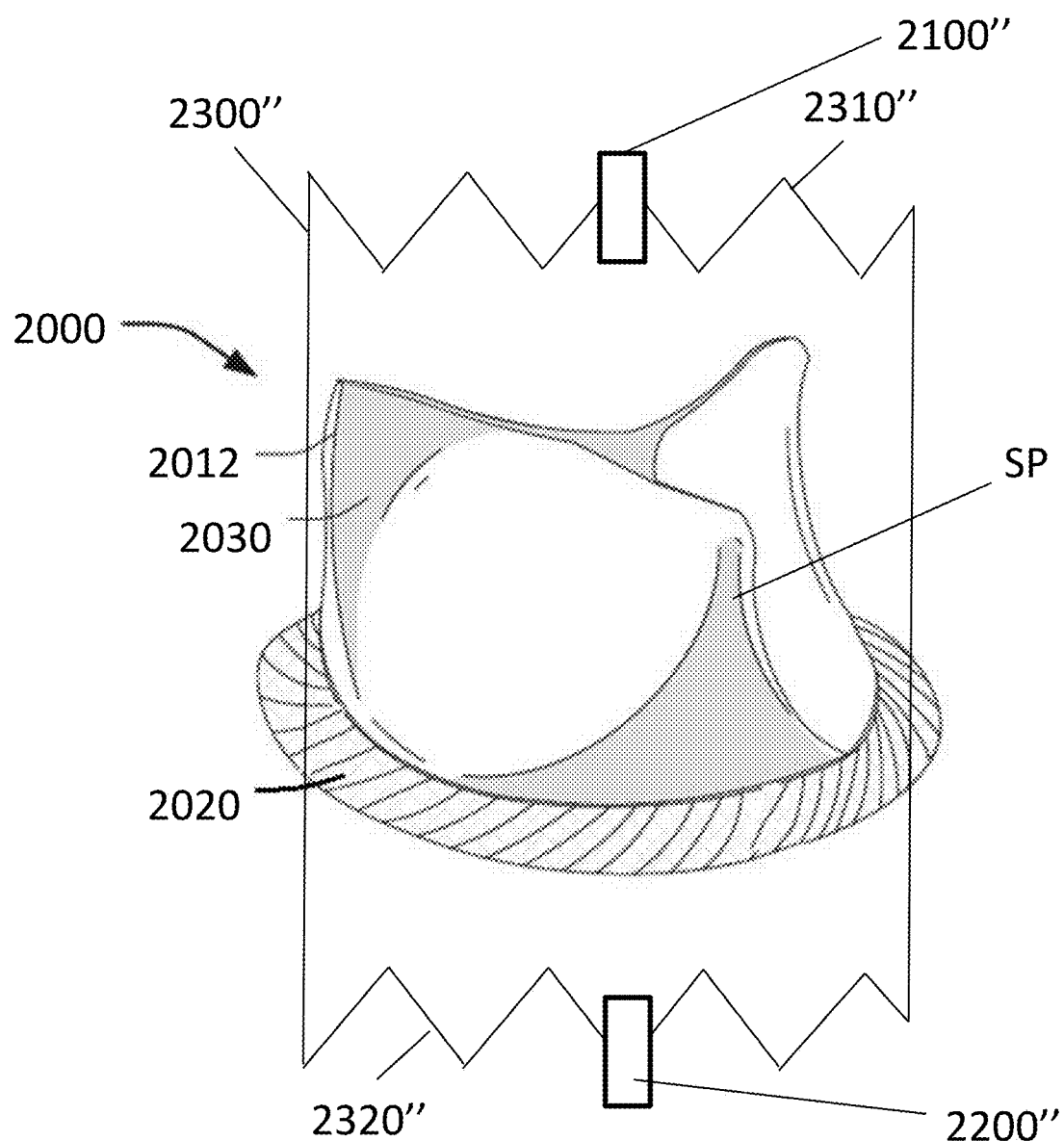
FIG. 17H is a perspective view of the surgical prosthetic heart valve of FIG. 17B with MEM sensors and a sensor frame attached thereto according to yet another embodiment of the disclosure.

FIG. 17H illustrates a sensor system similar to that shown in FIG. 17G, with certain differences. For example, the system may include an outflow MEM sensor 2100" and an inflow MEM sensor 2200" which may be the same as or different from outflow sensor 2100' and inflow sensor 2200', respectively. Each sensor 2100" and 2200" may be coupled to a frame 2300" by suturing, adhesives, welding, or any other suitable technique. Frame 2300" may include outflow frame section 2310" and inflow frame section 2320" that are similar or identical to the corresponding sections of frame 2300' described above. The main difference between frames 2300" and 2300' is that outflow frame section 2310" is coupled to inflow frame section 2320" with frame portions extending outside the leaflets and through the cuff 2020. This embodiment provides the benefits of having sensors 2100" and 2200" centered along the path of blood flow, without having any structures running through the leaflets and possibly interfering with coaptation of the leaflets. In this embodiment, although two struts are shown connecting outflow frame section 2310" and inflow frame section 2320", it may be useful to use three struts for connection, each strut running along a stent post SP of the valve 2000, for example. Having three struts as described above may aid in centering sensors 2100" and 2200" in the path of blood flow.

Figure 18A:
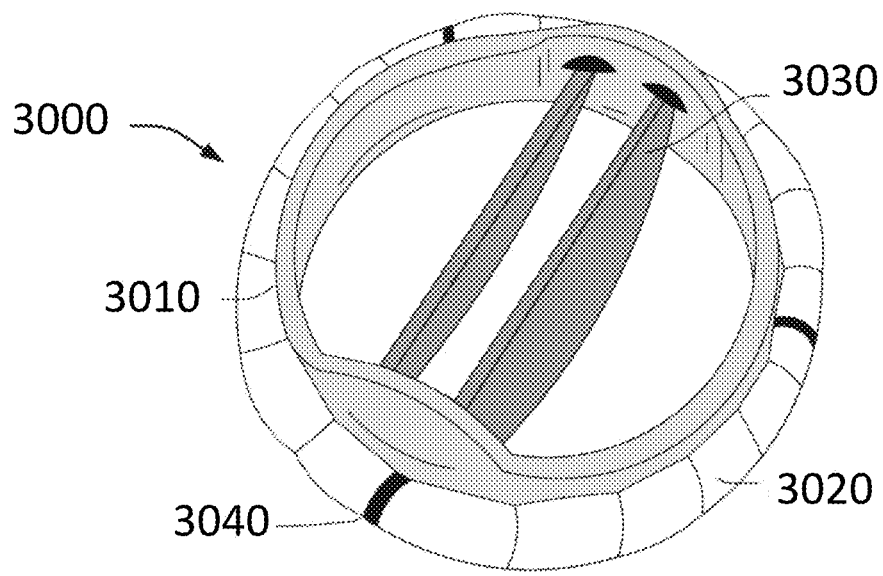
FIG. 18A is a perspective view of a mechanical prosthetic heart valve.
Figure 18B:
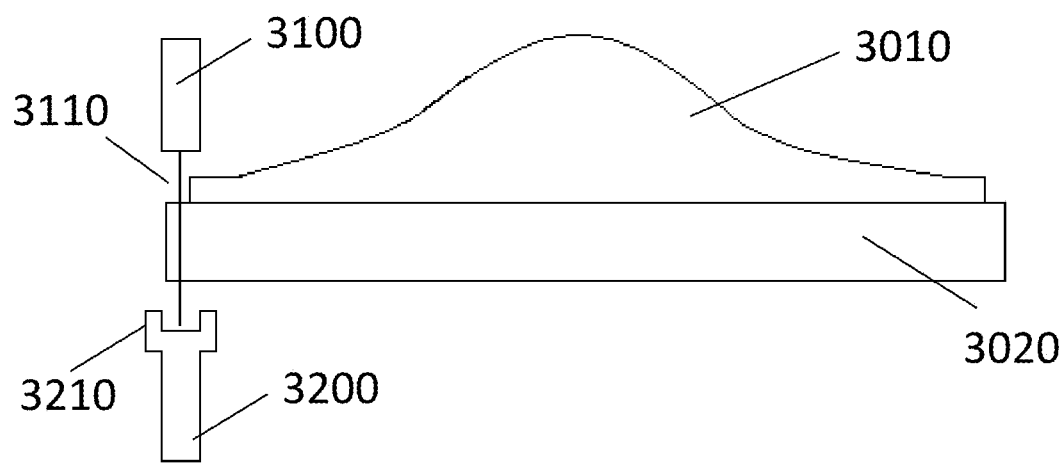
FIG. 18B is a side view of the prosthetic heart valve of FIG. 18A with a pair of MEM sensors attached thereto.

FIGS. 18A-B illustrate yet another application for sensors, a mechanical valve 3000 used for replacing the function of a native heart valve. Mechanical valve 3000 may function similarly to surgical valve 2000 or prosthetic heart valve 100 to replace the function of, for example, an aortic valve or a mitral valve. Generally, valve 3000 includes sewing cuff 3020, support structure 3010, and two actuating flaps 3030 which function as leaflets to enable one-way flow. Cuff 3020 may include a number of marker bands 3040 to aid in localization. Sensors may be coupled to mechanical valve 3000 in a number of ways.

One configuration of attaching an outflow MEM sensor 3100 and an inflow MEM sensor 3200 to mechanical valve 3000 is shown in FIG. 18B. In particular, outflow sensor 3100 may be substantially similar or identical to sensor 300, but without the Nitinol loops of sensor 300. Instead, sensor 3100 includes a coupling element 3110. Similarly, inflow sensor 3200 may be substantially similar or identical to sensor 300, but without the Nitinol loops of sensor 300, and includes a coupling element 3210. As shown, coupling element 3110 may be a male coupling element configured to pass through (or be sutured onto) cuff 3020. Although not required, coupling element 3110 preferably has a sufficient stiffness to keep a stable positional relationship between coupling element 3110 and sensor 3100. In one example, coupling element 3110 may be a metal wire, such as a Nitinol wire. Coupling element 3210 of sensor 3200 preferably has a complementary shape and/or structure to coupling element 3110. For example, coupling element 3110 may have threads configured to threadingly couple to coupling element 3210. In other embodiments, coupling element 3110 may have a press fit relationship with coupling element 3210. To achieve the press fit relationship, an end portion of coupling element 3110 may have a shape that corresponds to the shape of a recess in coupling element 3210. Still further, coupling element 3110 may be sutured to coupling element 3210 to couple sensor 3100 to sensor 3200. Other arrangements for joining coupling element 3110 to coupling element 3210 are also possible, including a snap fit, a ball and socket connection, adhesives, welding and other known techniques. Even further, outflow sensor 3100 may be stapled, glued, sutured, or the like to the outflow end of cuff 3020, either directly or by stapling coupling element 3110 to cuff 3020. If sensor 3100 is directly stapled to cuff 3020, the coupling element 3100 may be unnecessary. Similarly, inflow sensor 3200 may alternatively be stapled, glued, sutured, or the like to the inflow end of cuff 3020.

Figure 19A:
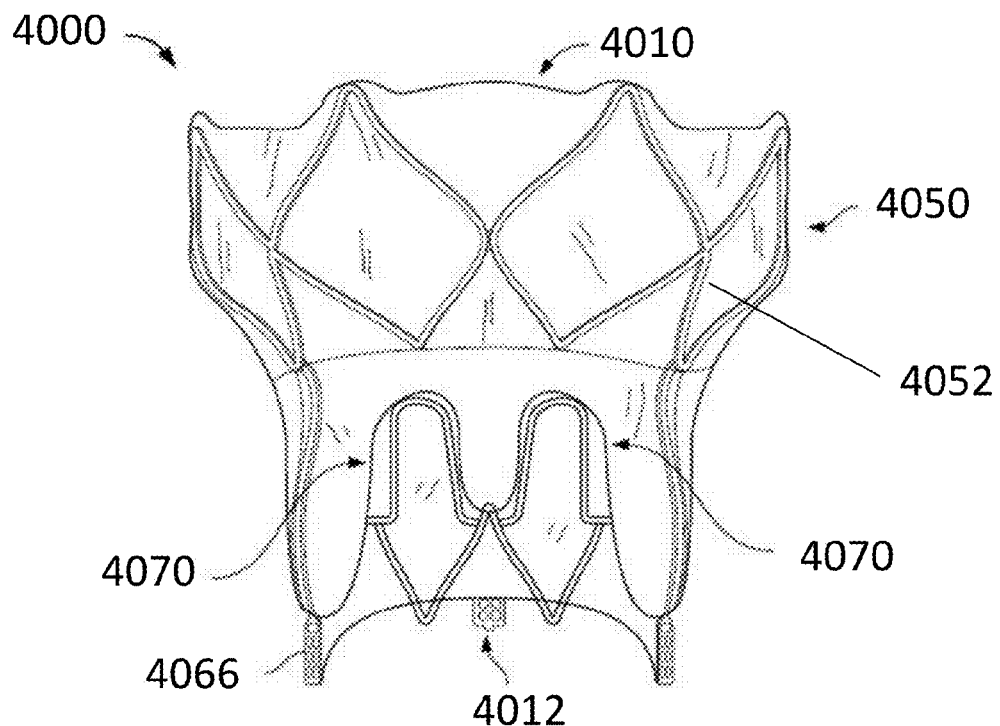
FIG. 19A is a partial side elevational view of a prosthetic mitral valve.

A prosthetic heart valve 4000 according another embodiment of the disclosure is illustrated in FIG. 19A. Prosthetic heart valve 4000 may be similar to prosthetic heart valve 100 in a number of ways, with certain differences making it particularly suitable for use to replace the mitral valve. Prosthetic heart valve 4000 may include a flared stent 4050 and a valve assembly having three leaflets attached to a cylindrical cuff. Prosthetic heart valve 4000 is collapsible and expandable and designed for replacement of a native mitral valve. Prosthetic heart valve 4000 has an inflow end 4010, an outflow end 4012, a substantially cylindrical portion nearer outflow end 4012, and an outwardly flared portion nearer inflow end 4010 when in the expanded condition. It should be understood that prosthetic heart 4000 is not limited to replacement of mitral valves, and may be used to replace other heart valves.

Figure 19B:
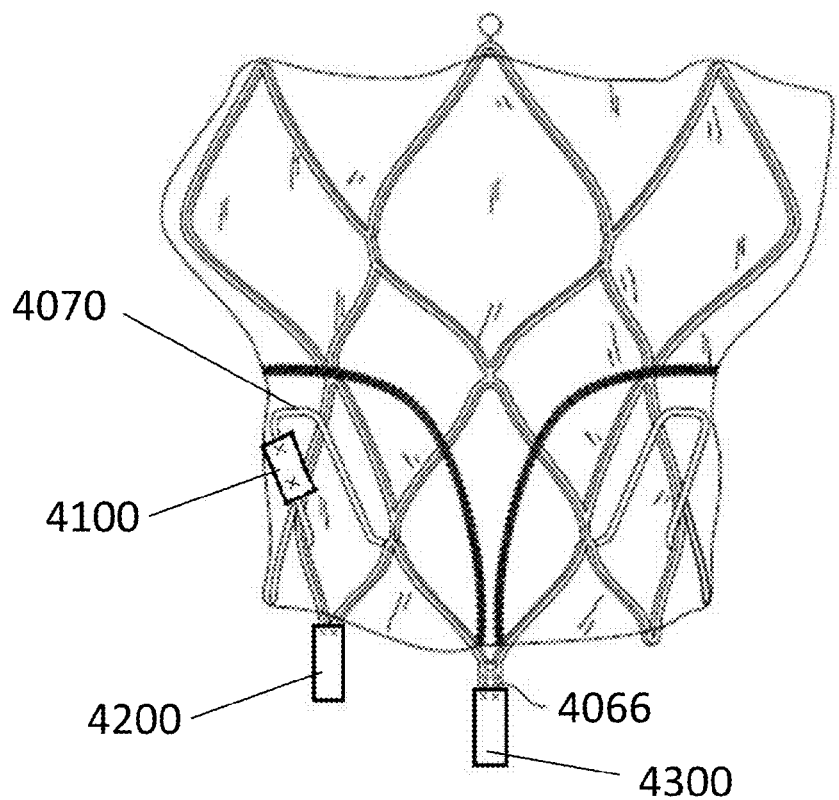
FIG. 19B is a partial side elevational view of the prosthetic mitral valve of FIG. 19B with outflow MEM sensors attached thereto.

Stent 4050 includes a plurality of struts 4052 forming three circumferential rows of cells (best seen in FIG. 19B). Commissure attachment features (CAFs) 4066 may be included near outflow end 4012. The first row of cells may be disposed adjacent outflow end 4012 and the third row of cells may be disposed adjacent inflow end 4010. Stent 4050 may include securement features to help secure valve 4000 within the mitral valve annulus. These securement features may be in the form of struts forming engaging arms 4070 nested within particular cells of stent 4050. Engaging arms 4070 are shape set or biased to project outwardly from those particular cells, and may be configured to engage portions of heart tissue (e.g., native mitral valve leaflets) when prosthetic heart valve 4000 is deployed in a patient. Each engaging arm 4070 may be formed of a shape-memory alloy, and is preferably formed from the same material as stent 4050. Engaging arms 4070 may include two substantially parallel struts connected to one another by a rounded strut. The free end of each engaging arm 4070 defined by the rounded strut projects outwardly into engagement with the surrounding tissue. In certain arrangements, the engaging arms 4070 may clip over the native mitral valve leaflets to hold prosthetic valve 4000 in place.

FIG. 19B illustrates three potential configurations for attaching an outflow sensor to valve 4000. In one arrangement, outflow MEM sensor 4100 may be coupled to valve 4000 by suturing to one or more struts of an engagement arm 4070. Sensor 4100 may take the form of any suitable sensor described above including, for example, a sensor with apertures to facilitate suturing, such as sensor 400 or 500. When engagement arm 4070 is clipped over a native mitral valve leaflet, outflow sensor 4100 will be positioned within the left ventricle. In another arrangement, an outflow MEM sensor 4200 may be coupled to one or more struts 4052 at the annulus portion of the stent 4050 near outflow end 4012. Outflow sensor 4200 may take the form of any of the above-described sensors suitable for connection to stent 4050, including the sensors with apertures. In a third arrangement, an outflow MEM sensor 4300 may be coupled to CAF 4066, for example by suturing. As with the other outflow sensors described immediately above, outflow sensor 4300 may take any suitable form described above, including sensors with apertures to facilitate suturing to CAF 4066. Although three outflow sensors 4100-4300 are illustrated in FIG. 19B, this is for purposes of illustration only, and generally only a single outflow sensor would be attached to valve 4000.

Figure 19C:
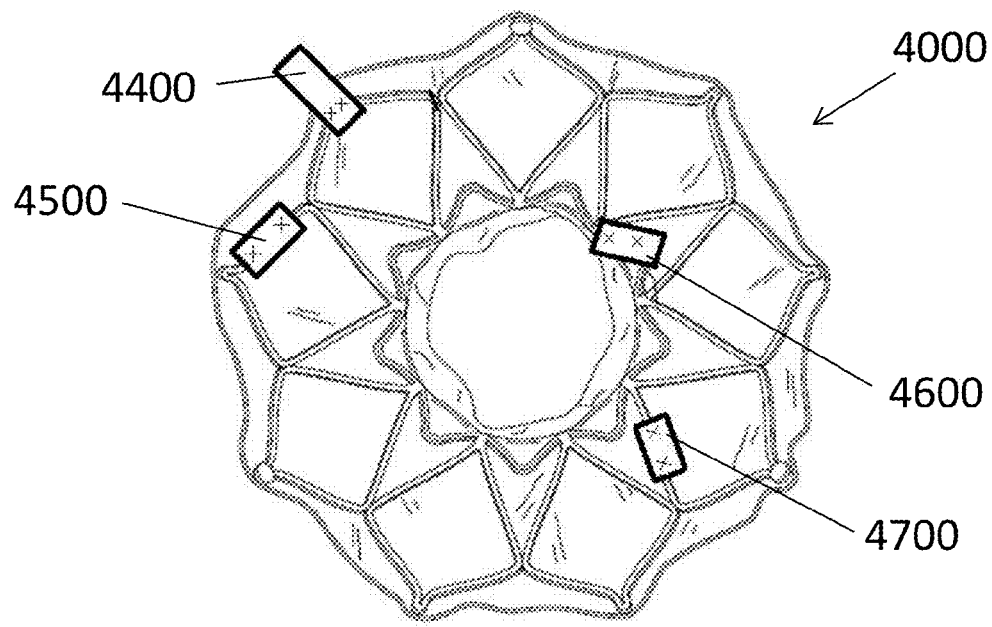
FIG. 19C is an end view of the prosthetic mitral valve of FIG. 19B with inflow MEM sensors attached thereto.

In addition to an outflow sensor, an inflow sensor may also be coupled to valve 4000. FIG. 19C illustrates valve 4000 from inflow end 4010 and shows different configurations for attaching an inflow sensor to valve 4000. For example, inflow MEM sensor 4400 may be coupled to and extend outwardly from one or more struts 4052 on the inflow end 4010 of stent 4050. Alternatively, inflow MEM sensor 4500 may be coupled to and extend along a strut 4052 at the inflow end 4010 of stent 4050. As another alternative, inflow MEM sensor 4600 may be coupled to and extend along a strut 4052 adjacent to the valve assembly on the inflow side of the valve leaflets. Inflow sensor 4600 may be coupled to additional struts not visible in FIGS. 19A-B, the additional struts extending in the longitudinal direction of stent 4050 and being configured to provide additional support for the attachment of a cuff, skirt, or similar structure to stent 4050. As a still further alternative, inflow MEM sensor 4700 may be coupled to and extend along a strut 4052, similar to inflow sensor 4500 but positioned farther from the inflow end 4010 than inflow sensor 4500. Each inflow sensor 4400-4700 may take the form of any of the sensors described above, for example a sensor with suitably positioned apertures to facilitate suturing of the inflow sensor to valve 4000. Although four inflow sensors 4400-4700 are illustrated in FIG. 19C, this is for purposes of illustration only, and generally only a single inflow sensor would be attached to valve 4000.

Figure 19D:
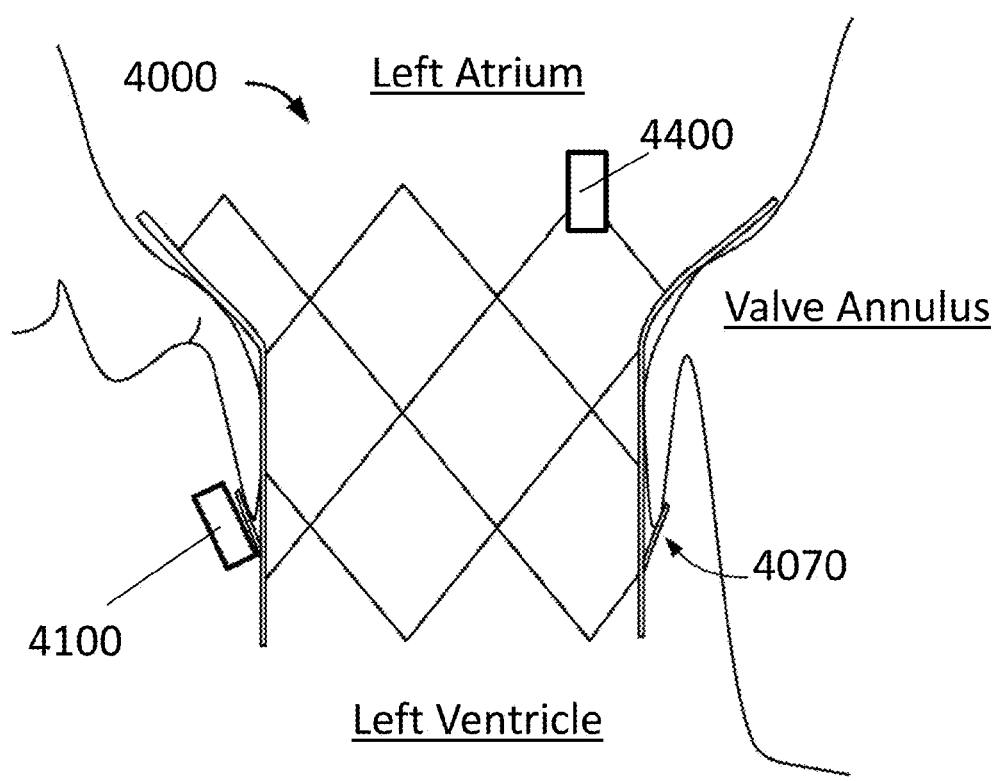
FIG. 19D is a highly schematic representation of the prosthetic mitral valve of FIG. 19A implanted into a native mitral valve annulus with inflow and outflow MEM sensors attached to the prosthetic valve.

FIG. 19D illustrates heart valve 4000 implanted within the native mitral valve annulus with outflow sensor 4100 coupled to one of the engaging arms 4070 and inflow sensor 4400 coupled to and extending from struts 4052 at inflow end 4010 of valve 4000. With this particular configuration, outflow sensor 4100 is positioned within the left ventricle and inflow sensor 4400 is positioned within the left atrium during normal operation, the two sensors providing the ability to detect, for example, the pressure difference between the two heart chambers during operation of valve 4000. Additional details of prosthetic heart valve 4000 and similar prosthetic heart valves are described in greater detail in U.S. Provisional Patent Application No. 62/137,444 titled "Prosthetic Mitral Valve," the disclosure of which is hereby incorporated by reference herein. It should be understood that although valve 4000 is described for use as a replacement for the mitral valve, the same or similar structure, as well as inflow and outflow sensor configurations, may be suitable for other heart valves.

Figure 20A:
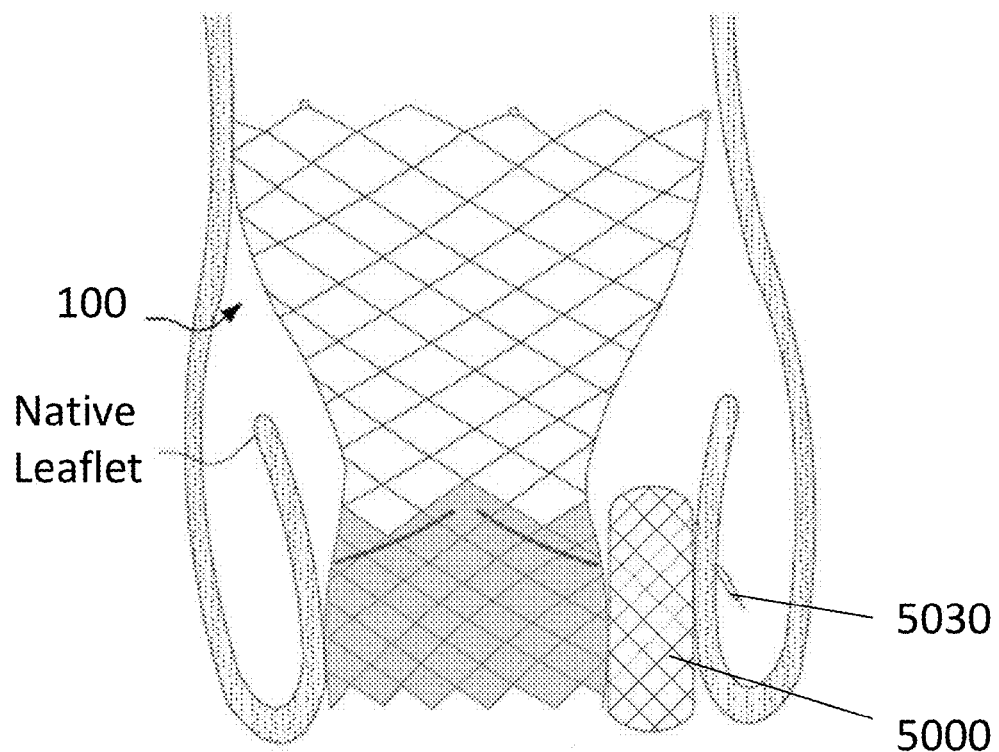
FIG. 20A is a highly schematic view of an occluder positioned between the prosthetic heart valve of FIG. 1 and a native aortic valve leaflet.

The sensors described above or sensors similar to those described above may be used in still other applications. For example, sensors may be used with vascular stents, plugs and/or occluders to take measurements, such as pressure measurements, on one or both ends of the device. For example, FIG. 20A illustrates prosthetic heart valve 100 implanted in the native aortic valve annulus, with an occluder 5000 positioned between valve 100 and a native valve leaflet. Occluder 5000 may be used to fill irregularities between prosthetic heart valve 100 and the native valve annulus. Occluder 5000 may be conformable to allow for superior sealing between the perimeter of prosthetic heart valve 100 and the native valve annulus while exerting a low radial outward force. For example, occluder 5000 may be a metallic structure that may be longitudinally stretched from a relaxed condition to the stretched condition. In the relaxed condition, occluder 5000 may have a cross-section that is greater in size than it is in the stretched condition. Thus, occluder 5000 may be flexible and capable of contracting in the radial direction when a force is applied thereto to conform to the shape of the annulus in which it is implanted. Moreover, the ability of occluder 5000 to longitudinally stretch may enable the occluder 5000 to be delivered through a small diameter catheter.

Occluder 5000 may be formed from a tubular section of braided fabric comprising a plurality of braided strands. The strands forming the braid may have a predetermined relative orientation with respect to one another (e.g., a helical braid). The ends of the strands may be located at a leading end (relatively far from a user implanting the occluder) and a trailing end (relatively close to the user), and may be affixed to one another by any suitable means to prevent unraveling, such as by soldering, brazing, welding, gluing, tying, or clamping. Moreover, occluder 5000 may comprise a plurality of layers of braided fabric and/or other occluding material (e.g., a filler material) such that occluder 5000 is capable of at least partially inhibiting blood flow therethrough in order to facilitate the formation of thrombus and epithelialization. The metal forming occluder 5000 may be a shape-memory material with elastic and/or memory properties, such as Nitinol, although other materials may be suitable. Additional details of occluder 5000 and similar occluders are provided in U.S. Patent Publication No. 2014/0277426, the disclosure of which is hereby incorporated by reference herein.

As shown in FIG. 20A, occluder 5000 is disposed between prosthetic heart valve 100 and a native aortic valve leaflet. An anchor 5030 attached to the body of occluder 5000 via a cord, may have one or more sharp ends for piercing through the native valve leaflet. Once anchor 5030 has passed through the native valve leaflet, occluder 5000 is effectively affixed to the native valve leaflet and secured in place between prosthetic heart valve 100 and the native valve leaflet. In one variation of this embodiment, anchor 5030 may be configured to secure occluder 5000 to prosthetic heart valve 100 by being fastened to select cells of stent 102.

Figure 20B:
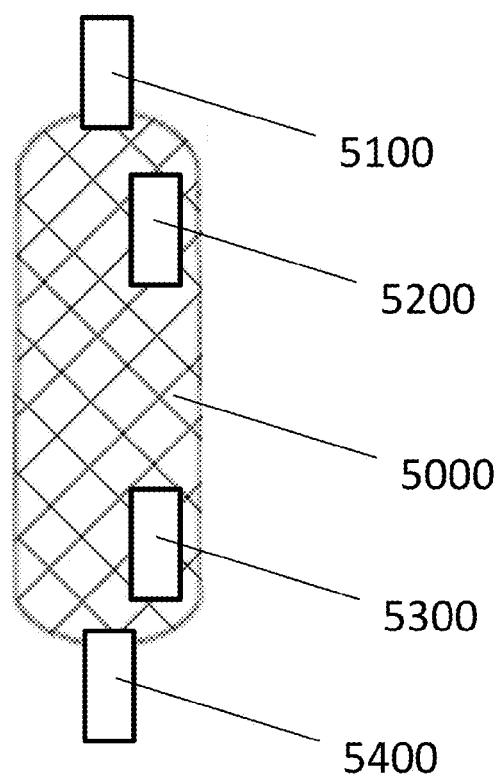
FIG. 20B is a highly schematic view of the occluder of FIG. 20A with inflow and outflow MEM sensors attached thereto.

One or more sensors may be coupled to occluder 5000 so that measurements, such as pressure measurements, may be taken after prosthetic heart valve 100 and occluder 5000 are implanted. For example, FIG. 20B provides a closer view of occluder 5000, with anchor 5030 omitted for clarity, illustrating potential configurations for attaching sensors to occluder 5000. In particular, outflow MEM sensor 5100 may be coupled to a first end of occluder 5000. Outflow sensor 5100 may take the form of any of those described above that may be suitable for attachment to occluder 5000, including, for example, sensors with apertures to facilitate suturing. In one example, the end of occluder 5000 facing the aorta may not have a closed metallic stent structure, but may have a substantially cylindrical stent structure filled with a filler material. In that embodiment, sensor 5100 may be attached directly to the filler material, for example by sutures. However, if occluder 5000 includes a closed stent structure at the end facing the aorta, sensor 5100 may be connected, for example by suturing, directly to the stent structure. In both cases, outflow sensor 5100 may extend away from the end of occluder 5000 and toward the aorta, and may be configured to take measurements within the aorta, for example pressure readings. Alternatively, outflow MEM sensor 5200 may be coupled along the length of the body of occluder 5000 instead of at an end. This coupling may be effected by, for example, suturing outflow sensor 5200 directly to the stent structure of occluder 5000 and/or to a fabric provided on or within the stent structure. If positioned along the body of occluder 5000, outflow sensor 5200 should be positioned closer to the end of the occluder facing the aorta. In addition to an outflow sensor 5100 or 5200, an inflow MEM sensor 5300 or 5400 may also be coupled to occluder 5000. Inflow sensor 5300 may be attached to occluder 5000 in the same manner as outflow sensor 5200 and may take a similar form, the difference being that inflow sensor 5300 is configured to be positioned within the left ventricle when occluder 5000 is implanted in the native valve annulus. Similarly, inflow MEM sensor 5400 may be coupled to occluder 5000 in a similar manner as outflow sensor 5100, and may take a similar or identical form to outflow sensor 5100, the difference being that inflow sensor 5400 is configured to extend into the left ventricle. Preferably, a single inflow sensor and a single outflow sensor are used with occluder 5000 to determine the pressure difference, or other relevant parameters, between the aorta and the left ventricle during operation of prosthetic heart valve 100. It should further be understood that although occluder 5000 is illustrated for use in the native valve annulus of the aortic valve, the same or similar structures may be used in other heart valves, or in other locations in the vasculature in which an occluder, plug, or stent may be used, and may include one or more sensors as desired to make desired physiological measurements.

The sensors described above may have still further applications, for example with other occluders, for example those used to treat patent foramen ovale ("PFO"), atrial septal defect ("ASD"), ventricular septal defect ("VSD"), patent ductus arteriosus ("PDS"), or to close the left atrial appendage ("LAA").

Closure devices may have various configurations depending on factors such as the type of abnormality to be occluded, the location of the target site, the condition of the patient's vasculature, and the practitioner's preferences. For example, in the depicted embodiment of FIG. 21A, a closure device 6000 has a first expanded volume portion 6010 and a second expanded volume portion 6020 that are substantially perpendicular to a central axis extending along closure device 6000. The first expanded volume portion 6010 may be proximate a first end of closure device 6000, with the second expanded volume portion 6020 spaced axially from the first expanded volume portion 6010 and proximate a second end of closure device 6000. The first expanded volume portion 6010 may be connected to the second expandable volume portion 6020 via an axial portion 6030.

Figure 21A:
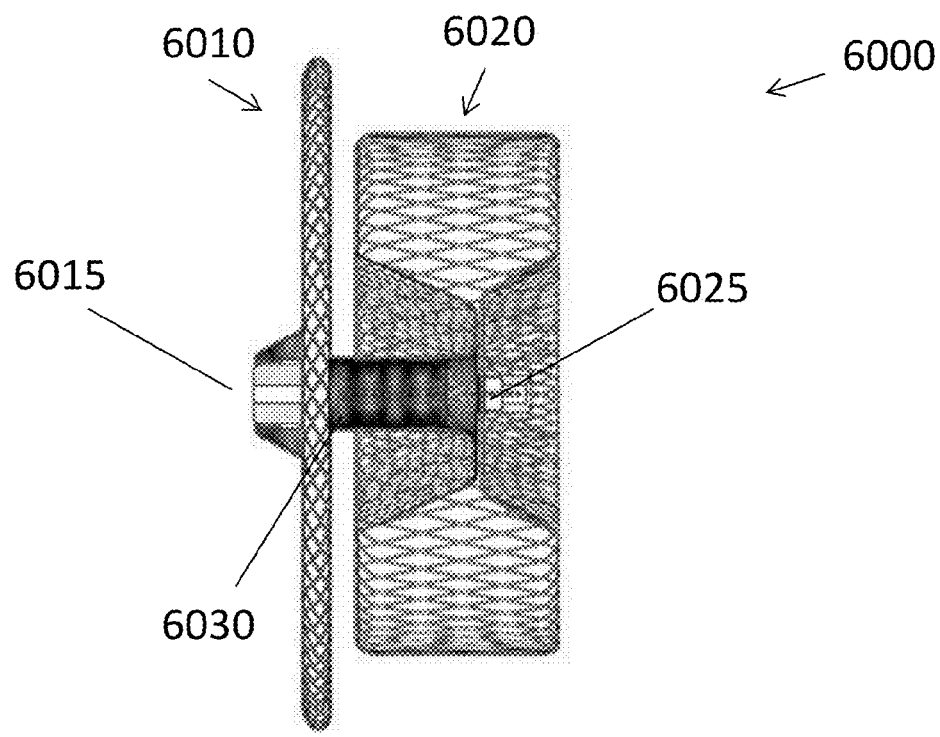
FIG. 21A is a cross-sectional view of a closure device according to an embodiment of the disclosure.

As depicted in FIG. 21A, the first expanded volume portion 6010 may have the shape of a thin disk, and is intended to help maintain the closure device 6000 in position at the target site, as described in greater detail below. The second expanded volume portion 6020 may, in some cases, be a generally cylindrical body that is substantially thicker in the axial direction than first portion 6010 and axially disposed toward the second end. The second expanded volume portion 6020 may be sized to be somewhat larger in diameter (e.g., about 10-30%) than the inside diameter of the vessel, cavity, or lumen to be occluded to facilitate anchoring of the device to prevent dislodgement, but not so large as to not fit in the vessel, cavity or lumen.

At the same time, the first expanded volume portion 6010 of the closure device 6000 may have a diameter that is larger than the diameter of the second expanded volume portion 6020. This larger diameter is intended to abut the wall surrounding the abnormal aperture to prevent device movement further into the aperture and to assist in sealing the aperture. For example, the first expanded volume portion 6010 may be oversized so as to overlie the ostium or opening of the LAA in a position adjacent to, and in flush contact with, the wall of the atrium. The first expanded volume portion 6010 may also be flexible so as to be capable of conforming to the curvature of the wall of the atrium in LAA applications or other vascular structures in other applications. Although one configuration of the first and second expanded volume portions 6010, 6020 is described above and shown in the figures, various other configurations and sizes may be used depending on the particular application or condition to be treated. For example, one or both expanded volume portions 6010, 6020 may be thin disks or disks having a convex distal end, or the device may include a smaller diameter cylindrical portion between two larger diameter disks. Moreover, the depth or thickness of the first and/or second expanded volume portions may depend on the thickness and number of layers used to make the medical device 6000.

The first expanded volume portion 6010, the second expanded volume portion 6020, and the axial portion 6030 may each be formed of a shape-memory alloy, such as braided Nitinol, to facilitate collapsing the closure device 6000 for minimally invasive delivery, and to facilitate expansion to a pre-set shape upon delivery of the closure device 6000 to the intended location. A first coupling 6015 may be disposed adjacent the first expanded volume portion 6010 and may enable connection of a delivery device or other device to closure device 6000. For example, first coupling 6015 may include internal or external threads that mate with corresponding threads of another device. A second coupling 6025, similar to the first coupling 6015, may be disposed adjacent to or within the second expanded volume portion 6020. Second coupling 6025 may also include internal or external threads for connection to corresponding threads of another device. It should be understood that other coupling mechanisms, such as press-fit or snap-fit arrangements, may be utilized in first and second couplings 6015, 6025. Additional details of closure device 6000 and similar devices are described in U.S. Pat. No. 8,758,389, the disclosure of which is hereby incorporated by reference herein.

Figure 21B:
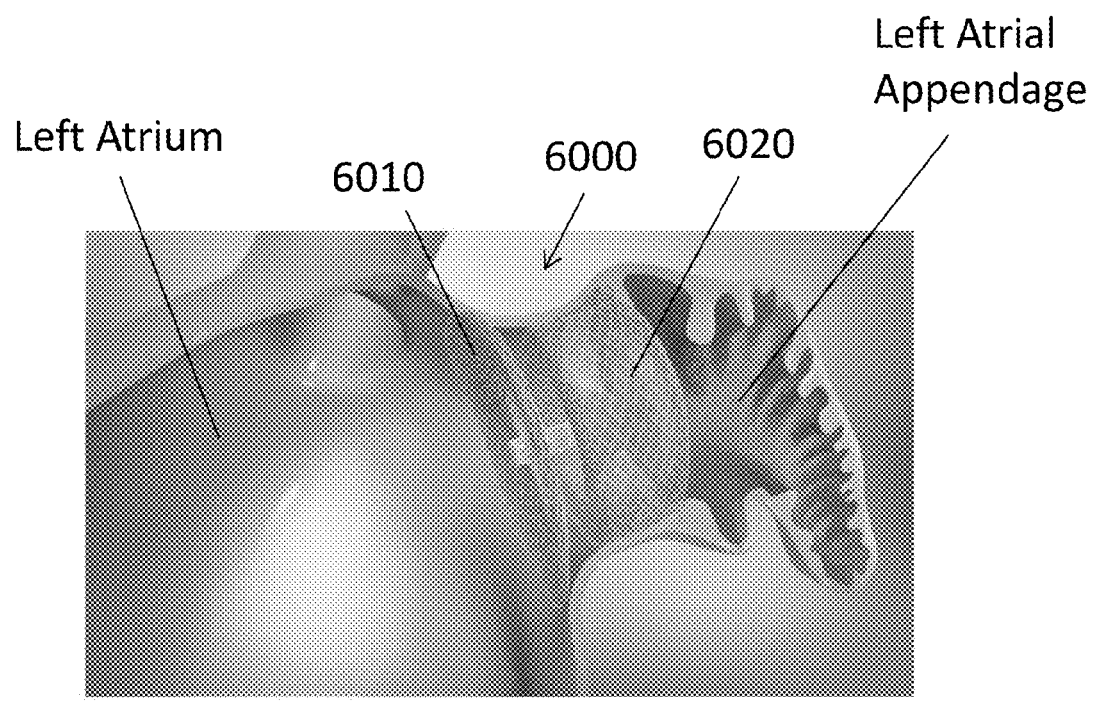
FIG. 21B is a highly schematic view of the closure device of FIG. 21A implanted into a left atrial appendage.

FIG. 21B is a schematic view of closure device 6000 positioned within the LAA of a left atrium. In patients with certain conditions, such as atrial fibrillation, blood clots may tend to form in the LAA. Implanting a device such as closure device 6000 may lead to partial or complete occlusion of the LAA, thus reducing the risk of thrombi breaking off the LAA and entering the blood stream.

Figure 21C:
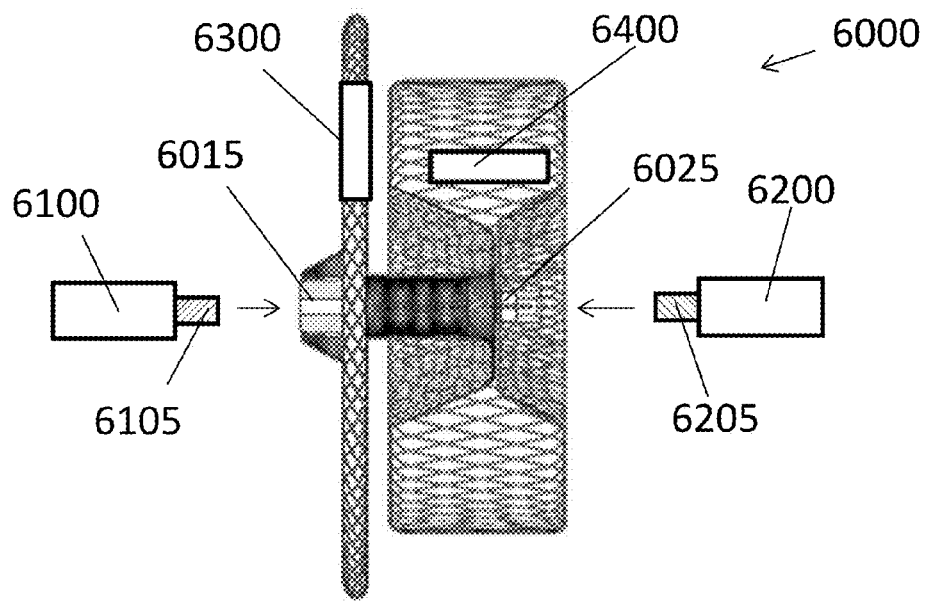
FIG. 21C is a cross-sectional view of the closure device of FIG. 21A with MEM sensors attached thereto.
Figure 21D:
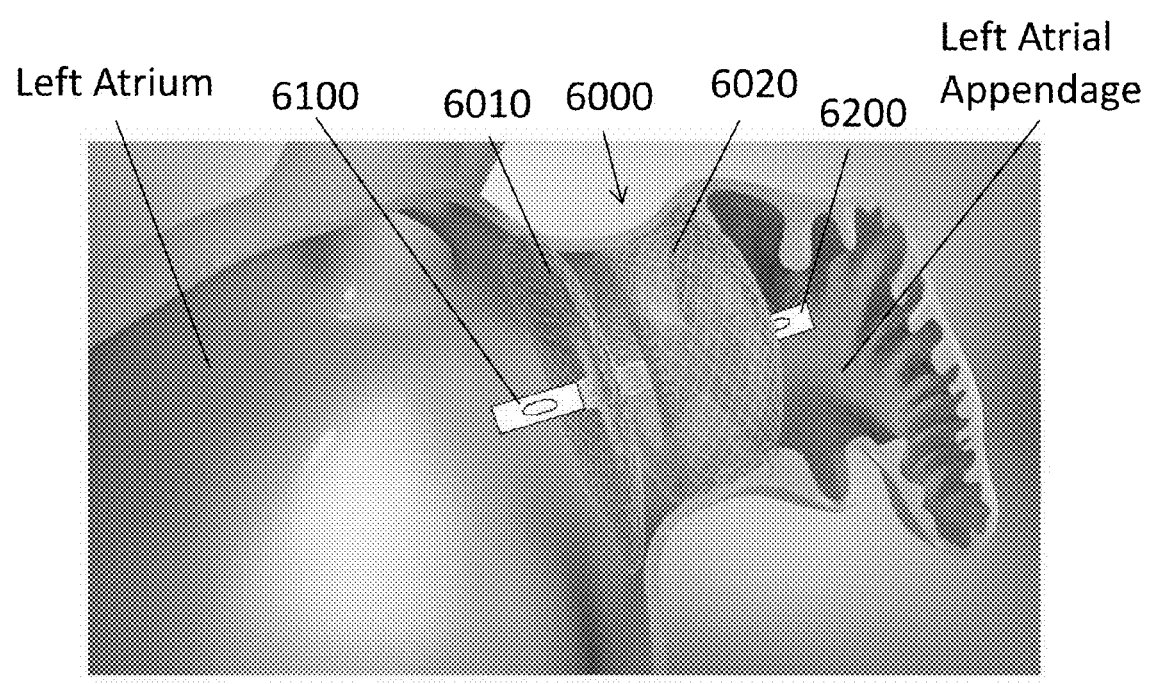
FIG. 21D is a highly schematic view of the closure device of FIG. 21A with MEM sensors attached thereto implanted into the left atrial appendage.

FIG. 21C illustrates potential configurations for coupling sensors to closure device 6000. A first sensor may be coupled to closure device 6000 so as to be exposed to the left atrium in which blood is still flowing. A second sensor may additionally or alternatively be coupled to closure device 600 so as to be exposed to the LAA, which is intended to be sealed off from blood flow by closure device 6000. For example, a MEM sensor 6100 may take a similar form to sensor 300 described above, but rather than having Nitinol loops, sensor 6100 may include a coupling end 6105 configured to couple to first expanded volume 6010, for example to coupling 6015. In that regard, coupling end 6105 may include threads that mate with corresponding threads in coupling 6015. Thus, coupling 6015 may serve to couple to both a delivery device and sensor 6100. In other embodiments, coupling end 6105 may connect to coupling 6015 using a press fit or other suitable connection. Sensor 6100 may be coupled to first expanded volume portion 6010 after closure device 6000 has been implanted into the LAA. As shown in FIG. 21D, with the configuration described above, sensor 6100, when coupled to closure device 6000, extends outward from and substantially along the longitudinal axis of closure device 6000.

Alternatively, MEM sensor 6300 may be coupled directly to first expanded volume 6010 such that, when closure device 6000 is implanted into the LAA, sensor 6300 is exposed to the left atrium. Sensor 6300 may take the form of any suitable sensor described above. For example, sensor 6300 may be any of the sensors described above having apertures to enable sensor 6300 to be coupled directly to the frame of first expanded volume 6010 using sutures. Although FIG. 21C shows sensors 6100 and 6300 both coupled to closure device, in practice, there is preferably only a single sensor coupled to first expanded volume 6010 such that one sensor is exposed to the left atrium.

In addition or alternatively to a sensor exposed to the left atrium, one sensor is preferably coupled to second expanded volume 6020 so as to be exposed to the occluded LAA. For example, MEM sensor 6200 may take substantially the same form as sensor 6100, with coupling end 6205 threaded into second coupling 6025 of second expanded volume 6020. Sensor 6200 may be coupled to second expanded volume 6020 prior implantation of the closure device 6000 into the LAA. In another configuration, a MEM sensor 6400, which may be substantially identical to sensor 6300, may be coupled to second expanded volume 6020, for example via suturing or any other suitable attachment means. Again, although both sensors 6200 and 6400 are illustrated in FIG. 21C, preferably only one sensor is attached to second expanded volume 6020. FIG. 21D is a schematic illustration of closure device 6000 implanted in the LAA with sensor 6100 coupled to first expanded volume 6010 and sensor 6200 coupled to second expanded volume 6020. With this configuration, measurements, such as blood flow or pressure measurements, may be taken within the LAA and within the left atrium to determine, for example, if the LAA has been appropriately sealed off by closure device 6000.

As noted above, there are many applications for sensors 300 and modified versions of sensor 300 described above. When utilized on prosthetic heart valves implanted in the native aortic valve, one such application is the assessment of the severity of aortic regurgitation. Aortic regurgitation may negatively affect the prognosis after transcatheter aortic valve replacement, with increased morbidity and mortality in patients with more than mild regurgitation. Thus, techniques may be employed using the sensors described above to quantify the extent of regurgitation, if any.

One measure of regurgitation in aortic heart valves is the aortic regurgitation index, which may be defined as the ratio of the transvalvular gradient between the diastolic blood pressure (RRdia) in the aorta and the left-ventricular end-diastolic blood pressure (LVEDP) to the systolic blood pressure (RRsys) in the aorta: $[(RRdia-LVEDP)/RRsys] \times 100$. The aortic regurgitation index has an inverse correlation to the severity of aortic regurgitation and allows a physician to differentiate between patients with mild, moderate, or severe aortic regurgitation. The aortic regurgitation index may also be independently used to predict the associated 1-year mortality risk for a given patient upon collection of data.

Figure 22A:
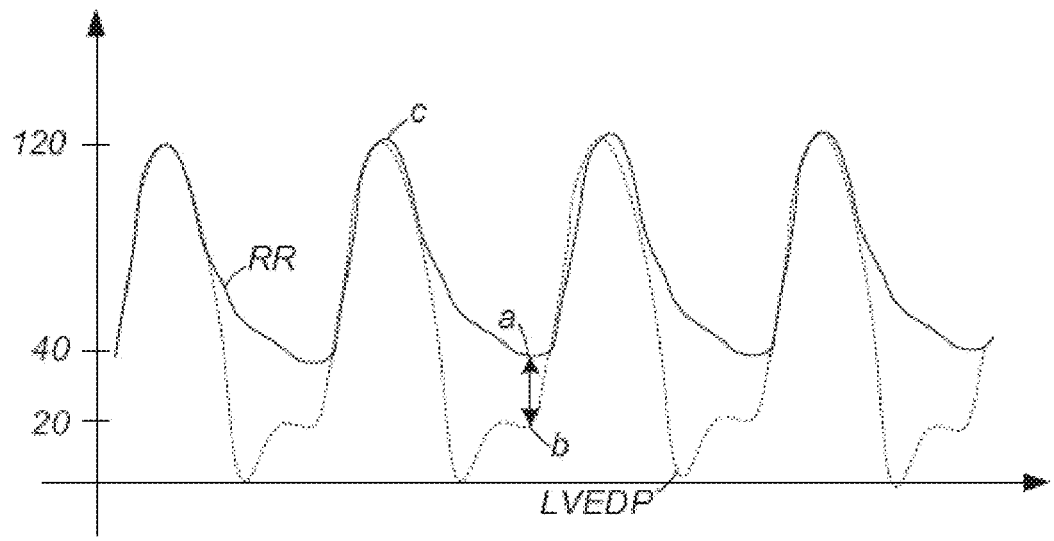
FIGS. 22A and 22B are graphs showing examples of hemodynamic assessments during transcatheter aortic valve replacement procedures.

FIG. 22A illustrates the aortic regurgitation index in a patient with moderate aortic regurgitation. As seen in the graph, the patient has an aortic diastolic blood pressure (RRdia) of 40, a left-ventricular end-diastolic blood pressure (LVEDP) of 20, and an aortic systolic blood pressure (RRsys) of 120. Using the formula for the aortic regurgitation index defined above yields the following:

$$(RRdia-LVEDP)/RRsys \times 100 = (a-b)/c \times 100 = (40-20)/120 \times 100 = 16.7$$

Figure 22B:
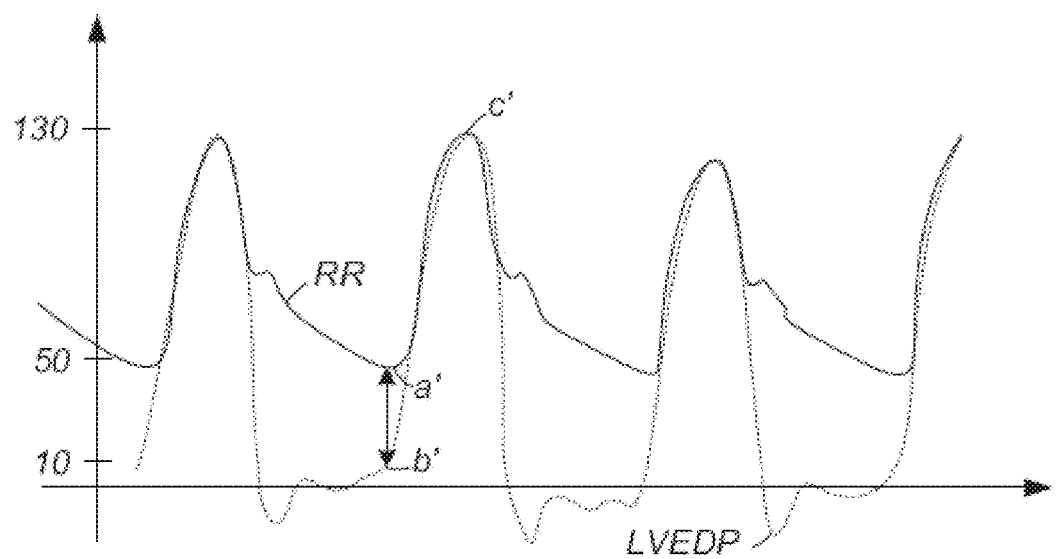

For a second patient, the aortic regurgitation index indicates a trivial amount of aortic regurgitation as shown in FIG. 22B. For this patient, the aortic diastolic blood pressure (RRdia) is 50, the left-ventricular end-diastolic blood pressure (LVEDP) is 10 and the aortic systolic blood pressure is 130, yielding an aortic regurgitation index as calculated below:

$$(RRdia-LVEDP)/RRsys \times 100 = (a'-b')/c' \times 100 = (50-10)/130 \times 100 = 30.8$$

When used in conjunction with prosthetic heart valves, sensors 300 and the variations described above may measure blood pressure to determine an aortic regurgitation index and thus reveal the severity of the regurgitation. Based on the calculated aortic regurgitation index, follow-up treatment may be advised. Additionally, sensors 300 and variations thereof described above may be used to decide when to fully deploy a partially deployed heart valve and the type of corrective measure necessary, if any.

Figure 23:
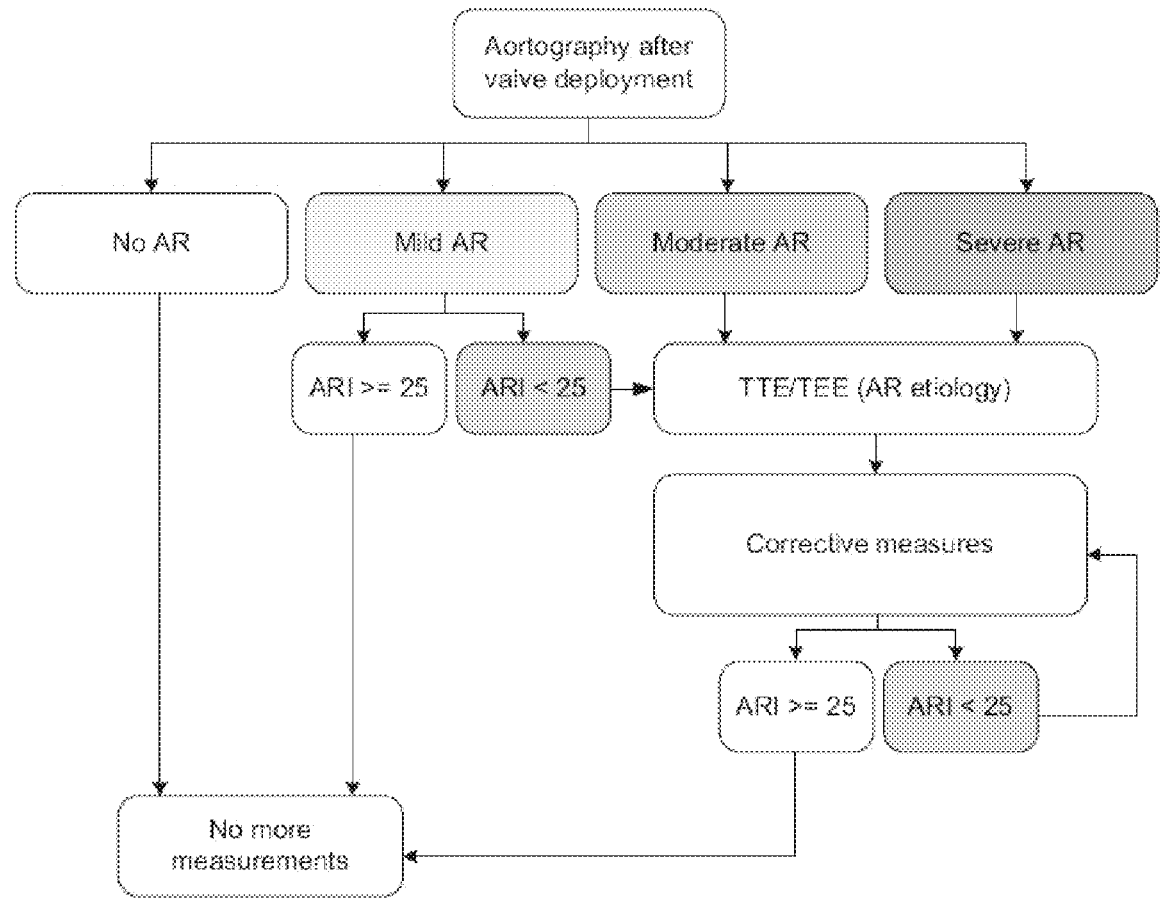
FIG. 23 is a flow chart showing one possible method of using a prosthetic heart valve with sensors attached thereto.

One example of a method using a prosthetic heart valve having sensors is shown in FIG. 23. In this method, a preliminary technique, including but not limited to aortography, may be performed after valve deployment in order to make a preliminary assessment of aortic regurgitation. This preliminary assessment may provide a rough classification of the regurgitation into four groups: no aortic regurgitation, mild aortic regurgitation, moderate aortic regurgitation, and severe aortic regurgitation. If the preliminary technique shows no aortic regurgitation, then no measurements are taken and the procedure is determined to be a successful one (e.g., valve function is adequate). If the preliminary technique shows that mild aortic regurgitation is present, then sensors 300 or variations thereof described above may be used to quantify the amount of aortic regurgitation by making measurements used to calculate an aortic regurgitation index (ARI), as described above. An aortic regurgitation index greater than or equal to 25 may indicate that the aortic regurgitation is negligible, which may result in no further measurements or corrective measures. If, however, the index is less than 25, then the aortic regurgitation may be classified as either moderate or severe. In either case, further diagnostic techniques, such as, for example, transesophageal echocardiography (TEE) or transthoracic echocardiography (TTE), may be performed to further assess the situation, followed by a corrective measure. The corrective measure may include any one or more of post-dilation techniques, snaring to adjust the position of the valve, valve-in-valve implantation (e.g., implanting an additional valve inside an already-implanted valve), balloon expansion, resheathing and redeploying techniques, deploying a valve of the same or different type, modified redeployment, or the addition of paravalvular leakage features, etc. Following the corrective measure, sensors 300 or variations described above may be used to recalculate the aortic regurgitation index. If the aortic regurgitation index is greater than or equal to 25, then the corrective measure may be considered successful and no further measurements or measures are taken. If, however, the aortic regurgitation index remains below 25, then further corrective measures may be necessary. This loop from corrective measure to aortic regurgitation index calculation may continue until satisfactory positioning and functioning of the prosthetic heart valve are achieved.

In the example above, the calculation of the aortic regurgitation index using sensors 300 or variations thereof described above is performed after the implantation of the prosthetic heart valve to ensure proper functioning. Such pressure measurement may also allow monitoring of overall cardiac health of the patient, as well as functioning of the prosthetic device. In addition, sensors may be used to monitor an implanted prosthetic heart valve or repair device at any time, including before implantation of a therapeutic device or after discharge of the patient from the hospital, and for as long as the device is implanted in the patient. For example, sensors may be used to aid in the implantation of a therapeutic device. In one example, sensors may be used to virtually reconstruct the geometry of the native valve annulus to predict potential paravalvular leakage of a heart valve with known dimensions. Such sensors may be used alone or in combination with balloons, or balloon-expanded, or self-expanding diagnostic rings, holders, sizers, or stents. For valve-in-valve procedures, sensors on an already implanted valve may be used to aid in docking a second valve within the implanted valve.

Figure 24:
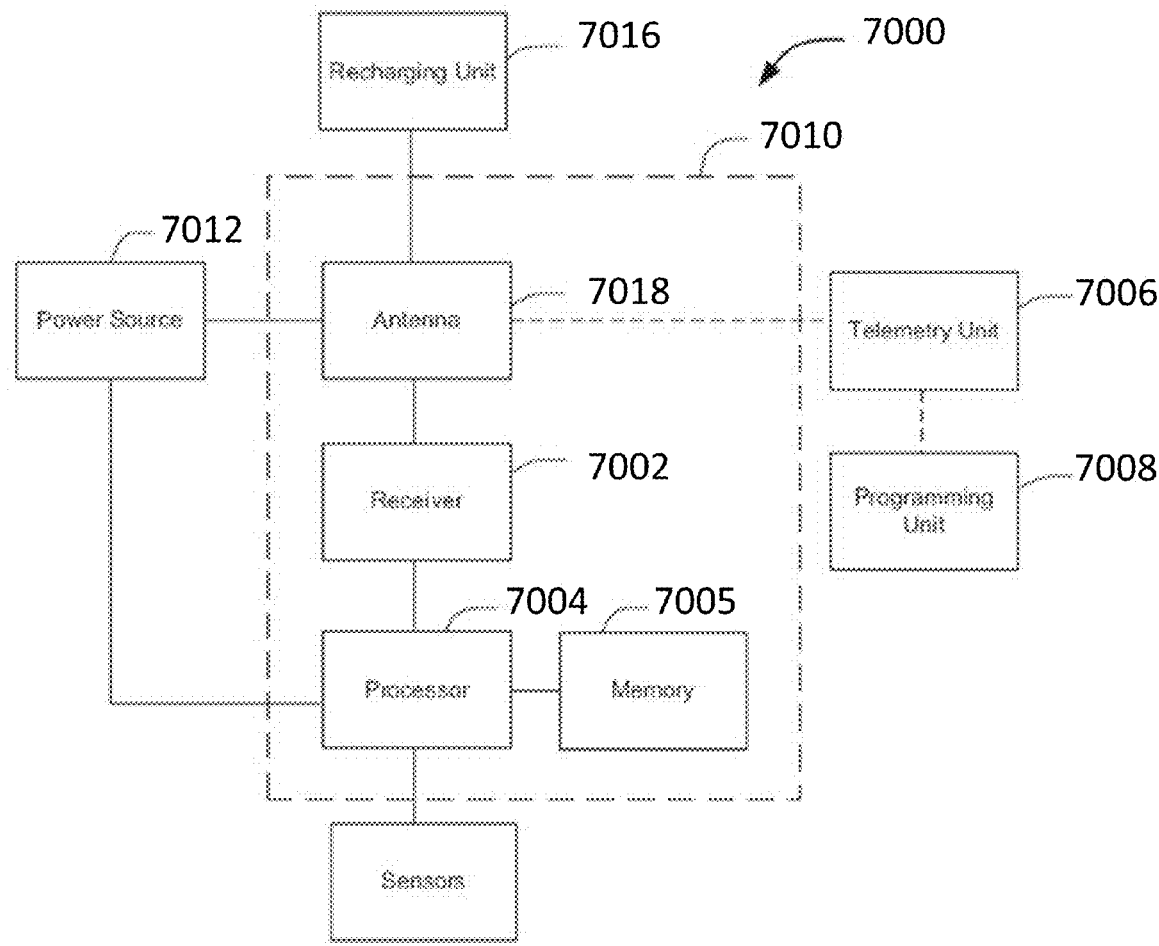
FIG. 24 is a schematic representation of a system for valve evaluation using the sensors of the present disclosure.

FIG. 24 is a schematic overview of one embodiment of the components of a valve diagnostic system 7000 including an electronic subassembly 7010 disposed within a control module. It will be understood that the valve diagnostic system can include more, fewer, or different components and can have a variety of different configurations.

Some of the components (for example, power source 7012, antenna 7018, receiver 7002, and processor 7004) of valve diagnostic system 7000 can be positioned on one or more circuit boards or similar carriers. Any power source 7012 can be used including, for example, a battery, such as a primary battery or a rechargeable battery. Examples of other power sources include super capacitors, nuclear or atomic batteries, mechanical resonators, infrared collectors, thermally powered energy sources, flexural powered energy sources, bioenergy power sources, fuel cells, bioelectric cells, osmotic pressure pumps, and the like.

If the power source 7012 is a rechargeable battery, the battery may be recharged using the optional antenna 7018, if desired. Power can be provided to the battery for recharging by inductively coupling the battery through the antenna to a recharging unit 7016 external to the user.

A processor 7004 is included to obtain data from the sensors relating to force, pressure or elasticity measured by each of the sensors. Any processor can be used and can be as simple as an electronic device that, for example, is capable of receiving and interpreting instructions from an external programming unit 7008 and performing calculations based on the various algorithms described above. A memory 7005 may include data in the form of a dataset for performing various steps of the algorithm. In some examples, data from the sensors relating to pressure, forces and the like may be passed to processor 7004 and compared against a dataset stored in memory 7005 to determine if further treatment and/or diagnosis is necessary. Additionally, data relating to valve diagnosis may be sent from programming unit 7008 to processor 7004 and the processor may determine the appropriate course of action or send an alert to a clinician. Communication between programming unit 7008 and processor 7004 may be accomplished via communication between antenna 7018 and telemetry unit 7006. Additionally, sensors may be in communication with one or more wearable devices to enable the user to continuously monitor or track the functionality of a therapeutic device. Such wearable devices may track or log data, and if necessary, provide the data to a clinician or alert emergency personnel if immediate attention is needed.

While the operation of the sensor(s) has been described, it will be understood that other embodiments may be implemented in a similar manner, and that combinations of these embodiments may be possible. For example, any number of sensors may be used in a single patient and such sensors may be separate from the prosthetic replacement or repair device. It will also be noted that while the disclosures herein are predominantly described in connection with the replacement of a tricuspid valve, the disclosures are equally applicable to the replacement of other valves, including a bicuspid valve, such as the mitral valve, as well as other implantable medical devices, such as annuloplasty rings or occlusion devices and devices for taking general measurements of the vasculature for delivery of catheters. Additionally, in some variations, one or more of the sensors may be radiopaque to enable visualization during and/or after deployment. Sensors may also be in communication with a delivery system and/or other sensors to aid in placement, valve-in-valve or valve-in-ring procedures, or to function as locators or docking stations.

According to one embodiment of the disclosure, a prosthetic heart valve system comprises:

a prosthetic heart valve including:
a stent extending from an outflow portion to an inflow portion and having an expanded condition and a collapsed condition; and
a valve assembly mounted to the stent; and
a first sensor configured to measure physiological data, the first sensor including a body and a plurality of apertures extending through the body and adapted to receive at least one suture therethrough for attaching the sensor to the stent; and/or
a second sensor configured to measure physiological data, the second sensor including a body and a plurality of apertures extending through the body and adapted to receive at least one suture therethrough for attaching the sensor to the stent; and/or
the first sensor is attached to the inflow portion of the stent with a first suture and the second sensor is attached to the outflow portion of the stent with a second suture; and/or
the plurality of apertures includes four apertures arranged in a rectangular pattern on one end of the body; and/or
the body of the first sensor includes two lateral projections, the plurality of apertures including at least one aperture extending through each of the two projections; and/or
the plurality of apertures includes two apertures extending through each of the two projections; and/or the plurality of apertures includes at least two apertures extending through the body exclusive of the projections; and/or the body of the first sensor includes four lateral projections, the plurality of apertures including at least one aperture extending through each of the four projections; and/or the body of the first sensor has opposed longitudinal sides and opposed ends, the body including a first projection on one of the ends, a second projection on one of the longitudinal sides adjacent the use end and a third projection on another of the longitudinal sides adjacent the one end, and the plurality of apertures includes at least one aperture extending through each of the projections; and/or the first and second sensors are each configured to measure blood pressure and each include an induction coil disposed within the respective body and a capacitor in electrical communication with the inductor coil.

According to another embodiment of the disclosure, a prosthetic heart valve system comprises:

a prosthetic heart valve including:

a stent extending from an outflow portion to an inflow portion and having an expanded condition and a collapsed condition; and a valve assembly mounted to the stent; and a sensor configured to measure physiological data, the sensor including a body, the body having a first side, a second side opposite the first side, and a pair of fingers extending away from the body on the first side of the body, the fingers and the first side of the body defining a channel extending along a length of the body, the sensor being connectable to the stent; and/or each of the fingers has a free edge, and the channel has a maximum width between the fingers that is greater than a distance between the free edges; and/or the first sensor is coupled to a strut of the stent the strut is positioned at least partially within the channel.

According to a further embodiment of the disclosure, a prosthetic heart valve system comprises:

a prosthetic heart valve including:

a stent extending from an outflow portion to an inflow portion and having an expanded condition and a collapsed condition; and a valve assembly mounted to the stent;

a sensor configured to measure physiological data, the sensor including a body; and a first finger having a first end attached to the body and a free end, the free end being configured to hook over at least one strut of the stent to attach the sensor to the stent; and/or the first finger includes a first portion extending substantially orthogonal to the body, a second portion extending substantially orthogonally from the first portion, and a third portion extending from the second portion and substantially parallel to the first portion, a terminal end of the third portion and the body forming a gap therebetween; and/or the first finger is coupled to a face portion of the body; and/or a second finger having a first end attached to the body and a free end, the free end of the first finger and the free end of the second finger forming a gap therebetween.

According to a still another embodiment of the disclosure, a prosthetic heart valve system comprises:

a prosthetic heart valve including:

a stent extending from an outflow portion to an inflow portion and having an expanded condition and a collapsed condition, the stent being formed of a plurality of struts, a strut aperture being formed at an intersection of at least two of the struts; and a valve assembly mounted to the stent; and a sensor configured to measure physiological data, the sensor including a body, the body being configured to be coupled to the stent, wherein the body includes a first body section having a first width, a middle body section having a second width smaller than the first width, and a third body section having a third width greater than the second width and smaller than the first width; and/or the strut aperture has an aperture width smaller than the first width of the first body section and the third width of the third body section; and/or the second width of the middle body section is substantially equal to the aperture width of the strut aperture; and/or the first and third body sections each include projecting members extending laterally beyond the middle body section, and the at least two struts are configured to be positioned between the projecting members of the first and third body members when the sensor is coupled to the strut aperture; and/or the projecting members of the third body section are deflectable.

According to a still a further embodiment of the disclosure, a prosthetic heart valve system comprises:

a prosthetic heart valve including:

a stent extending from an outflow portion to an inflow portion and having an expanded condition and a collapsed condition, the stent being formed of a plurality of struts, a strut aperture being formed at an intersection of at least two of the struts; and a valve assembly mounted to the stent; and a sensor configured to measure physiological data, the sensor including a body configured to be coupled to the stent, wherein the body includes a head having a first width and a shank having a second width smaller than the first width; and/or the strut aperture has an aperture width smaller than the first width of the head; and/or the aperture width is substantially equal to the second width of the shank; and/or a pair of fingers extending laterally from the shank at a spaced distance from the head, each finger extending toward the head in the absence of externally applied forces; and/or the head includes a pair of hooked members each curving toward a corresponding finger; and/or the at least two struts forming the strut aperture are adapted to be positioned between one of the fingers and one of the hooks when the sensor is coupled to the strut aperture.

According to yet another embodiment of the disclosure, a prosthetic heart valve system comprises:

a prosthetic heart valve including:

a stent extending from an outflow portion to an inflow portion and having an expanded condition and a collapsed condition, the stent being formed of a plurality of struts, a strut aperture being formed at an intersection of at least two of the struts; and a valve assembly mounted to the stent; and a sensor configured to measure physiological data, the sensor including a body, the body including a connecting member adapted to couple the sensor to the stent, the connecting member including a shaft projecting away from the body to a free end, and a head at the free end of the shaft; and/or the shaft includes a first shaft member and a second shaft member spaced apart from the first shaft member by a shaft gap, each of the first shaft member and the second shaft member having a free end; and/or the head includes a first head portion on the free end of the first shaft member and a second head portion on the free end of the second shaft member, the first head portion being spaced apart from the second head portion by a head gap; and/or the first shaft member, the second shaft member and the shaft gap collectively have a shaft width, and the first head portion, the second head portion and the head gap collectively have a head width that is greater than the shaft width; and/or the head has a chamfered surface; and/or the connecting member has a relaxed condition and a compressed condition, the head gap being larger in the relaxed condition than in the compressed condition; and/or the head width in the relaxed condition is greater than a width of the strut aperture and the head width in the compressed condition is smaller than the width of the strut aperture.

According to yet a further embodiment of the disclosure, a prosthetic heart valve system comprises:
a prosthetic heart valve including:
a stent extending from an outflow portion to an inflow portion and including a plurality of stent posts, at least one stent post defining an aperture; and
a valve assembly mounted to the stent; and a sensor configured to measure physiological data, the sensor including a body, the body including a plurality of fingers extending away from the body for connecting the sensor to the stent, at least two of the fingers extending away from one another in the absence of applied forces; and/or
the plurality of fingers are spaced apart from one another, the plurality of fingers being deformable so as to simultaneously extend through the aperture of the stent post; and/or
each of the plurality of fingers has a first portion extending from the body and an end portion, the plurality of fingers being deformable so that in a deformed condition, the end portions extend substantially parallel to the first portions, and in a relaxed condition, the end portions extend transversely to the first portions.

According to another embodiment of the disclosure, a sensor system comprises:
a collapsible and expandable sensor frame having an outflow frame section, an inflow frame section, and a frame coupling portion connecting the outflow frame section to the inflow frame section;
a first sensor coupled to the sensor frame, the first sensor including a body, the first sensor being configured to measure physiological data; and
a second sensor coupled to the sensor frame, the second sensor including a body, the second sensor being configured to measure physiological data,
wherein in an expanded condition the outflow frame section and inflow frame section each has an arcuate configuration; and/or the first sensor is coupled to the frame coupling portion at a position closer to the outflow frame section than to the inflow frame section and the second sensor is coupled to the frame coupling portion, at a position closer to the inflow frame section than to the outflow frame section; and/or
the outflow frame section and the inflow frame section are each wires formed with a zig-zag pattern; and/or
the outflow frame section and the inflow frame section each include at least one annular row of cells; and/or
a prosthetic heart valve including:

a stent extending from an outflow portion to an inflow portion; and
a valve assembly mounted to the stent;
wherein the frame coupling portion extends through the stent of the prosthetic heart valve so that the first sensor is positioned closer to the outflow portion of the prosthetic heart valve than to the inflow portion and the second sensor is positioned closer to the inflow portion of the prosthetic heart valve than to the outflow portion; and/or
a prosthetic heart valve including:
a stent extending from an outflow portion to an inflow portion;
a cuff attached to the stent; and
a valve assembly mounted to the stent;
wherein the frame coupling portion extends through the cuff and outside of the valve assembly, the first sensor being positioned on the outflow portion of the prosthetic heart valve and the second sensor being positioned on the inflow portion of the prosthetic heart valve.

According to a further embodiment of the disclosure, a prosthetic heart valve system comprises:
a prosthetic heart valve including:
a support structure extending from an outflow portion to an inflow portion;
a cuff attached to the inflow portion of the support structure; and
a valve assembly mounted to the support structure; and
a first sensor including a body, the first sensor configured to measure physiological data and having a male coupling portion extending from the body, and
a second sensor including a body, the second sensor configured to measure physiological data and having a female coupling, the male coupling portion of the first sensor configured to mate with the female coupling portion of the second sensor; and/or
the male coupling portion is configured to threadingly engage the female coupling portion; and/or
the male coupling portion and the female coupling portion are configured to press-fit together; and/or
the male coupling portion is coupled to the cuff and to the female coupling portion.

According to yet another embodiment of the disclosure a prosthetic heart valve system comprises:
a prosthetic heart valve including:
a stent extending from an outflow portion to an inflow portion and having an expanded condition and a collapsed condition, the stent including a plurality of struts defining at least one annular row of cells, at least one engaging arm, and at least one commissure attachment feature positioned at a terminal end of the stent, the engaging arm having a first position and nested within one of the cells and a second position projecting outwardly from the one cell; and
a valve assembly mounted to the stent; and
a first sensor including a body, the first sensor configured to measure physiological data and being coupled to the engaging arm or to the commissure attachment feature; and/or
the engaging arm and the commissure attachment feature are both positioned on the outflow portion of the stent; and/or
a second sensor including a body, the second sensor configured to measure physiological data and being coupled to the inflow portion of the stent.

According to yet a further embodiment of the disclosure a prosthetic heart valve system comprises:
a prosthetic heart valve including:

a stent extending from an outflow portion to an inflow portion and having an expanded condition and a collapsed condition; and a valve assembly mounted to the stent;

a collapsible and expandable occlusion device configured for positioning between the prosthetic heart valve and a native valve annulus in which the prosthetic heart valve is implanted so that a first end of the occlusion device faces toward the outflow portion of the stent and a second end of the occlusion device faces toward the inflow portion of the stent; and a first sensor configured to be attached to the occlusion device, the first sensor including a body and being configured to measure physiological data; and/or a second sensor configured to be attached to the occlusion device, the second sensor including a body and being configured to measure physiological data; and/or the first sensor is coupled to the first portion of the occlusion device and the second sensor is coupled to the second portion of the occlusion device.

According to still another embodiment of the disclosure, a collapsible and expandable occlusion system for placement within a vasculature of a patient comprises;

a disc-shaped portion coupled to a cylindrical portion by a connector, the cylindrical portion having a first diameter and the disc-shaped portion having a second diameter greater than the first diameter when the occlusion system is in an expanded condition; and a first sensor configured to be attached to the cylindrical portion, the first sensor including a body and being configured to measure physiological data; and/or a second sensor configured to be attached to the disc-shaped portion, the second sensor including a body and being configured to measure physiological data; and/or the disc-shaped portion includes a threaded coupling member and the first sensor has a threaded coupling portion configured to threadingly mate to the threaded coupling member of the disc-shaped portion; and/or the cylindrical portion includes a threaded coupling member and the second sensor has a threaded coupling portion configured to threadingly mate to the threaded coupling member of the cylindrical portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features described in connection with one embodiment may be combined with features described in connection with other embodiments.

The invention claimed is:

1. A prosthetic heart valve system comprising:
a prosthetic heart valve including:
a stent extending along a longitudinal axis from an outflow portion to an inflow portion and having an expanded condition and a collapsed condition; and
a valve assembly mounted to the stent; and
a first sensor configured to measure physiological data, the first sensor including a body extending along a body axis and a plurality of apertures extending through the body on opposite sides of the body axis,
wherein a first suture attaches the first sensor to the stent via at least some of the plurality of apertures so that, in the expanded condition of the stent, the longitudinal axis of the stent is not parallel to the body axis of the first sensor, and in the collapsed condition of the stent, the longitudinal axis of the stent is parallel to the body axis of the first sensor.

2. The prosthetic heart valve system of claim 1, further comprising:
a second sensor configured to measure physiological data, the second sensor including a body and a plurality of apertures extending through the body of the second sensor and adapted to receive at least one suture therethrough for attaching the second sensor to the stent.

3. The prosthetic heart valve system of claim 2, wherein the first sensor is attached to the inflow portion of the stent and the second sensor is attached to the outflow portion of the stent with a second suture.

4. The prosthetic heart valve system of claim 2, wherein the first and second sensors are each configured to measure blood pressure and each include an induction coil disposed within the respective body and a capacitor in electrical communication with the induction coil.

5. The prosthetic heart valve system of claim 1, wherein the plurality of apertures includes four apertures arranged in a rectangular pattern on one end of the body.

6. The prosthetic heart valve system of claim 1, wherein the body of the first sensor includes two lateral projections, the plurality of apertures including at least one aperture extending through each of the two projections.

7. The prosthetic heart valve system of claim 6, wherein the plurality of apertures includes two apertures extending through each of the two projections.

8. The prosthetic heart valve system of claim 6, wherein the plurality of apertures includes at least two additional apertures extending through the body exclusive of the projections.

9. The prosthetic heart valve of claim 6, wherein the inflow portion of the stent includes a first circumferential row of cells, each cell being defined by a plurality of struts, the at least one aperture in each of the two projections being positioned on opposite sides of a selected strut of one of the cells.

10. The prosthetic heart valve of claim 9, wherein a fastener extends from the at least one aperture in a first of the two lateral projections to the at least one aperture in a second of the two lateral projections, the selected strut being positioned between the fastener and the body of the first sensor.

11. The prosthetic heart valve of claim 10, wherein the fastener has a first position relative to the selected strut when the stent is in the collapsed condition, and a second position relative to the selected strut when the stent is in the expanded condition, the first position being different than the second position.

12. The prosthetic heart valve system of claim 1, wherein the body of the first sensor includes four lateral projections, the plurality of apertures including at least one aperture extending through each of the four projections.

13. The prosthetic heart valve system of claim 1, wherein the body of the first sensor has opposed longitudinal sides and opposed ends, the body of the first sensor including a first projection on one of the ends, a second projection on one of the longitudinal sides adjacent the one end and a third projection on another of the longitudinal sides adjacent the one end, and the plurality of apertures includes at least one aperture extending through each of the projections.

14. The prosthetic heart valve of claim 1, wherein the valve assembly includes a plurality of leaflets, a pair of adjacent leaflets being coupled to one another and the stent at a commissure attachment feature, the first sensor being aligned with the commissure attachment feature in a longitudinal direction of the stent extending from the inflow portion to the outflow portion.

15. The prosthetic heart valve of claim 1, wherein the inflow portion of the stent includes a first circumferential row of cells, and a first of the plurality of apertures is positioned in a first cell in the first circumferential row, and a second of the plurality of apertures is positioned in a second cell in the first circumferential row directly adjacent the first cell.

16. The prosthetic heart valve of claim 15, wherein the first suture extends from the first of the plurality of apertures to the second of the plurality of apertures.

* * * * *